(12) United States Patent
Benson et al.

(10) Patent No.: US 7,645,785 B2
(45) Date of Patent: Jan. 12, 2010

(54) BENZIMIDAZOLE DERIVATIVES

(75) Inventors: Gregory Martin Benson, Therwil (CH); Konrad Bleicher, Freiburg (DE); Alexander Chucholowski, San Diego, CA (US); Henrietta Dehmlow, Grenzach-Wyhlen (DE); Uwe Grether, Efringen-Kirchen (DE); Bernd Kuhn, Liestal (CH); Rainer E. Martin, Basel (CH); Eric J. Niesor, Nyon (CH); Narendra Panday, Munich (DE); Hans Richter, Grenzach-Wyhlen (DE); Franz Schuler, Riehen (CH); Xavier Marie Warot, Strasbourg (FR); Matthew Wright, Basel (CH); Minmin Yang, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/821,265

(22) Filed: Jun. 22, 2007

(65) Prior Publication Data
US 2008/0021027 A1    Jan. 24, 2008

(30) Foreign Application Priority Data
Jun. 29, 2006   (EP)   .................................. 06116302

(51) Int. Cl.
*A61K 31/4184* (2006.01)
*C07D 235/04* (2006.01)
*C07D 235/18* (2006.01)
(52) U.S. Cl. .................. 514/394; 548/304.7; 548/309.7
(58) Field of Classification Search .............. 514/234.5, 514/235.5, 312, 322, 338, 361, 380, 381, 514/387, 394; 544/131, 139; 546/153, 199, 546/273.7; 548/127, 243, 251, 304.7, 306.1, 548/306.4, 302.7, 304.4, 309.7
See application file for complete search history.

(56) References Cited

U.S. PATENT DOCUMENTS
2003/0055057 A1    3/2003   Blume et al.
2005/0107475 A1    5/2005   Jones et al.

FOREIGN PATENT DOCUMENTS
WO    WO 97/12615 A1    4/1997
WO    WO 01/21634 A1    3/2001
WO    WO 03/066629 A2   8/2003

OTHER PUBLICATIONS

Remington et al., The Science and Practice of Pharmacy, 2000, Lippincott Williams and Wilkins, 20th Edition, pp. 218-220.*
Tumelty et al., Solid-Phase Synthesis of Substituted Benzimidazoles, 1999, Tetrahedron Letters, 40, 6185-6188.*
Gross et al., "The Peptides", vol. 2, pp. 365-381 (1980) Academic Press, NY.
Tempest et al., Tet. Lett., 42, pp. 4959-4962 (2001).
Tempest et al., Tet. Lett., 42, pp. 4963-4968 (2001).
Zhang et al., Tet. Lett., 45, pp. 6757-6760 (2004).

* cited by examiner

*Primary Examiner*—Kamal A Saeed
*Assistant Examiner*—Kristin Bianchi
(74) *Attorney, Agent, or Firm*—George W. Johnston; Dennis P. Tramaloni; Brian C. Remy

(57) ABSTRACT

The invention is concerned with novel benzimidazole derivatives of formula (I)

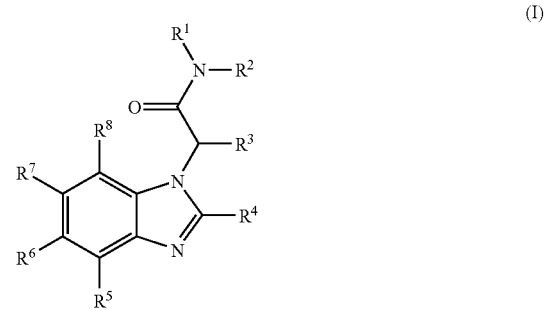

wherein $R^1$ to $R^8$ are as defined in the description and in the claims, as well as physiologically acceptable salts and esters thereof. These compounds bind to Farnesoid-X-receptors (FXR) and can be used to treat diseases which are modulated by FXR agonists such as diabetes and dyslipidemia.

65 Claims, No Drawings

BENZIMIDAZOLE DERIVATIVES

PRIORITY TO RELATED APPLICATION(S)

This application claims the benefit of European Patent Application No. 06116302.8, filed Jun. 29, 2006, which is hereby incorporated by reference in its entirety.

BACKGROUND OF THE INVENTION

The present invention is concerned with novel benzimidazole derivatives, their manufacture, pharmaceutical compositions containing them, and their use to treat diseases which are modulated by FXR agonists.

The Farnesoid-X-receptor (FXR) is a member of the nuclear hormone receptor superfamily of transcription factors. FXR was originally identified as a receptor activated by farnesol, and subsequent studies revealed a major role of FXR as a bile acid receptor [Makishima, M., Okamoto, A. Y., Repa, J. J., Tu, H., Learned, R. M., Luk, A., Hull, M. V., Lustig, K. D., Mangelsdorf, D. J. and Shan, B. (1999) Identification of a nuclear receptor for bile acids. Science 284, 1362-5]. FXR is expressed in liver, intestine, kidney, and the adrenal gland. Four splice isoforms have been cloned in humans.

Among the major bile acids, chenodeoxycholic acid is the most potent FXR agonist. Binding of bile acids or synthetic ligands to FXR induces the transcriptional expression of small heterodimer partner (SHP), an atypical nuclear receptor family member that binds to several other nuclear hormone receptors, including LRH-1 and LXRalpha and blocks their transcriptional functions [Lu, T. T., Makishima, M., Repa, J. J., Schoonjans, K., Kerr, T. A., Auwerx, J. and Mangelsdorf, D. J. (2000) Molecular basis for feedback regulation of bile acid synthesis by nuclear receptors. Mol Cell 6, 507-15]. CYP7A1 and CYP8B are enzymes involved in hepatic bile acid synthesis. FXR represses their expression via activation of the SHP pathway. FXR directly induces the expression of bile acid-exporting transporters for the ABC family in hepatocytes, including the bile salt export pump (ABCB11) and the multidrug resistance associated protein 2 (ABCC2) [Kast, H. R., Goodwin, B., Tarr, P. T., Jones, S. A., Anisfeld, A. M., Stoltz, C. M., Tontonoz, P., Kliewer, S., Willson, T. M. and Edwards, P. A. (2002) Regulation of multidrug resistance-associated protein 2 (ABCC2) by the nuclear receptors pregnane X receptor, farnesoid X-activated receptor, and constitutive androstane receptor. J Biol Chem 277, 2908-15; Ananthanarayanan, M., Balasubramanian, N., Makishima, M., Mangelsdorf, D. J. and Suchy, F. J. (2001) Human bile salt export pump promoter is transactivated by the farnesoid X receptor/bile acid receptor. J Biol Chem 276, 28857-65]. FXR knockout mice have impaired resistance to bile acid-induced hepatotoxicity and synthetic FXR agonists have been shown to be hepatoprotective in animal models of cholestasis [Liu, Y., Binz, J., Numerick, M. J., Dennis, S., Luo, G., Desai, B., MacKenzie, K. I., Mansfield, T. A., Kliewer, S. A., Goodwin, B. and Jones, S. A. (2003) Hepatoprotection by the farnesoid X receptor agonist GW4064 in rat models of intra- and extra-hepatic cholestasis. J Clin Invest 112, 1678-87; Sinal, C. J., Tohkin, M., Miyata, M., Ward, J. M., Lambert, G. and Gonzalez, F. J. (2000) Targeted disruption of the nuclear receptor FXR/BAR impairs bile acid and lipid homeostasis. Cell 102, 731-44]. These data show that FXR protects hepatocytes from bile acid toxicity by suppressing both cellular synthesis and import of bile acids and stimulating their biliary excretion.

The process of enterohepatic circulation of bile acids is also a major regulator of serum cholesterol homeostasis. After biosynthesis from cholesterol in the liver, bile acids are secreted with bile into the lumen of the small intestine to aid in the digestion and absorption of fat and fat-soluble vitamins. The ratio of different bile acids determines the hydrophilicity of the bile acid pool and its ability to solubilize cholesterol. FXR activation increases the hydrophilicity of the pool, decreasing the intestinal solubilization of cholesterol, effectively blocking its absorption. Decrease absorption would be expected to result in lowering of plasma cholesterol levels. Indeed direct inhibitors of cholesterol absorption such as ezetimibe decrease plasma cholesterol, providing some evidence to support this hypothesis. However ezetimibe has limited efficacy which appears due to feedback upregulation of cholesterol synthesis in cells attempting to compensate for depletion of cholesterol. Recent data have shown that FXR opposes this effect in part by directly repressing the expression of HMGCoA reductase via a pathway involving SHP and LRH1 [Datta, S., Wang, L., Moore, D. D. and Osborne, T. F. (2006) Regulation of 3-hydroxy-3-methylglutaryl coenzyme A reductase promoter by nuclear receptors liver receptor homologue-1 and small heterodimer partner: a mechanism for differential regulation of cholesterol synthesis and uptake. J Biol Chem 281, 807-12]. FXR also decreases hepatic synthesis of triglycerides by repressing SREBP1-c expression by an alternate pathway involving SHP and LXRalpha. Thus compounds which modulate FXR activity may show superior therapeutic efficacy on plasma cholesterol and triglyceride lowering than current therapies.

Most patients with coronary artery disease have high plasma levels of atherogenic LDL. The HMGCoA reductase inhibitors (statins) are effective at normalizing LDL-C levels but reduce the risk for cardiovascular events such as stroke and myocardial infarction by only about 30%. Additional therapies targeting further lowering of atherogenic LDL as well as other lipid risk factors such as high plasma triglyceride levels and low HDL-C levels are needed.

A high proportion of type 2 diabetic patients in the United States have abnormal concentrations of plasma lipoproteins. The prevalence of total cholesterol >240 mg/dl is 37% in diabetic men and 44% in diabetic women and the prevalence for LDL-C>160 mg/dl are 31% and 44%, respectively in these populations. Diabetes is a disease in which a patient's ability to control glucose levels in blood is decreased because of partial impairment in the response to insulin. Type II diabetes (T2D), also called non-insulin dependent diabetes mellitus (NIDDM), accounts for 80-90% of all diabetes cases in developed countries. In T2D, the pancreatic Islets of Langerhans produce insulin but the primary target tissues (muscle, liver and adipose tissue) develop a profound resistance to its effects. The body compensates by producing more insulin ultimately resulting in failure of pancreatic insulin-producing capacity. Thus T2D is a cardiovascular-metabolic syndrome associated with multiple comorbidities including dyslipidemia and insulin resistance, as well as hypertension, endothelial dysfunction and inflammatory atherosclerosis.

The first line treatment for dyslipidemia and diabetes is a low-fat and low-glucose diet, exercise and weight loss. Compliance can be moderate and treatment of the various metabolic deficiencies that develop becomes necessary with, for example, lipid-modulating agents such as statins and fibrates, hypoglycemic drugs such as sulfonylureas and metformin, or insulin sensitizers of the thiazolidinedione (TZD) class of PPARgamma-agonists. Recent studies provide evidence that modulators of FXR may have enhanced therapeutic potential by providing superior normalization of both LDL-C and triglyceride levels, currently achieved only with combinations of existing drugs and, in addition, may avoid feedback effects on cellular cholesterol homeostasis.

The novel compounds of the present invention exceed the compounds known in the art, inasmuch as they bind to and selectively modulate FXR very efficiently. Consequently, cholesterol absorption is reduced, LDL cholesterol and triglycerides are lowered, and inflammatory atherosclerosis is reduced. Since multiple facets of combined dyslipidemia and cholesterol homeostasis are addressed by FXR modulators, they are expected to have an enhanced therapeutic potential compared to the compounds already known in the art.

SUMMARY OF THE INVENTION

The present invention relates to the compounds of the formula (I) including all pharmaceutically acceptable salts and esters thereof wherein formula (I) is:

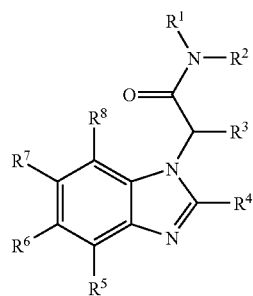

(I)

wherein $R^1$-$R^8$ are as defined in the detailed description and in the claims. The compounds of the present invention are modulators of the FXR receptor and are useful in the treatment and/or prophylaxis of diseases which are modulated by FXR agonists such as dyslipidemia including increased lipid and cholesterol levels, high LDL-cholesterol, high triglycerides, and low HDL-cholesterol, as well as atherosclerotic disease, diabetes, non-insulin dependent diabetes mellitus, metabolic syndrome, cholesterol gallstone disease, cholestasis/fibrosis of the liver, diseases of cholesterol absorption, cancer, gastrointestinal cancer, osteoporosis, peripheral occlusive disease, ischemic stroke, Parkinson's disease and/or Alzheimer's disease.

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven carbon atom(s). In preferred embodiments, said lower group consists of one to four carbon atom(s).

The term "halogen" refers to fluorine, chlorine, bromine or iodine. In preferred embodiments, the halogen is fluorine, chlorine or bromine.

The term "alkyl", alone or in combination with other groups, refers to a branched or straight-chain monovalent saturated aliphatic hydrocarbon radical of one to twenty carbon atoms. In preferred embodiments the alkyl has one to sixteen carbon atoms, and more preferably one to ten carbon atoms. Lower-alkyl groups as described below are also preferred embodiments of the invention.

The term "$C_{1-10}$-alkyl" refers to a branched or straight-chain monovalent saturated aliphatic hydrocarbon radical of one to ten carbon atoms, such as methyl, ethyl, n-propyl, isopropyl, n-butyl, s-butyl, t-butyl, pentyl, 1,1,3,3-tetramethyl-butyl, and the like.

The term "lower-alkyl", alone or in combination with other groups, refers to a branched or straight-chain monovalent alkyl radical of one to seven carbon atoms. In preferred embodiments the lower alkyl has one to four carbon atoms. This term is further exemplified by such radicals as methyl, ethyl, n-propyl, isopropyl, n-butyl, s-butyl, t-butyl and the like. Lower-alkyl groups can optionally be substituted, for example, by hydroxy; wherein such a hydroxy substituted lower-alkyl-group is referred to as "hydroxy-lower-alkyl". Unsubstituted lower-alkyl groups are preferred.

The term "fluoro-lower-alkyl" refers to lower-alkyl groups which are mono- or multiply substituted with fluorine. Examples of fluoro-lower-alkyl groups include $CFH_2$, $CF_2H$, $CF_3$, $CF_3CH_2$, $CF_3(CH_2)_2$, $(CF_3)_2CH$, and $CF_2H$—$CF_2$.

The term "amino," alone or in combination with other groups, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents; or the two nitrogen substituents together forming a ring, such as, for example, —$NH_2$, methylamino, ethylamino, dimethylamino, diethylamino, methylethylamino, pyrrolidin-1-yl or piperidino, etC. (preferably a primary amino, dimethylamino and diethylamino, particularly a dimethylamino). The term "formylamino" refers to the group HC(O)—N(H)—.

The term "cycloalkyl" refers to a monovalent carbocyclic radical of 3 to 10 carbon atoms. In preferred embodiments the cycloalkyl has 3 to 6 carbon atoms, such as cyclopropyl, cyclobutyl, cyclopentyl, or cyclohexyl. A cycloalkyl group can optionally be substituted as described in the description and claims.

The term "partially unsaturated cycloalkyl" refers to a monovalent carbocyclic radical of 3 to 10 carbon atoms. In preferred embodiments the partially unsaturated cycloalkyl has 4 to 8 carbon atoms, with 1-4 double bonds, such as, for example, cyclohexene, cyclopentene, cycloheptadiene.

The term "alkoxy" refers to the group R'—O—, wherein R' is an alkyl. The term "lower-alkoxy" refers to the group R'—O—, wherein R' is a lower-alkyl.

The term "fluoro-lower-alkoxy" refers to the group R"—O—, wherein R" is fluoro-lower-alkyl. Examples of fluoro-lower-alkoxy groups include $CFH_2$—O, $CF_2H$—O, $CF_3$—O, $CF_3CH_2$—O, $CF_3(CH_2)_2$—O, $(CF_3)_2CH$—O, and $CF_2H$—$CF_2$—O.

The term "aryl", alone or in combination with other groups, relates to the phenyl or naphthyl group. In preferred embodiments the aryl is a phenyl group, which can optionally be substituted by 1 to 5, preferably 1 to 3, substituents independently selected from the group consisting of lower-alkyl, lower-alkoxy, halogen, hydroxy, CN, $CF_3$, amino, aminocarbonyl, carboxy, $NO_2$, lower-alkylsulfonyl, aminosulfonyl, lower-alkylcarbonyl, lower-alkylcarbonyloxy, lower-alkylcarbonyl-N(H), lower-alkyl-carbonyl-N(lower-alkyl), lower-alkoxycarbonyl, fluoro-lower-alkyl, fluoro-lower-alkoxy, cycloalkyl, phenyloxy, methyl-oxadiazolyl, morpholinyl, and formylamino. Preferred substituents for the aryl group are halogen, lower-alkyl, fluoro-lower-alkyl and CN. Furthermore, aryl groups may preferably be substituted as described in the description and claims.

The term "heteroaryl" refers to an aromatic 5 to 6 membered monocyclic ring or a 9 to 10 membered bicyclic ring which can comprise 1, 2 or 3 atoms independently selected from the group consisting of nitrogen, oxygen and sulphur. Examples of heteroaryls include furyl, pyridinyl, 2-oxo-1,2-dihydro-pyridinyl, pyridazinyl, pyrimidinyl, pyrazinyl, thiophenyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzodioxolyl, benzoimidazolyl, indolyl, isoindolyl, 1,3-dioxo-isoindolyl, quinolinyl, indazolyl, benzoisothiazolyl, benzoxazolyl, benzoisoxazolyl, benzothiophenyl, benzothiazolyl, benzofuranyl and quinoxalinyl. Preferred heteroaryl groups are pyridinyl, pyrimidinyl, oxazolyl, benzodioxolyl, thiophenyl, pyrrolyl, 2-oxo-1,2-dihydro-pyridinyl, indolyl, quinolinyl, 1,3-dioxo-isoindolyl, imidazolyl, benzothiophenyl, benzothiazolyl, benzofuranyl, quinoxalinyl, pyrazolyl, isoxazolyl, benzimidazolyl and furyl. A heteroaryl group may have a substitution pattern as described earlier in connection with the term "aryl". Furthermore, a heteroaryl group may preferably be substituted as described in the description and claims.

The term "heterocyclyl" refers to 5 to 6 membered monocyclic ring or an 8 to 10 membered bicyclic or tricyclic ring which comprises 1, 2 or 3 atoms independently selected from the group consisting of nitrogen, oxygen, and sulphur. Examples of heterocyclyls include morpholinyl, thiomorpholinyl, 1,1-dioxo-thiomorpholinyl, piperidinyl, 2-oxo-piperidinyl, pyrrolidinyl, 2-oxo-pyrrolidinyl, piperazin-2-one, 8-oxa-3-aza-bicyclo[3.2.1]octyl, piperazinyl and tetrahydropyranyl. Preferred heterocyclyl groups are piperidinyl, 2-oxo-pyrrolidinyl, pyrrolidinyl, 2-oxo-piperidinyl and tetrahydropyranyl. A heterocyclyl may optionally have a substitution pattern as described earlier in connection with the term "aryl". Furthermore, a heterocyclyl group may preferably be substituted as described in the description and claims.

In addition, the terms above may be combined to refer to various substitutents in the description and claims which are combinations of the groups as defined above. Unless otherwise indicated, these combined terms are read from left to right with the last group (the term to the far right which is not in a parenthetical) being the attachment point for the substitutent to the base molecule. For example, if the $R^1$ substituent in formula (I) is "lower-alkoxy-lower-alkyl" the lower-alkyl portion is attached to the nitrogen atom of the base molecule while the lower-alkoxy portion is attached to the lower-alkyl (i.e., in essence the lower-alkoxy group is a substituent of the lower-alkyl group which is bonded to the base molecule).

In reference to a particular group or molecule, the term "substituted" refers to the fact that at least one of the hydrogen atoms of that group or molecule is replaced by some other substituent.

The term "protecting group" refers to groups which are used to protect functional groups, particularly hydroxy groups, temporarily. Examples of protecting groups are benzyl, p-methoxybenzyl, t-butyl-dimethylsilyl, t-butyl-diphenylsilyl and (for protection of amino groups) t-Butoxycarbonyl (Boc) and benzyloxycarbonyl.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluensulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) in which a COOH group is present can further form salts with bases. Examples of such salts are alkaline, earth-alkaline and ammonium salts such as e.g. Na—, K—, Ca— and trimethylammonium salt. The term "pharmaceutically acceptable salts" also refers to such salts. Salts obtained by the addition of an acid are preferred.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, preferably from about 0.1 mg to about 1,000 mg, more preferably from about 0.5 to 500 mg, and more preferably from about 1 mg to 100 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

In detail, the present invention relates to the compounds of formula (I) and all pharmaceutically acceptable salts and esters thereof wherein formula (I) is:

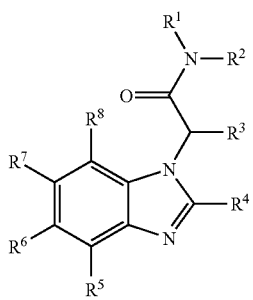

(I)

wherein:
(a) R¹ is selected from the group consisting of:
  (1) $C_{1-10}$-alkyl,
  (2) lower-alkoxy-lower-alkyl,
  (3) lower-alkoxy-carbonyl-lower-alkyl,
  (4) cycloalkyl,
  (5) cycloalkyl-lower-alkyl,
  (6) aryl,
  (7) aryl-lower-alkyl,
  (8) di-aryl-lower-alkyl,
  (9) heteroaryl,
  (10) heteroaryl-lower-alkyl,
  (11) heterocyclyl, and
  (12) heterocyclyl-lower-alkyl,
  wherein the cycloalkyl, aryl, heteroaryl or heterocyclyl group of any option for R¹ above is optionally substituted with 1 to 3 substituents independently selected from the group consisting of: lower-alkyl, lower-alkoxy, lower-alkoxy-carbonyl, morpholinyl, formylamino, halogen, hydroxy, fluoro-lower-alkyl, fluoro-lower-alkoxy, lower-alkyl-carbonyl-N(lower-alkyl), lower-alkyl-carbonyl-N(H), NH₂, N(H, lower-alkyl), N(lower-alkyl)₂, carboxy, carbamoyl, N(H, lower-alkyl)C(O), and N(lower-alkyl)₂C(O);
(b) R² is hydrogen- or lower-alkyl;
(c) R³ is selected from the group consisting of:
  (1) lower-alkyl,
  (2) cycloalkyl,
  (3) partially unsaturated cycloalkyl,
  (4) aryl,
  (5) aryl-lower-alkyl,
  (6) heteroaryl,
  (7) heteroaryl-lower-alkyl,
  (8) heterocyclyl, and
  (9) heterocyclyl-lower-alkyl,
  wherein the aryl, heteroaryl or heterocyclyl group of any option for R³ above is optionally substituted with 1 to 3 substituents independently selected from the group consisting of halogen, lower-alkyl, lower-alkoxy, lower-alkoxy-carbonyl, hydroxy, fluoro-lower-alkyl, fluoro-lower-alkoxy, NH₂, N(H, lower-alkyl), N(lower-alkyl)₂, lower-alkyl-carbonyl-N(lower-alkyl), lower-alkyl-carbonyl-N(H), carboxy, carbamoyl, N(H, lower-alkyl)C(O), and N(lower-alkyl)₂C(O);
(d) R⁴ is selected from the group consisting of:
  (1) heteroaryl which is optionally substituted with 1 to 3 substituents independently selected from the group consisting of lower-alkyl, phenyl, lower-alkoxy-carbonyl, carboxy, carbamoyl, N(H, lower-alkyl)C(O), N(lower-alkyl)₂C(O), NH₂, N(H, lower-alkyl), N(lower-alkyl)₂, lower-alkyl-carbonyl-N(lower-alkyl), lower-alkyl-carbonyl-N(H), hydroxy, lower-alkoxy, halogen, fluoro-lower-alkyl, fluoro-lower-alkoxy, cyano and morpholinyl;
  (2) substituted naphthyl or substituted phenyl, substituted with 1 to 3 substituents independently selected from the group consisting of halogen, hydroxy, NH₂, CN, hydroxy-lower-alkyl, lower-alkoxy, lower-alkyl-carbonyl, lower-alkyl-carbonyl-N(H), lower-alkoxy-carbonyl, sulfamoyl, di-lower-alkyl-sulfamoyl, lower-alkyl-sulfonyl, thiophenyl, pyrazolyl, thiadiazolyl, imidazolyl, triazolyl, tetrazolyl, 2-oxo-pyrrolidinyl, pyrrolyl, pyridinyl, pyrimidinyl, 2-oxo-piperidinyl, pyrrolidinyl, piperidinyl, oxazolyl, thiazolyl, oxadiazolyl, carboxy, lower-alkyl, fluoro-lower-alkyl, fluoro-lower-alkoxy, N(H, lower-alkyl), N(lower-alkyl)₂, lower-alkyl-carbonyl-N(lower-alkyl), carbamoyl, N(H, lower-alkyl)C(O), N(lower-alkyl)₂C(O), lower-alkyl-sulfamoyl, lower-alkenyl, benzoyl, phenoxy, and phenyl wherein said phenyl is itself optionally substituted with 1 to 3 substituents independently selected from the group consisting of halogen and fluoro-lower-alkyl;
  (3) unsubstituted naphthyl; and
  (4) unsubstituted phenyl if R¹ is cycloalkyl and R³ is cycloalkyl;
(e) R⁵, R⁶, R⁷ and R⁸ are independently from each other selected from the group consisting of:
  (1) hydrogen,
  (2) halogen, and
  (3) lower-alkyl;
  or alternatively, R⁵ and R⁶ are bound together, or R⁶ and R⁷ are bound together, or R⁷ and R⁸ are bound together, to form a 4-7 membered aromatic or non-aromatic carbocyclic or heterocyclic ring together with the carbon atoms to which they are attached; and
(f) with the proviso that the compound of formula (I) is not 2-[2-(2-chloro-phenyl)-benzoimidazol-1-yl]-4-methyl-pentanoic acid butylamide, or 2-(2-benzo[1,3]dioxol-5-yl-benzoimidazol-1-yl)-N-benzyl-butyramide.

For the compounds of formula (I) as described above, it is preferred that R⁴ is selected from the group consisting of:
(1) heteroaryl which is optionally substituted with 1 to 3 substituents independently selected from the group consisting of lower-alkyl, phenyl, lower-alkoxy-carbonyl, carboxy, carbamoyl, N(H, lower-alkyl)C(O), N(lower-alkyl)₂C(O), NH₂, N(H, lower-alkyl), N(lower-alkyl)₂, lower-alkyl-carbonyl-N(lower-alkyl), lower-alkyl-carbonyl-N(H), hydroxy, lower-alkoxy, halogen, fluoro-lower-alkyl and fluoro-lower-alkoxy;
(2) substituted naphthyl or substituted phenyl, substituted with 1 to 3 substituents independently selected from the group consisting of halogen, hydroxy, NH₂, CN, hydroxy-lower-alkyl, lower-alkoxy, lower-alkyl-carbonyl, lower-alkyl-carbonyl-N(H), lower-alkoxy-carbonyl, sulfamoyl, di-lower-alkyl-sulfamoyl, lower-alkyl-sulfonyl, thiophenyl, pyrazolyl, thiadiazolyl, imidazolyl, triazolyl, tetrazolyl, 2-oxo-pyrrolidinyl, pyrrolyl, pyridinyl, pyrimidinyl, 2-oxo-piperidinyl, pyrrolidinyl, piperidinyl, oxazolyl, thiazolyl, oxadiazolyl, carboxy, lower-alkyl, fluoro-lower-alkyl, fluoro-lower-alkoxy, N(H, lower-alkyl), N(lower-alkyl)₂, lower-alkyl-carbonyl-N(lower-alkyl), carbamoyl, N(H, lower-alkyl)C(O), N(lower-alkyl)₂C(O), and lower-alkyl-sulfamoyl;
(3) unsubstituted naphthyl; and
(4) unsubstituted phenyl if R¹ is cycloalkyl and R³ is cycloalkyl;

Compounds of formula (I) are individually preferred and physiologically acceptable salts thereof are individually preferred and pharmaceutically acceptable esters thereof are individually preferred, with the compounds of formula (I) being particularly preferred.

The compounds of formula (I) can have one or more asymmetric carbon atoms and can therefore exist as an enantiomeric mixture, diastereomeric mixture or as optically pure compounds.

Preferred compounds of formula (I) as described above are those, wherein $R^1$ is $C_{1-10}$-alkyl, lower-alkoxy-lower-alkyl, lower-alkoxy-carbonyl-lower-alkyl, cycloalkyl, cycloalkyl-lower-alkyl, phenyl, phenyl-lower-alkyl, di-phenyl-lower-alkyl, heterocyclyl or heterocyclyl-lower-alkyl wherein the heterocyclyl is selected from the group consisting of piperidinyl and 2-oxo-pyrrolidinyl, and wherein the cycloalkyl, phenyl or heterocyclyl group is optionally substituted with 1 to 3 substituents independently selected from the group consisting of lower-alkyl, lower-alkoxy, lower-alkoxy-carbonyl, morpholinyl and formylamino.

Preferably, $R^1$ is $C_{1-10}$-alkyl, cycloalkyl or phenyl, wherein said phenyl is optionally substituted one or two times with lower-alkyl. More preferably, $R^1$ is 1,1,3,3-tetramethyl-butyl, cyclopentyl, cyclohexyl or 2,5-dimethyl-phenyl.

Other preferred compounds as defined above are those, wherein $R^1$ is tetrahydropyranyl, cycloalkyl which is substituted one or two times with halogen, or phenyl which is substituted one or two times with lower-alkyl; and in particular, wherein $R^1$ is tetrahydropyran-4-yl, 4,4-difluoro-cyclohexyl or 2,6-dimethyl-phenyl.

Other preferred compounds of formula (I) as described above are those, wherein $R^2$ is hydrogen. Furthermore, compounds of formula (I) are preferred, wherein $R^3$ is lower-alkyl, cycloalkyl, partially unsaturated cycloalkyl, phenyl, phenyl-lower-alkyl or heteroaryl, wherein said heteroaryl is selected from the group consisting of pyridinyl and benzodioxolyl, and wherein said phenyl or heteroaryl group is optionally substituted with 1 to 3 substituents independently selected from the group consisting of halogen, lower-alkyl, lower-alkoxy, $NH_2$, N(H, lower-alkyl) and N(lower-alkyl)$_2$. Preferably, $R^3$ is cycloalkyl, phenyl, phenyl-lower-alkyl or pyridinyl. More preferably, $R^3$ is cyclopentyl, cyclohexyl, phenyl, 3-phenyl-propyl or pyridin-2-yl. Other preferred compounds are those, wherein $R^3$ is lower-alkyl, tetrahydropyranyl or phenyl which is substituted with 1 to 3 substituents independently selected from fluoro-lower-alkyl and fluoro-lower-alkoxy; preferably wherein $R^3$ is lower-alkyl or tetrahydropyranyl, and more preferably wherein $R^3$ is isobutyl, pentyl or tetrahydropyran-2-yl.

Another preferred embodiment of the present invention relates to compounds of formula (I) as described above, wherein $R^4$ is selected from the group consisting of:
(1) heteroaryl selected from the group consisting of thiophenyl, pyrrolyl, 2-oxo-1,2-dihydropyridinyl, indolyl, quinolinyl and 1,3-dioxo-isoindolyl, wherein said heteroaryl is optionally substituted with 1 to 2 substituents independently selected from the group consisting of lower-alkyl and phenyl;
(2) substituted naphthyl or substituted phenyl, substituted with 1 to 3 substituents independently selected from the group consisting of halogen, hydroxy, $NH_2$, CN, hydroxy-lower-alkyl, lower-alkoxy, lower-alkyl-carbonyl, lower-alkyl-carbonyl-N(H), lower-alkoxy-carbonyl, sulfamoyl, di-lower-alkyl-sulfamoyl, lower-alkyl-sulfonyl, thiophenyl, pyrazolyl, thiadiazolyl, imidazolyl, triazolyl, tetrazolyl, and 2-oxo-pyrrolidinyl;
(3) unsubstituted naphthyl; and
(4) unsubstituted phenyl if $R^1$ is cycloalkyl and $R^3$ is cycloalkyl.

Preferably, $R^4$ is selected from the group consisting of:
(1) heteroaryl selected from the group consisting of thiophenyl, 2-oxo-1,2-dihydro-pyridinyl and quinolinyl, wherein said thiophenyl is optionally substituted with phenyl; and
(2) substituted naphthyl or substituted phenyl, substituted with 1 to 2 substituents independently selected from the group consisting of hydroxy-lower-alkyl, lower-alkoxy, lower-alkyl-carbonyl-N(H), imidazolyl, and tetrazolyl.
(3) unsubstituted naphthyl; and
(4) unsubstituted phenyl if $R^1$ is cycloalkyl and $R^3$ is cycloalkyl.

Each of the options (1), (2), (3), and (4) given above individually constitutes a preferred embodiment.

More preferably, $R^4$ is 2,4-dimethoxy-phenyl, napthalen-2-yl, 4-hydroxymethyl-phenyl, 4-(tetrazolyl-5-yl)-phenyl, 4-(imidazol-2-yl)-phenyl, 4-acetylamino-phenyl, 5-phenyl-thiophen-2-yl, 2-oxo-1,2-dihydro-pyridin-4-yl or quinolin-6-yl.

Other preferred compounds are those, wherein $R^4$ is selected from the group consisting of:
(1) heteroaryl selected from the group consisting of pyridinyl, pyrazolyl, isoxazolyl, benzimidazolyl, furanyl, thiophenyl, indolyl, benzo[b]thiophenyl, benzothiazolyl, benzofuranyl and quinoxalinyl, wherein said heteroaryl is optionally substituted with 1 to 2 substituents independently selected from the group consisting of halogen, CN, NH2, N(lower-alkyl)2, lower-alkyl, lower-alkoxy, fluoro-lower-alkyl and morpholinyl;
(2) substituted naphthyl or substituted phenyl, substituted with 1 to 3 substituents independently selected from the group consisting of carbamoyl, halogen, lower-alkyl) fluoro-lower-alkyl, fluoro-lower-alkoxy, lower-alkenyl, N(lower-alkyl)2, N(H, lower-alkyl)CO, benzoyl, phenoxy, and phenyl wherein said phenyl is optionally substituted with 1 to 3 substituents independently selected from the group consisting of halogen and fluoro-lower-alkyl;
(3) unsubstituted naphthyl; and
(4) unsubstituted phenyl if $R^1$ is cycloalkyl and $R^3$ is cycloalkyl.

Furthermore, it is preferred that $R^4$ is thiophenyl substituted with halogen; or phenyl substituted with carbamoyl or halogen.

More preferably, $R^4$ is 5-chloro-thiophen-2-yl, 2-aminocarbonyl-phenyl or 4-chloro-phenyl. Each of these options above individually constitutes a preferred embodiment.

Other preferred compounds of formula (I) as described above are those, wherein $R^5$, $R^6$, $R^7$ and $R^8$ independently from each other are selected from the group consisting of hydrogen, halogen, lower-alkyl, and lower-alkoxy; or alternatively, $R^6$ and $R^7$ are bound together to form a 6-membered aromatic carbocyclic ring together with the carbon atoms to which they are attached. More preferred are compounds of formula (I) wherein $R^5$, $R^6$, $R^7$ and $R^8$ independently from each other are selected from the group consisting of hydrogen, halogen, and lower-alkyl; or alternatively $R^6$ and $R^7$ are bound together to form a 6-membered aromatic carbocyclic ring together with the carbon atoms to which they are attached. Preferably, $R^5$ is hydrogen. Furthermore, it is preferred that $R^6$ is hydrogen, fluoro or methyl, more preferably hydrogen or methyl. Furthermore, it is preferred that $R^7$ is hydrogen, fluoro or chloro, more preferably hydrogen. Furthermore, it is preferred that $R^8$ is hydrogen.

In particular, preferred compounds are the compounds of formula (I) described in the examples as individual compounds as well as pharmaceutically acceptable salts and pharmaceutically acceptable esters thereof.

Preferred compounds of formula (I) are those selected from the group consisting of:
2,N-dicyclohexyl-2-(2-phenyl-benzoimidazol-1-yl)-acetamide hydrogen chloride,
2-[2-(4-chloro-phenyl)-benzoimidazol-1-yl]-4-methyl-pentanoic acid cyclohexylamide,
4-{1-[cyclohexyl-(4-morpholin-4-yl-phenylcarbamoyl)-methyl]-1H-benzoimidazol-2-yl}-benzoic acid methyl ester hydrochloride,
2,N-dicyclohexyl-2-[5,6-dichloro-2-(2,4-dimethoxy-phenyl)-benzoimidazol-1-yl]-acetamide,
2-cyclohexyl-2-[2-(2,4-dimethoxy-phenyl)-benzoimidazol-1-yl]-N-isopropyl-acetamide hydrogen chloride,
2,N-dicyclohexyl-2-[2-(4-methoxy-phenyl)-benzoimidazol-1-yl]-acetamide hydrogen chloride,
2,N-dicyclohexyl-2-[2-(3-methoxy-phenyl)-benzoimidazol-1-yl]-acetamide hydrogen chloride,
2,N-dicyclohexyl-2-[2-(2-methoxy-phenyl)-benzoimidazol-1-yl]-acetamide hydrogen chloride,
2,N-dicyclohexyl-2-(2-naphthalen-1-yl-benzoimidazol-1-yl)-acetamide hydrogen chloride,
2,N-dicyclohexyl-2-[2-(3-ethoxy-phenyl)-benzoimidazol-1-yl]-acetamide hydrogen chloride,
N-cyclohexyl-2-[2-(2,4-dimethoxy-phenyl)-benzoimidazol-1-yl]-4-phenyl-butyramide,
N-cyclohexyl-2-[2-(2,4-dimethoxy-phenyl)-benzoimidazol-1-yl]-3-methyl-butyramide hydrogen chloride,
N-cyclohexyl-2-[2-(2,4-dimethoxy-phenyl)-benzoimidazol-1-yl]-3-phenyl-propionamide hydrogen chloride,
N-cyclohexyl-2-[2-(2,4-dimethoxy-phenyl)-benzoimidazol-1-yl]-2-pyridin-2-yl-acetamide hydrogen chloride,
N-cyclohexyl-2-cyclopentyl-2-[2-(2,4-dimethoxy-phenyl)-benzoimidazol-1-yl]-acetamide hydrogen chloride,
4-{1-[cyclohexyl-(cyclohexylcarbamoyl-methyl)]-1H-benzoimidazol-2-yl}-benzoic acid methyl ester,
2,N-dicyclohexyl-2-(2-naphthalen-2-yl-benzoimidazol-1-yl)-acetamide,
2,N-dicyclohexyl-2-[2-(3-thiophen-2-yl-phenyl)-benzoimidazol-1-yl]-acetamide,
2,N-dicyclohexyl-2-[2-(5-phenyl-thiophen-2-yl)-benzoimidazol-1-yl]-acetamide,
3-{1-[cyclohexyl-(cyclohexylcarbamoyl-methyl)]-1H-benzoimidazol-2-yl}-benzoic acid methyl ester,
2-[2-(3-hydroxy-phenyl)-benzoimidazol-1-yl]-4-methyl-pentanoic acid cyclohexylamide,
2-[2-(4-hydroxymethyl-phenyl)-benzoimidazol-1-yl]-4-methyl-pentanoic acid cyclohexylamide,
2-[2-(1H-indol-5-yl)-benzoimidazol-1-yl]-4-methyl-pentanoic acid cyclohexylamide,
2-[2-(1H-indol-6-yl)-benzoimidazol-1-yl]-4-methyl-pentanoic acid cyclohexylamide,
2-[2-(4-amino-phenyl)-benzoimidazol-1-yl]-4-methyl-pentanoic acid cyclohexylamide,
2-cyclohexyl-2-[2-(2,4-dimethoxy-phenyl)-benzoimidazol-1-yl]-N—((R)1-phenyl-ethyl)-acetamide,
2,N-dicyclohexyl-2-[2-(4-hydroxymethyl-phenyl)-benzoimidazol-1-yl]-acetamide,
N-cyclohexyl-2-[2-(2,3-dimethoxy-phenyl)-benzoimidazol-1-yl]-4-phenyl-butyramide,
2-[2-(3-cyano-phenyl)-benzoimidazol-1-yl]-2,N-dicyclohexyl-acetamide,
2,N-dicyclohexyl-2-{2-[4-(1H-tetrazol-5-yl)-phenyl]-benzoimidazol-1-yl}-acetamide hydrogen chloride,
3-[1-(benzylcarbamoyl-cyclopentyl-methyl)-1H-benzoimidazol-2-yl]-benzoic acid methyl ester,
2-[2-(2,4-dimethoxy-phenyl)-benzoimidazol-1-yl]-hexanoic acid cyclohexylamide,
2,N-dicyclohexyl-2-[2-(3-methanesulfonyl-phenyl)-benzoimidazol-1-yl]-acetamide hydrogen chloride,
N-benzyl-2-cyclohexyl-2-[2-(2,4-dimethoxy-phenyl)-benzoimidazol-1-yl]-acetamide,
2-cyclohexyl-2-[2-(2,4-dimethoxy-phenyl)-benzoimidazol-1-yl]-N-(1-methyl-butyl)-acetamide,
4-[1-(benzylcarbamoyl-cyclopentyl-methyl)-1H-benzoimidazol-2-yl]-benzoic acid methyl ester,
N-cyclopentyl-2-[2-(3-methoxy-phenyl)-benzoimidazol-1-yl]-4-phenyl-butyramide hydrogen chloride,
2,N-dicyclohexyl-2-[2-(2,4-dimethoxy-phenyl)-5-methyl-benzoimidazol-1-yl]-acetamide hydrogen chloride,
2-[2-(4-chloro-phenyl)-benzoimidazol-1-yl]-2,N-dicyclopentyl-acetamide hydrogen chloride,
N-benzhydryl-2-cyclohexyl-2-[2-(2,4-dimethoxy-phenyl)-benzoimidazol-1-yl]-acetamide,
N-benzyl-2-(2-naphthalen-1-yl-benzoimidazol-1-yl)-4-phenyl-butyramide,
2-cyclohexyl-2-[2-(2,4-dimethoxy-phenyl)-benzoimidazol-1-yl]-N-(4-methoxy-phenyl)-acetamide,
2,N-dicyclohexyl-2-[2-(2,4-dimethoxy-phenyl)-4-methyl-benzoimidazol-1-yl]-acetamide,
2,N-dicyclohexyl-2-{2-[3-(2-oxo-pyrrolidin-1-yl)-phenyl]-benzoimidazol-1-yl}-acetamide hydrogen chloride,
2,N-dicyclohexyl-2-[2-(2-oxo-1,2-dihydro-pyridin-4-yl)-benzoimidazol-1-yl]-acetamide,
N-cyclopentyl-2-[2-(2-methoxy-phenyl)-benzoimidazol-1-yl]-4-phenyl-butyramide,
2-cyclohexyl-2-[2-(2,4-dimethoxy-phenyl)-benzoimidazol-1-yl]-N-pentyl-acetamide,
N-benzyl-2-[2-(4-chloro-phenyl)-benzoimidazol-1-yl]-2-cyclopentyl-acetamide hydrogen chloride,
2,N-dicyclopentyl-2-(2-naphthalene-1-yl-benzoimidazol-1-yl)-acetamide,
2-[2-(3-cyano-phenyl)-benzoimidazol-1-yl]-N-cyclohexyl-4-phenyl-butyramide,
2-[2-(4-hydroxy-phenyl)-benzoimidazol-1-yl]-4-methyl-pentanoic acid cyclohexylamide hydrogen chloride,
N-tert-butyl-2-cyclohexyl-2-[2-(2,4-dimethoxy-phenyl)-benzoimidazol-1-yl]-acetamide,
4-[1-(1-benzylcarbamoyl-3-phenyl-propyl)-1H-benzoimidazol-2-yl]-benzoic acid methyl ester,
4-[1-(1-cyclohexylcarbamoyl-3-phenyl-propyl)-1H-benzoimidazol-2-yl]-benzoic acid methyl ester,
2,N-dicyclopentyl-2-[2-(2-methoxy-phenyl)-benzoimidazol-1-yl]-acetamide,
2,N-dicyclohexyl-2-[2-(2,4-dimethoxy-phenyl)-naphtho[2,3-d]imidazol-1-yl]-acetamide,
2-[2-(2,3-dimethoxy-phenyl)-benzoimidazol-1-yl]-4-methyl-pentanoic acid cyclohexylamide,
N-benzyl-2-[2-(2-methoxy-phenyl)-benzoimidazol-1-yl]-4-phenyl-butyramide,
2-cyclohexyl-2-[2-(2,4-dimethoxy-phenyl)-benzoimidazol-1-yl]-N-(3-isopropoxy-propyl)-acetamide,
2-[2-(2,4-dimethoxy-phenyl)-benzoimidazol-1-yl]-N-isopropyl-4-phenyl-butyramide,
N-benzyl-2-cyclopentyl-2-(2-naphthalen-1-yl-benzoimidazol-1-yl)-acetamide,
2,N-dicyclohexyl-2-[2-(2,3-dimethoxy-phenyl)-benzoimidazol-1-yl]-acetamide,
2-[2-(2,4-dimethoxy-phenyl)-benzoimidazol-1-yl]-4-methyl-pentanoic acid cyclohexylamide, 2-cyclohexyl-2-[2-(2,3-dimethoxy-phenyl)-benzoimidazol-1-yl]-N-isopropyl-acetamide,
2-[2-(2,3-dimethoxy-phenyl)-benzoimidazol-1-yl]-N-isopropyl-4-phenyl-butyramide,
2-[2-(4-Acetyl-phenyl)-benzoimidazol-1-yl]-N-cyclohexyl-4-phenyl-butyramide,
N-benzyl-2-[2-(4-chloro-phenyl)-benzoimidazol-1-yl]-4-phenyl-butyramide hydrogen chloride,
4-[1-(1-isopropylcarbamoyl-pentyl)-1H-benzoimidazol-2-yl]-benzoic acid methyl ester,
N-butyl-2-[2-(2,4-dimethoxy-phenyl)-benzoimidazol-1-yl]-2-phenyl-acetamide,
2-[2-(2,3-dimethoxy-phenyl)-benzoimidazol-1-yl]-4-methyl-pentanoic acid isopropylamide,
2-benzo[1,3]dioxol-5-yl-N-butyl-2-[2-(2,3-dimethoxy-phenyl)-benzoimidazol-1-yl]-acetamide,
2-benzo[1,3]dioxol-5-yl-N-butyl-2-[2-(2,4-dimethoxy-phenyl)-benzoimidazol-1-yl]-acetamide,
N-butyl-2-[2-(2,4-dimethoxy-phenyl)-benzoimidazol-1-yl]-2-(2-fluoro-phenyl)-acetamide,
N-cyclopentyl-2-[2-(3-hydroxy-phenyl)-benzoimidazol-1-yl]-4-phenyl-butyramide,
2-[2-(4-acetyl-phenyl)-benzoimidazol-1-yl]-hexanoic acid isopropylamide,
N-butyl-2-[2-(2,3-dimethoxy-phenyl)-benzoimidazol-1-yl]-2-phenyl-acetamide,
2-[2-(4-acetyl-phenyl)-benzoimidazol-1-yl]-4-methyl-pentanoic acid cyclohexylamide,
N-butyl-2-[2-(2,3-dimethoxy-phenyl)-benzoimidazol-1-yl]-2-o-tolyl-acetamide,
N-butyl-2-[2-(2,3-dimethoxy-phenyl)-benzoimidazol-1-yl]-2-(4-methoxy-phenyl)-acetamide,
N-butyl-2-[2-(2,3-dimethoxy-phenyl)-benzoimidazol-1-yl]-2-(2-fluoro-phenyl)-acetamide,
N-butyl-2-[2-(2,3-dimethoxy-phenyl)-benzoimidazol-1-yl]-2-(4-dimethylamino-phenyl)-acetamide,
2-[2-(2,3-dimethoxy-phenyl)-benzoimidazol-1-yl]-hexanoic acid isopropylamide,
4-{1-[(2-fluoro-phenyl)-isopropylcarbamoyl-methyl]-1H-benzoimidazol-2-yl}-benzoic acid methyl ester,
2-[2-(3-cyano-phenyl)-benzoimidazol-1-yl]-4-methyl-pentanoic acid cyclohexylamide,
2-[2-(3-chloro-phenyl)-benzoimidazol-1-yl]-4-methyl-pentanoic acid cyclohexylamide,
N-butyl-2-[2-(2,4-dimethoxy-phenyl)-benzoimidazol-1-yl]-2-(4-methoxy-phenyl)-acetamide,
N-benzyl-2-[2-(3-methoxy-phenyl)-benzoimidazol-1-yl]-4-phenyl-butyramide hydrogen chloride,
2-(4-chloro-phenyl)-2-[2-(2,3-dimethoxy-phenyl)-benzoimidazol-1-yl]-N-isopropyl-acetamide,
N-butyl-2-[2-(2,4-dimethoxy-phenyl)-benzoimidazol-1-yl]-2-(4-dimethylamino-phenyl)-acetamide,
2-[2-(4-hydroxy-phenyl)-benzoimidazol-1-yl]-N-isopropyl-4-phenyl-butyramide,
2-[2-(4-hydroxy-phenyl)-benzoimidazol-1-yl]-4-methyl-pentanoic acid cyclohexylamide,
2-[2-(3-chloro-phenyl)-benzoimidazol-1-yl]-N-isopropyl-4-phenyl-butyramide,
N-butyl-2-(4-chloro-phenyl)-2-[2-(2,4-dimethoxy-phenyl)-benzoimidazol-1-yl]-acetamide,
2-[2-(3-cyano-phenyl)-benzoimidazol-1-yl]-N-isopropyl-4-phenyl-butyramide,
2-[2-(4-acetyl-phenyl)-benzoimidazol-1-yl]-N-isopropyl-2-(4-methoxy-phenyl)acetamide,
4-{1-[isopropylcarbamoyl-(4-methoxy-phenyl)-methyl]-1H-benzoimidazol-2-yl}-benzoic acid methyl ester,
4-[1-(isopropylcarbamoyl-phenyl-methyl)-1H-benzoimidazol-2-yl]-benzoic acid methyl ester,
N-isopropyl-2-[2-(1-methyl-1H-pyrrol-2-yl)-benzoimidazol-1-yl]-4-phenyl-butyramide,
2-[2-(3-cyano-phenyl)-benzoimidazol-1-yl]-hexanoic acid isopropylamide,
2-[2-(4-hydroxy-phenyl)-benzoimidazol-1-yl]-pentanoic acid isopropylamide,
2-benzo[1,3]dioxol-5-yl-N-butyl-2-[2-(1-methyl-1H-pyrrol-2-yl)-benzoimidazol-1-yl]-acetamide,
2-cyclohexyl-2-[2-(2,4-dimethoxy-phenyl)-benzoimidazol-1-yl]-N-(2,6-dimethyl-phenyl)-acetamide,
2,N-dicyclohexyl-2-[2-(2,4-dimethoxy-phenyl)-benzoimidazol-1-yl]-acetamide,
2-cyclohex-3-enyl-N-cyclohexyl-2-[2-(2,4-dimethoxy-phenyl)-benzoimidazol-1-yl]-acetamide,
2-[2-(4-cyano-phenyl)-benzoimidazol-1-yl]-2,N-dicyclohexyl-acetamide hydrogen chloride,
2-cyclohexyl-N-cyclopentyl-2-[2-(2,4-dimethoxy-phenyl)-benzoimidazol-1-yl]-acetamide,
2,N-dicyclohexyl-2-[2-(2,4-dimethoxy-phenyl)-5,6-difluoro-benzoimidazol-1-yl]-acetamide,
2,N-dicyclohexyl-2-[2-(2,4-dimethoxy-phenyl)-6-methyl-benzoimidazol-1-yl]-acetamide,
2-[2-(4-chloro-phenyl)-benzoimidazol-1-yl]-2,N-dicyclohexyl-acetamide,
2,N-dicyclohexyl-2-[2-(4-sulfamoyl-phenyl)-benzoimidazol-1-yl]-acetamide hydrogen chloride,
2-cyclohexyl-2-[2-(2,4-dimethoxy-phenyl)-benzoimidazol-1-yl]-N-(1,1,3,3-tetramethyl-butyl)-acetamide,
4-{[1-cyclopentyl-(cyclopentylcarbamoyl-methyl)]-1H-benzoimidazol-2-yl}-benzoic acid methyl ester hydrogen chloride,
2,N-dicyclohexyl-2-(2-quinolin-6-yl-benzoimidazol-1-yl)-acetamide hydrogen chloride,
2-[2-(4-amino-phenyl)-benzoimidazol-1-yl]-2,N-dicyclohexyl-acetamide,
2-[2-(2,4-dimethoxy-phenyl)-benzoimidazol-1-yl]-5-phenyl-pentanoic acid cyclohexylamide hydrogen chloride,
4-[1-(1-cyclopentylcarbamoyl-3-phenyl-propyl)-1H-benzoimidazol-2-yl]-benzoic acid methyl ester,
2,N-dicyclohexyl-2-[2-(4-dimethylsulfamoyl-phenyl)-benzoimidazol-1-yl]-acetamide hydrogen chloride,
2,N-dicyclohexyl-2-[2-(3-sulfamoyl-phenyl)-benzoimidazol-1-yl]-acetamide hydrogen chloride,
2,N-dicyclohexyl-2-{2-[3-(1H-tetrazol-5-yl)-phenyl]-benzoimidazol-1-yl}-acetamide hydrogen chloride,
2,N-dicyclohexyl-2-{2-[4-(1H-imidazol-2-yl)-phenyl]-benzoimidazol-1-yl}-acetamide hydrogen chloride,
2,N-dicyclohexyl-2-[2-(4-imidazol-1-yl-phenyl)-benzoimidazol-1-yl]-acetamide hydrogen chloride,
2,N-dicyclohexyl-2-[2-(4-[1,2,4]triazol-4-yl-phenyl)-benzoimidazol-1-yl]-acetamide hydrogen chloride,
2,N-dicyclohexyl-2-{2-[4-(1H-pyrazol-4-yl)-phenyl]-benzoimidazol-1-yl}-acetamide hydrogen chloride,
2,N-dicyclohexyl-2-[2-(4-[1,2,3]thiadiazol-4-yl-phenyl)-benzoimidazol-1-yl]-acetamide hydrogen chloride,
2,N-dicyclohexyl-2-[2-(1,3-dioxo-2,3-dihydro-1H-isoindol-5-yl)-benzoimidazol-1-yl]-acetamide hydrogen chloride,
2,N-dicyclohexyl-2-[2-(3-tetrazol-1-yl-phenyl)-benzoimidazol-1-yl]-acetamide hydrogen chloride,
4-[1-(cyclohexyl-3-methoxycarbonylphenylcarbamoyl-methyl)-1H-benzoimidazol-2-yl]-benzoic acid methyl ester hydrogen chloride, trans 4-(1-{cyclohexyl-[(4-methoxycarbonyl-cyclohexylmethyl)-carbamoyl]-methyl}-1H-benzoimidazol-2-yl)-benzoic acid methyl ester hydrogen chloride, 4-{2-cyclohexyl-2-[2-(4-methoxycarbonyl-phenyl)-benzoimidazol-1-yl]-acetylamino}-piperidine-1-carboxylic acid ethyl ester hydrogen chloride,
N-cyclohexyl-2-[2-(2,4-dimethoxy-phenyl)-benzoimidazol-1-yl]-2-phenyl-acetamide hydrogen chloride,
4-(1-{cyclohexyl-[3-(2-oxo-pyrrolidin-1-yl)-propylcarbamoyl]-methyl}-1H-benzoimidazol-2-yl)-benzoic acid methyl ester hydrogen chloride,
4-{1-[cyclohexyl-(3-methoxycarbonyl-propylcarbamoyl)-methyl]-1H-benzoimidazol-2-yl}-benzoic acid methyl ester hydrogen chloride,
4-{1-[cyclohexyl-(4-methoxycarbonyl-butylcarbamoyl)-methyl]-1H-benzoimidazol-2-yl}-benzoic acid methyl ester hydrogen chloride,
4-{1-[cyclohexyl-(5-methoxycarbonyl-pentylcarbamoyl)-methyl]-1H-benzoimidazol-2-yl}-benzoic acid methyl ester hydrogen chloride,
2-cyclohexyl-2-[2-(2,4-dimethoxy-phenyl)-benzoimidazol-1-yl]-N-methyl-acetamide hydrogen chloride,
2-[2-(4-Acetylamino-phenyl)-benzoimidazol-1-yl]-2,N-dicyclohexyl-acetamide,
2-[2-(3-acetylamino-phenyl)-benzoimidazol-1-yl]-2,N-dicyclohexyl-acetamide,
4-{1-[cyclohexyl-(3-formylamino-phenylcarbamoyl)-methyl]-1H-benzoimidazol-2-yl}-benzoic acid methyl ester hydrogen chloride,
N-cyclopentyl-2-(2-naphthalen-1-yl-benzoimidazol-1-yl)-propionamide, and any pharmaceutically acceptable salt or ester thereof.

Particularly preferred compounds of formula (I) are those selected from the group consisting of:
N-cyclohexyl-2-[2-(2,4-dimethoxy-phenyl)-benzoimidazol-1-yl]-2-pyridin-2-yl-acetamide hydrogen chloride,
N-cyclohexyl-2-cyclopentyl-2-[2-(2,4-dimethoxy-phenyl)-benzoimidazol-1-yl]-acetamide hydrogen chloride,
2,N-dicyclohexyl-2-(2-naphthalen-2-yl-benzoimidazol-1-yl)-acetamide,
2,N-dicyclohexyl-2-[2-(5-phenyl-thiophen-2-yl)-benzoimidazol-1-yl]-acetamide,
2,N-dicyclohexyl-2-[2-(4-hydroxymethyl-phenyl)-benzoimidazol-1-yl]-acetamide,
2,N-dicyclohexyl-2-{2-[4-(1H-tetrazol-5-yl)-phenyl]-benzoimidazol-1-yl}-acetamide hydrogen chloride,
2,N-dicyclohexyl-2-[2-(2,4-dimethoxy-phenyl)-5-methyl-benzoimidazol-1-yl]-acetamide hydrogen chloride,
2,N-dicyclohexyl-2-[2-(2-oxo-1,2-dihydro-pyridin-4-yl)-benzoimidazol-1-yl]-acetamide,
2-cyclohexyl-2-[2-(2,4-dimethoxy-phenyl)-benzoimidazol-1-yl]-N-(2,6-dimethyl-phenyl)-acetamide,
2-cyclohexyl-N-cyclopentyl-2-[2-(2,4-dimethoxy-phenyl)-benzoimidazol-1-yl]-acetamide,
2-cyclohexyl-2-[2-(2,4-dimethoxy-phenyl)-benzoimidazol-1-yl]-N-(1,1,3,3-tetramethyl-butyl)-acetamide,
2,N-dicyclohexyl-2-(2-quinolin-6-yl-benzoimidazol-1-yl)-acetamide hydrogen chloride,
2-[2-(2,4-dimethoxy-phenyl)-benzoimidazol-1-yl]-5-phenyl-pentanoic acid cyclohexylamide hydrogen chloride,
2,N-dicyclohexyl-2-{2-[4-(1H-imidazol-2-yl)-phenyl]-benzoimidazol-1-yl}-acetamide hydrogen chloride,
N-cyclohexyl-2-[2-(2,4-dimethoxy-phenyl)-benzoimidazol-1-yl]-2-phenyl-acetamide hydrogen chloride,
2-[2-(4-Acetylamino-phenyl)-benzoimidazol-1-yl]-2,N-dicyclohexyl-acetamide, and any pharmaceutically acceptable salt or ester thereof.

Other preferred compounds of formula (I) are those selected from the group consisting of
2,N-Dicyclohexyl-2-(2-phenyl-benzoimidazol-1-yl)-acetamide,
2-[1-(Cyclohexyl-cyclohexylcarbamoyl-methyl)-1H-benzoimidazol-2-yl]-benzamide,
2-[2-(5-Amino-pyridin-2-yl)-benzoimidazol-1-yl]-2,N-dicyclohexyl-acetamide,
2,N-Dicyclohexyl-2-[2-(2-ethyl-5-methyl-2H-pyrazol-3-yl)-benzoimidazol-1-yl]-acetamide,
2,N-Dicyclohexyl-2-[2-(5-methyl-isoxazol-4-yl)-benzoimidazol-1-yl]-acetamide,
2,N-Dicyclohexyl-2-[2-(1H-pyrrol-2-yl)-benzoimidazol-1-yl]-acetamide,
2-(1'H-[2,5']Bibenzoimidazolyl-1-yl)-2,N-dicyclohexyl-acetamide,
2,N-Dicyclohexyl-2-(2-furan-2-yl-benzoimidazol-1-yl)-acetamide,
2-[6-Bromo-2-(4-chloro-phenyl)-benzoimidazol-1-yl]-2,N-dicyclohexyl-acetamide,
2-[6-Chloro-2-(4-chloro-phenyl)-benzoimidazol-1-yl]-2,N-dicyclohexyl-acetamide,
2-[2-(4-Chloro-phenyl)-6-methoxy-benzoimidazol-1-yl]-2,N-dicyclohexyl-acetamide,
2-[6-Chloro-2-(4-chloro-phenyl)-5-fluoro-benzoimidazol-1-yl]-2,N-dicyclohexyl-acetamide,
(S)-2,N-Dicyclohexyl-2-[2-(2,4-dimethoxy-phenyl)-benzoimidazol-1-yl]-acetamide,
(S)-2-[2-(4-Chloro-phenyl)-benzoimidazol-1-yl]-2,N-dicyclohexyl-acetamide,
2-[1-(Cyclohexyl-cyclohexylcarbamoyl-methyl)-1H-benzoimidazol-2-yl]-N-methyl-benzamide,
2,N-Dicyclohexyl-2-(2-furan-3-yl-benzoimidazol-1-yl)-acetamide,
2,N-Dicyclohexyl-2-[2-(3-methyl-furan-2-yl)-benzoimidazol-1-yl]-acetamide,
2,N-Dicyclohexyl-2-[2-(3-methyl-isoxazol-5-yl)-benzoimidazol-1-yl]-acetamide,
2,N-Dicyclohexyl-2-(2-m-tolyl-benzoimidazol-1-yl)-acetamide,
2,N-Dicyclohexyl-2-[2-(3-fluoro-phenyl)-benzoimidazol-1-yl]-acetamide,
2,N-Dicyclohexyl-2-[2-(2-fluoro-phenyl)-benzoimidazol-1-yl]-acetamide,
2,N-Dicyclohexyl-2-[2-(3,5-dimethyl-isoxazol-4-yl)-benzoimidazol-1-yl]-acetamide,
2,N-Dicyclohexyl-2-[2-(3-methyl-thiophen-2-yl)-benzoimidazol-1-yl]-acetamide,
2,N-Dicyclohexyl-2-[2-(4-vinyl-phenyl)-benzoimidazol-1-yl]-acetamide,
2,N-Dicyclohexyl-2-[2-(2,3-dimethyl-phenyl)-benzoimidazol-1-yl]-acetamide,
2,N-Dicyclohexyl-2-[2-(3,4-dimethyl-phenyl)-benzoimidazol-1-yl]-acetamide,
2,N-Dicyclohexyl-2-[2-(4-ethyl-phenyl)-benzoimidazol-1-yl]-acetamide,
2,N-Dicyclohexyl-2-[2-(2,4-dimethyl-phenyl)-benzoimidazol-1-yl]-acetamide,
2,N-Dicyclohexyl-2-[2-(2-ethyl-phenyl)-benzoimidazol-1-yl]-acetamide,
2,N-Dicyclohexyl-2-[2-(4-fluoro-3-methyl-phenyl)-benzoimidazol-1-yl]-acetamide,
2,N-Dicyclohexyl-2-[2-(3-fluoro-4-methyl-phenyl)-benzoimidazol-1-yl]-acetamide,
2,N-Dicyclohexyl-2-[2-(2,6-difluoro-phenyl)-benzoimidazol-1-yl]-acetamide, 2,N-Dicyclohexyl-2-[2-(3,5-difluoro-phenyl)-benzoimidazol-1-yl]-acetamide,
2,N-Dicyclohexyl-2-[2-(2,5-difluoro-phenyl)-benzoimidazol-1-yl]-acetamide,
2,N-Dicyclohexyl-2-[2-(3,4-difluoro-phenyl)-benzoimidazol-1-yl]-acetamide,
2,N-Dicyclohexyl-2-[2-(2,3-difluoro-phenyl)-benzoimidazol-1-yl]-acetamide,
2,N-Dicyclohexyl-2-[2-(1H-indol-4-yl)-benzoimidazol-1-yl]-acetamide,
2,N-Dicyclohexyl-2-[2-(1H-indol-6-yl)-benzoimidazol-1-yl]-acetamide,
2-[2-(5-Chloro-thiophen-2-yl)-benzoimidazol-1-yl]-2,N-dicyclohexyl-acetamide,
2-[2-(4-Acetyl-phenyl)-benzoimidazol-1-yl]-2,N-dicyclohexyl-acetamide,
2-[2-(2-Acetyl-phenyl)-benzoimidazol-1-yl]-2,N-dicyclohexyl-acetamide,
2,N-Dicyclohexyl-2-[2-(4-isopropyl-phenyl)-benzoimidazol-1-yl]-acetamide,
2-[2-(4-Cyano-2-fluoro-phenyl)-benzoimidazol-1-yl]-2,N-dicyclohexyl-acetamide,
2,N-Dicyclohexyl-2-[2-(2-dimethylamino-phenyl)-benzoimidazol-1-yl]-acetamide,
2,N-Dicyclohexyl-2-[2-(3-dimethylamino-phenyl)-benzoimidazol-1-yl]-acetamide,
2,N-Dicyclohexyl-2-[2-(4-methoxy-3-methyl-phenyl)-benzoimidazol-1-yl]-acetamide,
2,N-Dicyclohexyl-2-[2-(4-methoxy-2-methyl-phenyl)-benzoimidazol-1-yl]-acetamide,
2,N-Dicyclohexyl-2-[2-(3-methoxy-4-methyl-phenyl)-benzoimidazol-1-yl]-acetamide,
2,N-Dicyclohexyl-2-[2-(2-ethoxy-phenyl)-benzoimidazol-1-yl]-acetamide,
2-[2-(6-Chloro-pyridin-3-yl)-benzoimidazol-1-yl]-2,N-dicyclohexyl-acetamide,
2-[2-(2-Chloro-pyridin-4-yl)-benzoimidazol-1-yl]-2,N-dicyclohexyl-acetamide,
2-[2-(4-Chloro-phenyl)-6-fluoro-benzoimidazol-1-yl]-2,N-dicyclohexyl-acetamide,
2,N-Dicyclohexyl-2-[2-(3-fluoro-4-methoxy-phenyl)-benzoimidazol-1-yl]-acetamide,
2-[2-(4-Chloro-3-methyl-phenyl)-benzoimidazol-1-yl]-2,N-dicyclohexyl-acetamide,
2-[2-(3-Chloro-2-methyl-phenyl)-benzoimidazol-1-yl]-2,N-dicyclohexyl-acetamide,
2-[2-(4-Chloro-3-fluoro-phenyl)-benzoimidazol-1-yl]-2,N-dicyclohexyl-acetamide,
2-[2-(3-Chloro-4-fluoro-phenyl)-benzoimidazol-1-yl]-2,N-dicyclohexyl-acetamide,
2,N-Dicyclohexyl-2-[2-(5-methyl-1H-indol-2-yl)-benzoimidazol-1-yl]-acetamide,
2,N-Dicyclohexyl-2-[2-(2,3,4-trifluoro-phenyl)-benzoimidazol-1-yl]-acetamide,
2,N-Dicyclohexyl-2-[2-(2,4,5-trifluoro-phenyl)-benzoimidazol-1-yl]-acetamide,
2-(2-Benzo[b]thiophen-2-yl-benzoimidazol-1-yl)-2,N-dicyclohexyl-acetamide,
2,N-Dicyclohexyl-2-[2-(5-fluoro-1H-indol-2-yl)-benzoimidazol-1-yl]-acetamide,
2-(2-Benzothiazol-6-yl-benzoimidazol-1-yl)-2,N-dicyclohexyl-acetamide,
2,N-Dicyclohexyl-2-[2-(4-isopropoxy-phenyl)-benzoimidazol-1-yl]-acetamide,
2,N-Dicyclohexyl-2-[2-(3,4-dimethoxy-phenyl)-benzoimidazol-1-yl]-acetamide,
2,N-Dicyclohexyl-2-[2-(2,5-dimethoxy-phenyl)-benzoimidazol-1-yl]-acetamide,
2,N-Dicyclohexyl-2-[2-(2-difluoromethoxy-phenyl)-benzoimidazol-1-yl]-acetamide,
2,N-Dicyclohexyl-2-[2-(4-difluoromethoxy-phenyl)-benzoimidazol-1-yl]-acetamide,
2,N-Dicyclohexyl-2-[2-(3-difluoromethoxy-phenyl)-benzoimidazol-1-yl]-acetamide,
2,N-Dicyclohexyl-2-[2-(4-trifluoromethyl-phenyl)-benzoimidazol-1-yl]-acetamide,
2,N-Dicyclohexyl-2-[2-(3,4-dichloro-phenyl)-benzoimidazol-1-yl]-acetamide,
2-[2-(4-Bromo-phenyl)-benzoimidazol-1-yl]-2,N-dicyclohexyl-acetamide,
2,N-Dicyclohexyl-2-[2-(6-methoxy-naphthalen-2-yl)-benzoimidazol-1-yl]-acetamide,
2,N-Dicyclohexyl-2-[2-(3-trifluoromethoxy-phenyl)-benzoimidazol-1-yl]-acetamide,
2,N-Dicyclohexyl-2-[2-(7-ethoxy-benzofuran-2-yl)-benzoimidazol-1-yl]-acetamide,
2,N-Dicyclohexyl-2-[2-(3-fluoro-4-trifluoromethyl-phenyl)-benzoimidazol-1-yl]-acetamide,
2,N-Dicyclohexyl-2-[2-(6-diethylamino-pyridin-3-yl)-benzoimidazol-1-yl]-acetamide,
2-[2-(2-Chloro-5-methyl-phenyl)-benzoimidazol-1-yl]-2,N-dicyclohexyl-acetamide,
2-[2-(5-Chloro-2-methyl-phenyl)-benzoimidazol-1-yl]-2,N-dicyclohexyl-acetamide,
2-[2-(2-Chloro-6-methyl-phenyl)-benzoimidazol-1-yl]-2,N-dicyclohexyl-acetamide,
2,N-Dicyclohexyl-2-(2-quinoxalin-6-yl-benzoimidazol-1-yl)-acetamide,
2-[2-(5-Chloro-2-fluoro-phenyl)-benzoimidazol-1-yl]-2,N-dicyclohexyl-acetamide,
2,N-Dicyclohexyl-2-[2-(4-methoxy-3,5-dimethyl-phenyl)-benzoimidazol-1-yl]-acetamide,
2,N-Dicyclohexyl-2-[2-(2,3-dimethoxy-phenyl)-benzoimidazol-1-yl]-acetamide,
2-[2-(3-Chloro-4-methoxy-phenyl)-benzoimidazol-1-yl]-2,N-dicyclohexyl-acetamide,
2,N-Dicyclohexyl-2-[2-(2,5-dichloro-phenyl)-benzoimidazol-1-yl]-acetamide,
2-[2-(3-Chloro-2,4-difluoro-phenyl)-benzoimidazol-1-yl]-2,N-dicyclohexyl-acetamide,
2-[2-(2-Chloro-4,5-difluoro-phenyl)-benzoimidazol-1-yl]-2,N-dicyclohexyl-acetamide,
2,N-Dicyclohexyl-2-[2-(4-diethylamino-phenyl)-benzoimidazol-1-yl]-acetamide,
2-[2-(4-Benzoyl-phenyl)-benzoimidazol-1-yl]-2,N-dicyclohexyl-acetamide,
(S)-2-[2-(4-Cyano-phenyl)-benzoimidazol-1-yl]-2,N-dicyclohexyl-acetamide,
2,N-Dicyclohexyl-2-[2-(4-phenoxy-phenyl)-benzoimidazol-1-yl]-acetamide,
2,N-Dicyclohexyl-2-[2-(2-phenoxy-phenyl)-benzoimidazol-1-yl]-acetamide,
2,N-Dicyclohexyl-2-[2-(3-phenoxy-phenyl)-benzoimidazol-1-yl]-acetamide,
2,N-Dicyclohexyl-2-{2-[2-(1,1,2,2-tetrafluoro-ethoxy)-phenyl]-benzoimidazol-1-yl}-acetamide,
2,N-Dicyclohexyl-2-{2-[3-(1,1,2,2-tetrafluoro-ethoxy)-phenyl]-benzoimidazol-1-yl}-acetamide,
2,N-Dicyclohexyl-2-{2-[4-(1,1,2,2-tetrafluoro-ethoxy)-phenyl]-benzoimidazol-1-yl}-acetamide,
2,N-Dicyclohexyl-2-[2-(4'-trifluoromethyl-biphenyl-4-yl)-benzoimidazol-1-yl]-acetamide, 2,N-Dicyclohexyl-2-[2-(3',4'-dichloro-biphenyl-4-yl)-benzoimidazol-1-yl]-acetamide,
2,N-Dicyclohexyl-2-[2-(2,4-dichloro-5-sulfamoyl-phenyl)-benzoimidazol-1-yl]-acetamide,
(S)-2-[6-Chloro-2-(4-chloro-phenyl)-5-fluoro-benzoimidazol-1-yl]-2,N-dicyclohexyl-acetamide,
2,N-Dicyclohexyl-2-(2-pyridin-2-yl-benzoimidazol-1-yl)-acetamide,
2,N-Dicyclohexyl-2-[2-(6-methyl-pyridin-3-yl)-benzoimidazol-1-yl]-acetamide,
2,N-Dicyclohexyl-2-[2-(3-methyl-pyridin-2-yl)-benzoimidazol-1-yl]-acetamide,
2,N-Dicyclohexyl-2-[2-(6-methyl-pyridin-2-yl)-benzoimidazol-1-yl]-acetamide,
2-[2-(2-Amino-pyridin-3-yl)-benzoimidazol-1-yl]-2,N-dicyclohexyl-acetamide,
2-[2-(6-Cyano-pyridin-3-yl)-benzoimidazol-1-yl]-2,N-dicyclohexyl-acetamide,
2,N-Dicyclohexyl-2-[2-(2-methoxy-pyridin-3-yl)-benzoimidazol-1-yl]-acetamide,
2-[2-(2-Chloro-6-methyl-pyridin-3-yl)-benzoimidazol-1-yl]-2,N-dicyclohexyl-acetamide,
2-[2-(2-Chloro-6-methyl-pyridin-4-yl)-benzoimidazol-1-yl]-2,N-dicyclohexyl-acetamide,
2,N-Dicyclohexyl-2-(2-quinolin-3-yl-benzoimidazol-1-yl)-acetamide,
2,N-Dicyclohexyl-2-(2-quinolin-4-yl-benzoimidazol-1-yl)-acetamide,
2-[2-(3-Chloro-4-trifluoromethyl-phenyl)-benzoimidazol-1-yl]-2,N-dicyclohexyl-acetamide,
(S)-2-[2-(4-Chloro-phenyl)-benzoimidazol-1-yl]-4-methylpentanoic acid cyclohexylamide,
2-(4-Chloro-phenyl)-2-[2-(4-chloro-phenyl)-benzoimidazol-1-yl]-N-cyclohexyl-acetamide,
2-[2-(4-Chloro-phenyl)-benzoimidazol-1-yl]-N-cyclohexyl-2-(4-trifluoromethyl-phenyl)-acetamide,
2-[2-(4-Chloro-phenyl)-benzoimidazol-1-yl]-N-cyclohexyl-2-(3,4-dichloro-phenyl)-acetamide,
2-[2-(4-Chloro-phenyl)-benzoimidazol-1-yl]-N-cyclohexyl-2-(3-methoxy-phenyl)-acetamide,
2-[2-(4-Chloro-phenyl)-benzoimidazol-1-yl]-N-cyclohexyl-2-p-tolyl-acetamide,
2-[2-(4-Chloro-phenyl)-benzoimidazol-1-yl]-N-cyclohexyl-2-(3-fluoro-phenyl)-acetamide,
2-[2-(4-Chloro-phenyl)-benzoimidazol-1-yl]-N-cyclohexyl-2-(4-difluoromethoxy-phenyl)-acetamide,
2-[2-(4-Chloro-phenyl)-benzoimidazol-1-yl]-N-cyclohexyl-2-(2,5-difluoro-phenyl)-acetamide,
2-[2-(4-Chloro-phenyl)-benzoimidazol-1-yl]-N-cyclohexyl-2-(2-fluoro-5-methoxy-phenyl)-acetamide,
(S)-2-[2-(5-Chloro-2-fluoro-phenyl)-benzoimidazol-1-yl]-2,N-dicyclohexyl-acetamide,
(S)-2,N-Dicyclohexyl-2-[2-(2,3-dimethoxy-phenyl)-benzoimidazol-1-yl]-acetamide,
(S)-2-[2-(3-Chloro-4-methoxy-phenyl)-benzoimidazol-1-yl]-2,N-dicyclohexyl-acetamide,
(S)-2-Cyclohexyl-2-[2-(2,4-dimethoxy-phenyl)-benzoimidazol-1-yl]-N-(2,6-dimethyl-phenyl)-acetamide,
2-[2-(4-Chloro-phenyl)-benzoimidazol-1-yl]-2-cyclohexyl-N-(4,4-difluoro-cyclohexyl)-acetamide,
(S)-2-[2-(4-Chloro-phenyl)-benzoimidazol-1-yl]-2-cyclohexyl-N-(4,4-difluoro-cyclohexyl)-acetamide,
(S)-2-[2-(2-Amino-pyridin-3-yl)-benzoimidazol-1-yl]-2,N-dicyclohexyl-acetamide,
2,N-Dicyclohexyl-2-(6-fluoro-2-pyridin-2-yl-benzoimidazol-1-yl)-acetamide,
2,N-Dicyclohexyl-2-[2-(2,4-dimethoxy-phenyl)-6-fluoro-benzoimidazol-1-yl]-acetamide,
2,N-Dicyclohexyl-2-[6-fluoro-2-(4-methoxy-phenyl)-benzoimidazol-1-yl]-acetamide,
2,N-Dicyclohexyl-2-[2-(2,3-difluoro-phenyl)-6-fluoro-benzoimidazol-1-yl]-acetamide,
2,N-Dicyclohexyl-2-[2-(2,3-dimethoxy-phenyl)-6-fluoro-benzoimidazol-1-yl]-acetamide,
2,N-Dicyclohexyl-2-[2-(2-ethyl-5-methyl-2H-pyrazol-3-yl)-6-fluoro-benzoimidazol-1-yl]-acetamide,
2,N-Dicyclohexyl-2-[2-(3,5-dimethyl-isoxazol-4-yl)-6-fluoro-benzoimidazol-1-yl]-acetamide,
2,N-Dicyclohexyl-2-[6-fluoro-2-(1H-pyrazol-4-yl)-benzoimidazol-1-yl]-acetamide,
2,N-Dicyclohexyl-2-[2-(1,5-dimethyl-1H-pyrazol-3-yl)-6-fluoro-benzoimidazol-1-yl]-acetamide)
2,N-Dicyclohexyl-2-[6-fluoro-2-(3-methyl-isoxazol-5-yl)-benzoimidazol-1-yl]-acetamide)
2,N-Dicyclohexyl-2-[6-fluoro-2-(1H-pyrrol-2-yl)-benzoimidazol-1-yl]-acetamide,
2,N-Dicyclohexyl-2-[6-fluoro-2-(3-methyl-thiophen-2-yl)-benzoimidazol-1-yl]-acetamide,
N-Benzyl-2-[2-(4-chloro-phenyl)-benzoimidazol-1-yl]-2-cyclohexyl-acetamide,
N-Butyl-2-[2-(4-chloro-phenyl)-benzoimidazol-1-yl]-2-cyclohexyl-acetamide,
2-[2-(4-Chloro-phenyl)-benzoimidazol-1-yl]-N-cyclohexyl-2-(tetrahydro-pyran-4-yl)-acetamide,
2-[5-Chloro-2-(4-chloro-phenyl)-6-fluoro-benzoimidazol-1-yl]-2,N-dicyclohexyl-acetamide,
2-[2-(4-Chloro-phenyl)-5,6-difluoro-benzoimidazol-1-yl]-2,N-dicyclohexyl-acetamide,
2-[2-(4-Chloro-phenyl)-benzoimidazol-1-yl]-2-cyclohexyl-N-(tetrahydro-pyran-4-yl)-acetamide,
2-[2-(4-Chloro-phenyl)-benzoimidazol-1-yl]-2-cyclohexyl-N-cyclopropyl-acetamide,
2,N-Dicyclohexyl-2-[2-(6-morpholin-4-yl-pyridin-3-yl)-benzoimidazol-1-yl]-acetamide,
(S)-2-[2-(4-Chloro-phenyl)-benzoimidazol-1-yl]-2-cyclohexyl-N-(tetrahydro-pyran-4-yl)-acetamide,
(S)-2,N-Dicyclohexyl-2-[2-(4-methanesulfonyl-phenyl)-benzoimidazol-1-yl]-acetamide,
(S)-2-[2-(4-Chloro-phenyl)-benzoimidazol-1-yl]-2-cyclohexyl-N-cyclopropyl-acetamide,
2-[6-Chloro-2-(4-chloro-phenyl)-5-fluoro-benzoimidazol-1-yl]-N-cyclohexyl-2-(tetrahydro-pyran-4-yl)-acetamide,
(S)-2-[2-(4-Chloro-phenyl)-benzoimidazol-1-yl]-N-cyclohexyl-2-(tetrahydro-pyran-4-yl)-acetamide,
(S)-2-[6-Chloro-2-(4-chloro-phenyl)-5-fluoro-benzoimidazol-1-yl]-N-cyclohexyl-2-(tetrahydro-pyran-4-yl)-acetamide,
(S)-2-[2-(4-Chloro-phenyl)-5,6-difluoro-benzoimidazol-1-yl]-2,N-dicyclohexyl-acetamide,
(S)-2-[2-(5-Chloro-thiophen-2-yl)-benzoimidazol-1-yl]-2,N-dicyclohexyl-acetamide,
(S)-2,N-Dicyclohexyl-2-[2-(2,3-difluoro-phenyl)-6-fluoro-benzoimidazol-1-yl]-acetamide,
2-[6-Chloro-2-(4-chloro-phenyl)-5-fluoro-benzoimidazol-1-yl]-N-cyclohexyl-2-cyclopentyl-acetamide,
(S)-2-[6-Chloro-2-(4-chloro-phenyl)-5-fluoro-benzoimidazol-1-yl]-heptanoic acid cyclohexylamide,
(S)-2-[6-Chloro-2-(4-chloro-phenyl)-5-fluoro-benzoimidazol-1-yl]-N-cyclohexyl-2-cyclopentyl-acetamide,
2-[2-(4-Chloro-phenyl)-5-fluoro-benzoimidazol-1-yl]-2,N-dicyclohexyl-acetamide,
2-[1-(Cyclohexyl-cyclohexylcarbamoyl-methyl)-5,6-difluoro-1H-benzoimidazol-2-yl]-benzoic acid methyl ester, 2,N-Dicyclohexyl-2-(5,6-difluoro-2-pyridin-2-yl-benzoimidazol-1-yl)-acetamide,
2-[2-(5-Chloro-thiophen-2-yl)-5,6-difluoro-benzoimidazol-1-yl]-2,N-dicyclohexyl-acetamide,
2-[6-Chloro-1-(cyclohexyl-cyclohexylcarbamoyl-methyl)-5-fluoro-1H-benzoimidazol-2-yl]-benzoic acid methyl ester,
2-(6-Chloro-5-fluoro-2-pyridin-2-yl-benzoimidazol-1-yl)-2,N-dicyclohexyl-acetamide,
2-(6-Chloro-5-fluoro-2-pyridin-3-yl-benzoimidazol-1-yl)-2,N-dicyclohexyl-acetamide,
2-(6-Chloro-5-fluoro-2-pyridin-4-yl-benzoimidazol-1-yl)-2,N-dicyclohexyl-acetamide,
2-[6-Chloro-2-(3-chloro-thiophen-2-yl)-5-fluoro-benzoimidazol-1-yl]-2,N-dicyclohexyl-acetamide,
2-[6-Chloro-2-(5-chloro-thiophen-2-yl)-5-fluoro-benzoimidazol-1-yl]-2,N-dicyclohexyl-acetamide,
(S)-2-[6-Chloro-2-(4-chloro-phenyl)-5-fluoro-benzoimidazol-1-yl]-3-ethyl-pentanoic acid cyclohexylamide,
2-[6-Chloro-5-fluoro-2-(4-fluoro-phenyl)-benzoimidazol-1-yl]-2,N-dicyclohexyl-acetamide,
2-[2-(4-Chloro-phenyl)-benzoimidazol-1-yl]-2-cyclohexyl-N-(1-isopropyl-2-methyl-propyl)-acetamide,
2-[6-Chloro-2-(4-chloro-phenyl)-5-fluoro-benzoimidazol-1-yl]-2-cyclohexyl-N-cyclopentyl-acetamide,
2-[2-(4-Chloro-phenyl)-5,6-difluoro-benzoimidazol-1-yl]-N-cyclohexyl-2-(tetrahydro-pyran-4-yl)-acetamide,
(S)-2-[2-(4-Chloro-phenyl)-5-fluoro-benzoimidazol-1-yl]-2,N-dicyclohexyl-acetamide,
2-[2-(4-Chloro-phenyl)-5,6-difluoro-benzoimidazol-1-yl]-2-cyclohexyl-N-(tetrahydro-pyran-4-yl)-acetamide,
2-[6-Chloro-2-(4-chloro-phenyl)-5-fluoro-benzoimidazol-1-yl]-2-cyclohexyl-N-(tetrahydro-pyran-4-yl)-acetamide,
2,N-Dicyclohexyl-2-[2-(3-dimethylamino-phenyl)-5,6-difluoro-benzoimidazol-1-yl]-acetamide,
2,N-Dicyclohexyl-2-[2-(3-dimethylamino-phenyl)-6-fluoro-benzoimidazol-1-yl]-acetamide,
2-[2-(4-Chloro-phenyl)-5,6-difluoro-benzoimidazol-1-yl]-2-cyclohexyl-N-(1-isopropyl-2-methyl-propyl)-acetamide,
2-[6-Chloro-2-(4-chloro-phenyl)-5-fluoro-benzoimidazol-1-yl]-2-cyclohexyl-N-(1-isopropyl-2-methyl-propyl)-acetamide,
2-[2-(3-Chloro-phenyl)-5,6-difluoro-benzoimidazol-1-yl]-2,N-dicyclohexyl-acetamide,
2-[2-(2-Chloro-phenyl)-5,6-difluoro-benzoimidazol-1-yl]-2,N-dicyclohexyl-acetamide,
(S)-2-[6-Chloro-5-fluoro-2-(4-fluoro-phenyl)-benzoimidazol-1-yl]-2,N-dicyclohexyl-acetamide,
(S)-2-[2-(4-Chloro-phenyl)-5,6-difluoro-benzoimidazol-1-yl]-N-cyclohexyl-2-(tetrahydro-pyran-4-yl)-acetamide,
2-[2-(4-Chloro-phenyl)-5-fluoro-benzoimidazol-1-yl]-N-cyclohexyl-2-(tetrahydro-pyran-4-yl)-acetamide,
2-[2-(4-Chloro-phenyl)-6-fluoro-benzoimidazol-1-yl]-N-cyclohexyl-2-(tetrahydro-pyran-4-yl)-acetamide,
2-[2-(4-Chloro-phenyl)-6-fluoro-benzoimidazol-1-yl]-N-cyclohexyl-2-(tetrahydro-pyran-2-yl)-acetamide,
2-[6-Chloro-2-(4-chloro-phenyl)-5-fluoro-benzoimidazol-1-yl]-N-cyclohexyl-2-(tetrahydro-pyran-2-yl)-acetamide,
(S)-2,N-Dicyclohexyl-2-[6-fluoro-2-(3-methyl-thiophen-2-yl)-benzoimidazol-1-yl]-acetamide,
(S)-2-[2-(2-Chloro-phenyl)-5,6-difluoro-benzoimidazol-1-yl]-2,N-dicyclohexyl-acetamide,
(S)-2-[2-(4-Chloro-phenyl)-5-fluoro-benzoimidazol-1-yl]-N-cyclohexyl-2-(tetrahydro-pyran-4-yl)-acetamide,
(S)-2-[2-(4-Chloro-phenyl)-6-fluoro-benzoimidazol-1-yl]-N-cyclohexyl-2-(tetrahydro-pyran-4-yl)-acetamide,
(S)-2-[2-(4-Chloro-phenyl)-6-fluoro-benzoimidazol-1-yl]-N-cyclohexyl-2-(R)-tetrahydro-pyran-2-yl-acetamide,
(S)-2-[2-(4-Chloro-phenyl)-6-fluoro-benzoimidazol-1-yl]-N-cyclohexyl-2-(S)-tetrahydro-pyran-2-yl-acetamide,
2-[2-(4-Chloro-phenyl)-5-fluoro-benzoimidazol-1-yl]-N-cyclohexyl-2-(tetrahydro-pyran-2-yl)-acetamide,
2,N-Dicyclohexyl-2-[2-(3,4-dichloro-phenyl)-6-methoxy-benzoimidazol-1-yl]-acetamide,
2-[2-(4-Chloro-phenyl)-6-methoxy-benzoimidazol-1-yl]-2,N-dicyclohexyl-acetamide,
2-[2-(5-Chloro-thiophen-2-yl)-6-methoxy-benzoimidazol-1-yl]-2,N-dicyclohexyl-acetamide,
2-[2-(3-Chloro-4-methoxy-phenyl)-6-methoxy-benzoimidazol-1-yl]-2,N-dicyclohexyl-acetamide,
2-[2-(4-Chloro-3-fluoro-phenyl)-6-methoxy-benzoimidazol-1-yl]-2,N-dicyclohexyl-acetamide,
2-Cyclohexyl-N-cyclopentyl-2-[2-(3,4-dichloro-phenyl)-6-methoxy-benzoimidazol-1-yl]-acetamide,
N-Cyclohexyl-2-cyclopentyl-2-[2-(3,4-dichloro-phenyl)-6-methoxy-benzoimidazol-1-yl]-acetamide,
2-[2-(4-Chloro-phenyl)-6-methoxy-benzoimidazol-1-yl]-2-cyclohexyl-N-cyclopentyl-acetamide,
2-[2-(3-Chloro-phenyl)-6-methoxy-benzoimidazol-1-yl]-2,N-dicyclohexyl-acetamide,
2,N-Dicyclopentyl-2-[2-(3,4-dichloro-phenyl)-6-methoxy-benzoimidazol-1-yl]-acetamide,
2-[2-(4-Chloro-phenyl)-6-methoxy-benzoimidazol-1-yl]-N-cyclohexyl-2-cyclopentyl-acetamide,
2-[2-(4-Chloro-3-fluoro-phenyl)-6-methoxy-benzoimidazol-1-yl]-2-cyclohexyl-N-cyclopentyl-acetamide,
2-[2-(3-Chloro-4-methoxy-phenyl)-6-methoxy-benzoimidazol-1-yl]-2-cyclohexyl-N-cyclopentyl-acetamide,
2,N-Dicyclohexyl-2-[2-(4-fluoro-phenyl)-6-methoxy-benzoimidazol-1-yl]-acetamide,
2-[2-(3-Chloro-phenyl)-6-methoxy-benzoimidazol-1-yl]-2-cyclohexyl-N-cyclopentyl-acetamide,
2-[2-(3-Chloro-4-methoxy-phenyl)-6-methoxy-benzoimidazol-1-yl]-N-cyclohexyl-2-cyclopentyl-acetamide,
2-[2-(5-Chloro-thiophen-2-yl)-6-methoxy-benzoimidazol-1-yl]-N-cyclohexyl-2-cyclopentyl-acetamide,
2-Cyclobutyl-N-cyclohexyl-2-[2-(3,4-dichloro-phenyl)-6-methoxy-benzoimidazol-1-yl]-acetamide,
2-[2-(5-Chloro-thiophen-2-yl)-6-methoxy-benzoimidazol-1-yl]-2-cyclohexyl-N-cyclopentyl-acetamide,
2-[2-(6-Chloro-pyridin-3-yl)-6-methoxy-benzoimidazol-1-yl]-2,N-dicyclohexyl-acetamide,
2-[2-(3-Chloro-phenyl)-6-methoxy-benzoimidazol-1-yl]-N-cyclohexyl-2-cyclopentyl-acetamide,
2-[2-(3-Chloro-4-methoxy-phenyl)-6-methoxy-benzoimidazol-1-yl]-2,N-dicyclopentyl-acetamide,
2,N-Dicyclohexyl-2-[6-methoxy-2-(6-trifluoromethyl-pyridin-3-yl)-benzoimidazol-1-yl]-acetamide,
2-[2-(5-Chloro-thiophen-2-yl)-6-methoxy-benzoimidazol-1-yl]-2-cyclobutyl-N-cyclohexyl-acetamide,
2-[2-(3-Chloro-phenyl)-6-methoxy-benzoimidazol-1-yl]-2-cyclobutyl-N-cyclohexyl-acetamide,
N-Cyclohexyl-2-cyclopentyl-2-[2-(4-fluoro-phenyl)-6-methoxy-benzoimidazol-1-yl]-acetamide,
and any pharmaceutically acceptable salt or ester thereof.

Other particularly preferred compounds of formula (I) are those selected from the group consisting of:
2-[1-(Cyclohexyl-cyclohexylcarbamoyl-methyl)-1H-benzoimidazol-2-yl]-benzamide,
(S)-2,N-Dicyclohexyl-2-[2-(2,4-dimethoxy-phenyl)-benzoimidazol-1-yl]-acetamide,
(S)-2-[2-(4-Chloro-phenyl)-benzoimidazol-1-yl]-2,N-dicyclohexyl-acetamide, (S)-2-[2-(4-Chloro-phenyl)-benzoimidazol-1-yl]-4-methyl-pentanoic acid cyclohexylamide, 2-[2-(4-Chloro-phenyl)-benzoimidazol-1-yl]-N-cyclohexyl-2-(4-trifluoromethyl-phenyl)-acetamide, (S)-2-Cyclohexyl-2-[2-(2,4-dimethoxy-phenyl)-benzoimidazol-1-yl]-N-(2,6-dimethyl-phenyl)-acetamide, (S)-2-[2-(4-Chloro-phenyl)-benzoimidazol-1-yl]-2-cyclohexyl-N-(4,4-difluoro-cyclohexyl)-acetamide, (S)-2-[6-Chloro-2-(4-chloro-phenyl)-5-fluoro-benzoimidazol-1-yl]-N-cyclohexyl-2-(tetrahydro-pyran-4-yl)-acetamide, (S)-2-[2-(5-Chloro-thiophen-2-yl)-benzoimidazol-1-yl]-2,N-dicyclohexyl-acetamide, (S)-2-[6-Chloro-2-(4-chloro-phenyl)-5-fluoro-benzoimidazol-1-yl]-heptanoic acid cyclohexylamide, 2-[6-Chloro-2-(4-chloro-phenyl)-5-fluoro-benzoimidazol-1-yl]-2-cyclohexyl-N-(tetrahydro-pyran-4-yl)-acetamide, 2-[2-(3-Chloro-phenyl)-5,6-difluoro-benzoimidazol-1-yl]-2,N-dicyclohexyl-acetamide, (S)-2,N-Dicyclohexyl-2-[6-fluoro-2-(3-methyl-thiophen-2-yl)-benzoimidazol-1-yl]-acetamide, (S)-2-[2-(2-Chloro-phenyl)-5,6-difluoro-benzoimidazol-1-yl]-2,N-dicyclohexyl-acetamide, (S)-2-[2-(4-Chloro-phenyl)-6-fluoro-benzoimidazol-1-yl]-N-cyclohexyl-2-(R)-tetrahydro-pyran-2-yl-acetamide, (S)-2-[2-(4-Chloro-phenyl)-6-fluoro-benzoimidazol-1-yl]-N-cyclohexyl-2-(S)-tetrahydro-pyran-2-yl-acetamide, 2-[2-(4-Chloro-phenyl)-5-fluoro-benzoimidazol-1-yl]-N-cyclohexyl-2-(tetrahydro-pyran-2-yl)-acetamide, and any pharmaceutically acceptable salt or ester thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises cyclisation of a compound of formula (II)

(II)

wherein $R^1$, $R^2$, $R^3$, $R^4$, $R^5$, $R^6$, $R^7$ and $R^8$ are as defined above.

The cyclisation of a compound of formula (II) can be performed under reaction conditions well known to the person skilled in the art. Such cyclisations can conveniently be carried e.g. in a suitable solvent such as e.g. dichloromethane at a suitable temperature in the presence of a suitable reagent such as free $PPh_3$ or resin bound $PPh_3$.

The present invention also relates to compounds of formula (I) as defined above, when prepared by a process as described above.

The compounds of formula (I) can be prepared by methods known in the art or as described below. Unless otherwise indicated, the substituents $R^1$, $R^2$, $R^3$, $R^4$, $R^5$, $R^6$, $R^7$, and $R^8$ are as described above.

Compounds of formula (I) according to the present invention can be prepared e.g. by the methods and procedures given below. A typical procedure for the preparation of compounds of formula I is illustrated in the scheme below.

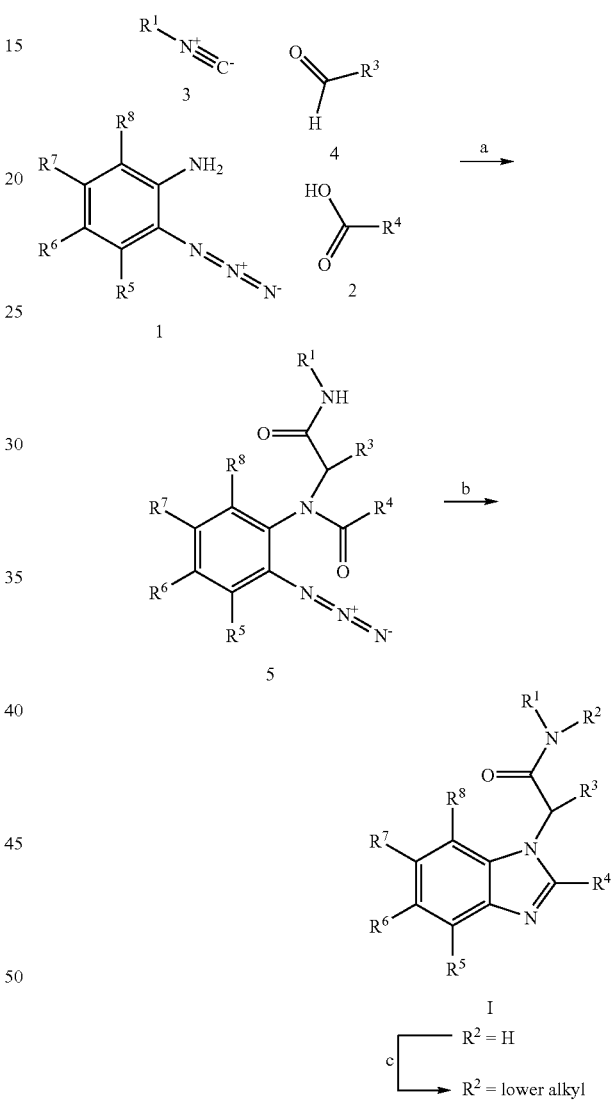

In a suitable organic solvent such as e.g. MeOH a 2-azidoarylamine 1, a carboxylic acid 2, an isonitrile 3 and an aldehyde 4 are condensed to 5 in a so called Ugi-type reaction (step a, typical procedures may e.g. be found in "The Peptides" by Gross & Meienhofer vol. 2, Academic Press, N.Y., 1980, pp 365-381). In a subsequent intramolecular Staudinger-type reaction with a suitable reagent such as e.g. $PPh_3$, the azido bisamide 5 is converted to the benzimidazole I, which can be optionally N-alkylated by deprotonation with a strong base (e.g. NaH or LiHMDA) and subsequent treatment with an alkylating agent $R^2$—X with X being a typical leaving group such as e.g. Cl, Br, I, SO₂alkyl, SO₂fluoroalkyl, SO₂aryl (step c). Many of the building blocks 2-4, particularly the carboxylic acid 2, are commercially available. If not, they may be prepared from commercially available starting materials using procedures described in literature and typically known to those skilled in the art. The isonitrile 3 can e.g. be obtained by dehydration of the corresponding formamide $R^1$—N—CHO with a suitable reagent such as e.g. phosgene, POCl₃ or Me₂N=CH⁺Cl Cl⁻. Aldehyde 4 can e.g. be prepared from the corresponding alcohol by oxidation with a suitable oxidant such as e.g. tetrapropylammonium perruthenate(VII). The 2-azidoarylamine 1 is usually prepared in three steps from the corresponding 2-aminoarylcarboxylic acid, which is converted into a 2-azidoarylcarboxylic acid by diazotation with NaNO₂ in a suitable solvent (e.g. methanol) and subsequent treatment with a suitable azide salt such as NaN₃. The resulting 2-azidoarylcarboxylic acid is then converted into 1 via Curtius rearrangement of the 2-azidoarylcarboxylic azide obtained from the 2-azidoarylcarboxylic acid by its activation of with a suitable reagent (e.g. chloroethylformiate in the presence of a base such as triethylamine) and subsequent treatment with a suitable source of azide anions (e.g. sodium azide). The 2-azidoaryl amine 1 can alternatively be prepared via the 2-azidoarylcarboxamide obtained by activation of the 2-azidoarylcarboxylic acid with a suitable reagent (e.g. chloroethylformiate in the presence of a base such as triethylamine) and subsequent treatment with ammonia. This amide is converted into 1 in a so called Hofmann-rearrangement by treatment with a suitable reagent such as NaOBr.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wutts, 2ⁿᵈ Ed., 1991, Wiley N.Y.) can be introduced before the critical step applying methods well known in the art. Such protecting groups can be removed at a later stage of the synthesis using standard methods described in the literature.

If compounds (1), (2), (3) or (4) contain stereogenic centers, compounds (I) can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure acids or by separation of the antipodes by specific chromatographic methods using either a chiral adsorbens or a chiral eluent.

An alternative approach to the preparation of compounds of formula I is illustrated in the scheme below.

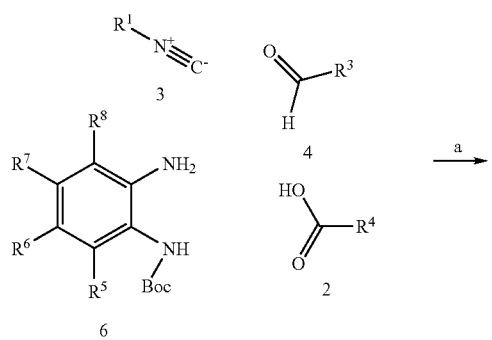

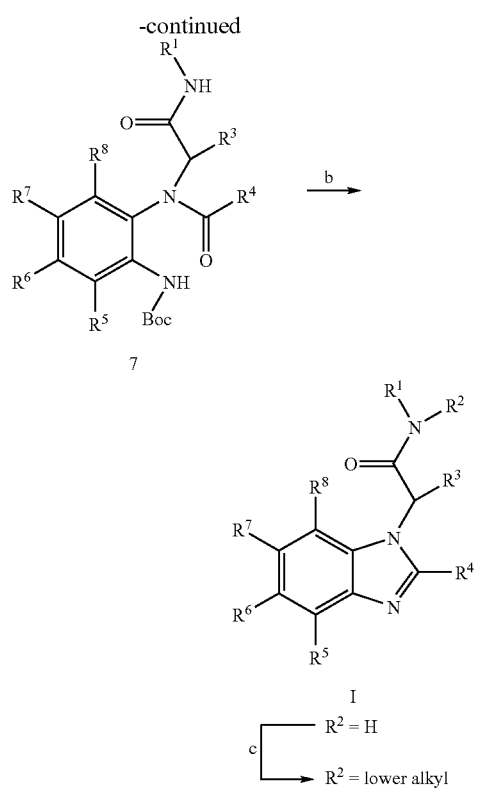

In this approach a mono boc-protected ortho arylene diamine 6, a carboxylic acid 2, an isonitrile 3, and an aldehyde 4 are condensed in an organic solvent such as e.g. methanol in the presence of an acid (such as e.g. HCl) to the bis amide 7 again in an Ugi-type condensation (step a). Bisamide 7 is deprotected with TFA and cyclised to the desired benzimidazole I (step b), which can be optionally N-alkylated by deprotonation with a strong base (e.g. NaH or LiHMDA) and subsequent treatment with an alkylating agent $R^2$—X with X being a typical leaving group such as e.g. Cl, Br, I, SO₂alkyl, SO₂fluoroalkyl, SO₂aryl (step c). Typical procedures applicable to this approach were described e.g. by Tempest et al. in Tet. Lett. 2001, 42, 4959-4962 and 4963-4968, or by Zhang et al. in Tet. Lett. 2004, 45, 6757-6760. Mono boc-protected ortho arylene diamines 1 are commercially available or may be prepared from the corresponding unprotected diamine by treatment with di-tert-butyl dicarbonate in an organic solvent such as e.g. THF in the presence of a base such as e.g. diisopropylethylamine.

If desired or required functional groups present in I (such as —CO₂alkyl, amino groups, cyano groups and others) may be derivatized to other functional groups using typical standard procedures known to those skilled in the art (e.g. reduction of —CO₂alkyl to —CH₂OH with LiAlH₄, hydrolysis of —CO₂alkyl to CO₂H and subsequent optional conversion to an amide, acylation of amino groups).

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wutts, 2ⁿᵈ Ed., 1991, Wiley N.Y.) can be introduced before the critical step applying methods well known in the art. Such protecting groups can be removed at a later stage of the synthesis using standard methods described in the literature.

If compounds (2), (3), (4) or (6) contain stereogenic centers, compounds (I) can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure acids or by separation of the antipodes by specific chromatographic methods using either a chiral adsorbens or a chiral eluent.

$R^1$ as present in (I) after steps a and b or steps a, b and c in above shown schemes may be transformed into or replaced by other $R^1$ using one or a sequence of reaction steps. Two possible examples are given below:

a) $R^1$=$CH_2Ph$ may for instance be removed using debenzylation conditions (e.g. hydrogenolysis in a solvent such as methanol in presence of a catalyst such as Pd(0) on charcoal powder) and a new $R^1$ can be introduced e.g. by deprotonation of the resulting $CONHR^2$ with a strong base (e.g. LiHMDA) and treatment with an alkylating agent $R^1$—X (X being a typical leaving group such as e.g. Cl, Br, I, $SO_2$alkyl, $SO_2$fluoroalkyl, $SO_2$aryl, and $R^1$ being $C_{1-10}$-alkyl, lower-alkoxy-lower-alkyl, lower-alkoxy-carbonyl-lower-alkyl, cycloalkyl, cycloalkyl-lower-alkyl, aryl-lower-alkyl, di-aryl-lower-alkyl, heteroaryl-lower-alkyl or heterocyclyl-lower-alkyl) or alternatively by a Pd(II)-promoted coupling with $R^1$—X ($R^1$ being aryl or heteroaryl and X being Cl, Br, I or $OSO_2CF_3$)

b) Amidolysis of the —$CR^3CONR^1R^2$-moiety of (I) to —$CR^3COOH$ may be carried out using suitable conditions such as heating in isopropanol in presence of NaOH or LiOH. A new amide bond can then be formed using an amine $HNR^1R^2$ and a typical peptide coupling reagent such as e.g. EDCI, DCC or TPTU.

Functional groups present in (I) which are not stable or are reactive under the reaction conditions of one or more of the reaction steps, can be protected with appropriate protecting groups (as described e.g. in "Protective Groups in Organic Chemistry" by T. W. Greene and P. G. M. Wutts, $2^{nd}$ Ed., 1991, Wiley N.Y.) before the critical step applying methods well known in the art. Such protecting groups can be removed at a later stage of the synthesis using standard methods described in the literature.

The conversion of a compound of formula (I) into a pharmaceutically acceptable salt can be carried out by treatment of such a compound with an inorganic acid, for example a hydrohalic acid, such as, for example, hydrochloric acid or hydrobromic acid, or other inorganic acids such as sulfuric acid, nitric acid, phosphoric acid etC., or with an organic acid, such as, for example, acetic acid, citric acid, maleic acid, fumaric acid, tartaric acid, methanesulfonic acid or p-toluenesulfonic acid. The salts with an inorganic or organic acid can be obtained by standard methods known to the person skilled in the art, e.g. by dissolving the compound of formula (I) in a suitable solvent such as e.g. dioxane or THF and adding an appropriate amount of the corresponding acid. The products can conveniently be isolated by filtration or by chromatography. If a carboxy group is present, the corresponding carboxylate salts can be prepared from the compounds of formula (I) by treatment with physiologically compatible bases. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

The conversion of compounds of formula (I) into pharmaceutically acceptable esters can be carried out e.g. by treatment of hydroxy groups present in the molecules with a carboxylic acid such as acetic acid, with a condensating reagent such as benzotriazol-1-yloxytris(dimethylamino) phosphonium hexafluorophosphate (BOP), N,N-dicyclohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluorborate (TPTU) to produce the carboxylic ester or carboxylic amide. Furthermore, carboxy groups present in the compounds of formula (I) can be reacted with suitable alcohols under analogous conditions as described above.

Insofar as their preparation is not described in the examples, the compounds of formula (I) as well as all intermediate products can be prepared according to analogous methods or according to the methods set forth above. Starting materials are commercially available or known in the art.

As described above, the novel compounds of the present invention have been found to bind to and selectively activate FXR. They can therefore be used in the treatment and prophylaxis of diseases which are modulated by FXR agonists. Such diseases include increased lipid and cholesterol levels, particularly high LDL-cholesterol, high triglycerides, low HDL-cholesterol, dyslipidemia, atherosclerotic disease, diabetes, particularly non-insulin dependent diabetes mellitus, metabolic syndrome, cholesterol gallstone disease, cholestasis/fibrosis of the liver, diseases of cholesterol absorption, cancer, particularly gastrointestinal cancer, osteoporosis, peripheral occlusive disease, ischemic stroke, Parkinson's disease and/or Alzheimer's disease.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are modulated by FXR agonists, particularly as therapeutically active substances for the treatment and/or prophylaxis of increased lipid and cholesterol levels, high LDL-cholesterol, high triglycerides, low HDL-cholesterol, dyslipidemia, atherosclerotic disease, diabetes, non-insulin dependent diabetes mellitus, metabolic syndrome, cholesterol gallstone disease, cholestasis/fibrosis of the liver, diseases of cholesterol absorption, cancer, gastrointestinal cancer, osteoporosis, peripheral occlusive disease, ischemic stroke, Parkinson's disease and/or Alzheimer's disease.

In another preferred embodiment, the invention relates to a method for the therapeutic and/or prophylactic treatment of diseases which are modulated by FXR agonists, particularly for the therapeutic and/or prophylactic treatment of increased lipid and cholesterol levels, high LDL-cholesterol, high triglycerides, low HDL-cholesterol, dyslipidemia, atherosclerotic disease, diabetes, non-insulin dependent diabetes mellitus, metabolic syndrome, cholesterol gallstone disease, cholestasis/fibrosis of the liver, diseases of cholesterol absorption, cancer, gastrointestinal cancer, osteoporosis, peripheral occlusive disease, ischemic stroke, Parkinson's disease and/or Alzheimer's disease which method comprises administering a compound as defined above to a human being or animal.

The invention also embraces the use of compounds as defined above for the therapeutic and/or prophylactic treatment of diseases which are modulated by FXR agonists, particularly for the therapeutic and/or prophylactic treatment of increased lipid and cholesterol levels, high LDL-cholesterol, high triglycerides, low HDL-cholesterol, dyslipidemia, atherosclerotic disease, diabetes, non-insulin dependent diabetes mellitus, metabolic syndrome, cholesterol gallstone disease, cholestasis/fibrosis of the liver, diseases of cholesterol absorption, cancer, gastrointestinal cancer, osteoporosis, peripheral occlusive disease, ischemic stroke, Parkinson's disease and/or Alzheimer's disease.

The invention also relates to the use of compounds as described above for the preparation of medicaments for the therapeutic and/or prophylactic treatment of diseases which are modulated by FXR agonists, particularly for the therapeutic and/or prophylactic treatment of increased lipid and cholesterol levels, high LDL-cholesterol, high triglycerides, low HDL-cholesterol, dyslipidemia, atherosclerotic disease, diabetes, non-insulin dependent diabetes mellitus, metabolic syndrome, cholesterol gallstone disease, cholestasis/fibrosis of the liver, diseases of cholesterol absorption, cancer, gastrointestinal cancer, osteoporosis, peripheral occlusive disease, ischemic stroke, Parkinson's disease and/or Alzheimer's disease. Such medicaments comprise a compound as described above.

Prevention and/or treatment of high LDL cholesterol levels, high triglycerides, dyslipidemia, cholesterol gallstone disease, cancer, non-insulin dependent diabetes mellitus and metabolic syndrome is preferred, particularly high LDL cholesterol, high triglyceride levels and dyslipidemia.

The following tests were carried out in order to determine the activity of the compounds of formula (I). Background information on the binding assay can be found in: Nichols J S et al. "Development of a scintillation proximity assay for peroxisome proliferator-activated receptor gamma ligand binding domain", (1998) Anal. Biochem. 257: 112-119.

Bacterial and mammalian expression vectors were constructed to produce glutathione-s-transferase (GST) and Gal4 DNA binding domain (GAL) proteins fused to the ligand binding domain (LBD) of human FXR (aa 193-473). To accomplish this, the portions of the sequences encoding the FXR LBD were amplified by polymerase chain reaction (PCR) from a full-length clone by PCR and then subcloned into the plasmid vectors. The final clone was verified by DNA sequence analysis.

The induction, expression, and subsequent purification of GST-LBD fusion protein was performed in *E. coli* strain BL21 (pLysS) cells by standard methods (Current Protocols in Molecular Biology, Wiley Press, ed. Ausubel et al).

Radioligand Binding Assay

Binding of test substances to the FXR ligand binding domain was assessed in a radioligand displacement assay. The assay was performed in a buffer consisting of 50 mM Hepes, pH 7.4, 10 mM NaCl, 5 mM $MgCl_2$. For each reaction well in a 96-well plate, 40 nM of GST-FXR LBD fusion protein was bound to 10 μg glutathione ytrium silicate SPA beads (PharmaciaAmersham) in a final volume of 50 μl by shaking. A radioligand (e.g. 40 nM) of 2,N-dicyclohexyl-2-[2-(2,4 dimethoxy-phenyl)-benzoimidazol-1-yl]-acetamide) was added, and the reaction incubated at RT for 30 minutes in the presence of test compounds followed by scintillation proximity counting. All binding assays were performed in 96-well plates and the amount of bound ligand was measured on a Packard TopCount using OptiPlates (Packard). Dose response curves were performed within a range of concentration from $6 \times 10^{-9}$ M to $2.5 \times 10^{-5}$ M.

Luciferase Transcriptional Reporter Gene Assays

Baby hamster kidney cells (BHK21 ATCC CCL10) were grown in DMEM medium containing 10% FBS at 37° C. in a 95% O2:5% $CO_2$ atmosphere. Cells were seeded in 6-well plates at a density of $10^5$ cells/well and then transfected with the pFA-FXR-LBD or expression plasmid plus a reporter plasmid. Transfection was accomplished with the Fugene 6 reagent (Roche Molecular Biochemicals) according to the suggested protocol. Six hours following transfection, the cells were harvested by trypsinization and seeded in 96-well plates at a density of $10^4$ cells/well. After 24 hours to allow attachment of cells, the medium was removed and replaced with 100 μl of phenol red-free medium containing the test substances or control ligands (final DMSO concentration: 0.1%). Following incubation of the cells for 24 hours with substances, 50 μl of the supernatant was discarded and then 50 μl of Luciferase Constant-Light Reagent (Roche Molecular Biochemicals) was added to lyse the cells and initiate the luciferase reaction. Luminescence, as a measure of luciferase activity, was detected in a Packard TopCount. Transcriptional activation in the presence of a test substance was expressed as fold-change in luminescence compared to that of cells incubated in the absence of the substance. $EC_{50}$ values were calculated using the XLfit program (ID Business Solutions Ltd. UK).

The compounds according to formula (I) have an activity in at least one of the above assays (EC50 or IC50), preferably of 0.5 nM to 10 μM, more preferably 0.5 nM to 100 nM.

For example, the following compounds showed the following $EC_{50}$ and $IC_{50}$ values in the binding assay described above:

| Example | $EC_{50}$ [μM] | $IC_{50}$ [μM] |
|---|---|---|
| 2 | 0.7 | 1.5 |
| 34 | 0.086 | 0.5 |

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula I.

The following examples serve to illustrate the present invention in more detail. They are, however, not intended to limit its scope in any manner.

EXAMPLES

Abbreviations

HCl=hydrogen chloride; HPLC=high pressure liquid chromatography; NaHCO$_3$=sodium hydrogen carbonate; Na$_2$SO$_4$=sodium sulfate; PS-carbonate=polystyrene supported carbonate prepared from commercial Ambersep 900-OH (Acros Cat. 30134 5000) with saturated aq. CaCO$_3$; PS-TsNHNH$_2$=polystyrene supported tosylhydrazine (Aldrich 532320-5g); SiO$_2$=silica gel; MS (ES+)=mass spectrometry using electrospray ionization; and (M+H)=the molecular weight of the compound plus a proton.

General Remarks

Reactions were carried out under nitrogen or argon atmosphere, when appropriate.

Example 1

2,N-dicyclohexyl-2-(2-phenyl-benzoimidazol-1-yl)-acetamide hydrogen chloride 1.1

Benzoic acid (34.2 mg, 0.28 mmol, 1.1 equiv.) was added to a solution of cyclohexanecarbaldehyde (42.6 mg, 0.38 mmol, 1.5 equiv.), cyclohexyl isocyanide (30.6 mg, 0.28 mmol, 1.1 equiv.) and N-tert-butoxycarbonyl phenylene diamine (52.1 mg, 0.25 mmol, 1 equiv.) in methanol (0.5 mL) and the mixture was stirred at room temperature for 16 hours.

1 M aqueous HCl (1 mL) was added and the mixture was extracted with dichloromethane (2×1 mL). Na$_2$SO$_4$ (50 mg), PS-carbonate (4 mmol/g, 50 mg) and PS-TsNHNH$_2$ (4 mmol/g, 50 mg) were added to the organic phase and the mixture was shaken for 60 minutes. The mixture was filtered and the filtrate evaporated in-vacuo. Purification by preparative HPLC (gradient elution: water/acetonitrile with 0.1% trifluoroacetic acid) afforded {2-[benzoyl-(cyclohexyl-cyclohexylcarbamoyl-methyl)-amino]phenyl}-carbamic acid tert-butyl ester, 64 mg (47%) as a yellow oil. MS (ES+): 534 (M+H).

1.2

Concentrated HCl (25% in water, 0.5 mL) was added to a solution of {2-[benzoyl-(cyclohexyl-cyclohexylcarbamoyl-methyl)-amino]phenyl}-carbamic acid tert-butyl ester (64 mg, 0.12 mmol) in methanol (2.0 mL). The reaction mixture was heated in a focussed microwave (CEM Discovery) at 145° C., for 3 minutes with stirring. The reaction mixture was then evaporated to afford 2,N-dicyclohexyl-2-(2-phenyl-benzoimidazol-1-yl)-acetamide hydrogen chloride, 46 mg (85%) as a pale yellow solid. MS (ES+): 416 (M+H).

Example 2

2-[2-(4-chloro-phenyl)-benzoimidazol-1-yl]-4-methyl-pentanoic acid cyclohexylamide 2.1

4-chlorobenzoic acid (43.8 mg, 0.28 mmol, 1.1 equiv.) was added to a solution of 3-methylbutyraldehyde (21.5 mg, 0.38 mmol, 1.5 equiv.), cyclohexyl isocyanide (30.6 mg, 0.28 mmol, 1.1 equiv.) and N-tert-butoxycarbonyl phenylene diamine (52.1 mg, 0.25 mmol, 1 equiv.) in methanol (0.5 mL). The reaction mixture was heated in a focussed microwave (CEM Discovery) at 100° C., for 10 minutes with stirring. The solvent was removed in-vacuo and the residue re-dissolved in dichloromethane (2 mL), washed with 1 M aqueous HCl (2 mL), saturated aqueous solution of NaHCO$_3$ (2 mL), dried over Na$_2$SO$_4$ and evaporated under vacuum to afford crude {2-[(4-chloro-benzoyl)-(1-cyclohexylcarbamoyl-3-methyl-butyl)-amino]-phenyl}-carbamic acid tert-butyl ester, 83 mg (61%) as an oil. MS (ES+): 564 (M+H).

2.2

Concentrated HCl (25% in water, 0.5 mL) was added to a solution of crude {2-[(4-chloro-benzoyl)-(1-cyclohexylcarbamoyl-3-methyl-butyl)-amino]-phenyl}-carbamic acid tert-butyl ester (83 mg, 0.12 mmol) in methanol (2.0 mL). The reaction mixture was heated in a focussed microwave (CEM Discovery) at 145° C., for 3 minutes with stirring. The reaction mixture was then evaporated, purified by preparative HPLC (gradient elution: water/acetonitrile with 0.1% trifluoroacetic acid) and evaporated under vacuum. This was then re-dissolved in dichloromethane (2 mL), PS-carbonate resin (4 mmol/g, 100 mg) was added and the mixture shaken for 2 hours. The mixture was filtered and evaporated to afford 2-[2-(4-chloro-phenyl)-benzoimidazol-1-yl]-4-methyl-pentanoic acid cyclohexylamide, 30 mg (46%) as a white solid. MS (ES+): 424 (M+H).

Example 3

4-{1-[cyclohexyl-(4-morpholin-4-yl-phenylcarbamoyl)-methyl]-1H-benzoimidazol-2-yl}-benzoic acid methyl ester hydrochloride 3.1

4-morpholinobenzoisonitrile (109 mg, 0.58 mmol, 1.1 equiv.) was added to a solution of mono-methyl terephthalate (95 mg, 0.53 mmol, 1.1 equiv.), cyclohexanecarbaldehyde (81 mg, 0.72 mmol, 1.5 equiv.) and N-tert-butoxycarbonyl phenylene diamine (100 mg, 0.48 mmol, 1 equiv.) in methanol (1.0 mL). The reaction mixture was heated in a focussed microwave (CEM Discovery) at 100° C., for 10 minutes with stirring. The solvent was removed in vacuo and the residue re-dissolved in dichloromethane (2 mL), washed with 1 N aqueous HCl (2 mL), saturated aqueous solution of NaHCO$_3$ (2 mL), dried over Na$_2$SO$_4$ and evaporated under vacuum. The crude product was purified by preparative HPLC (gradient elution: water/acetonitrile with 0.1% trifluoroacetic acid) and evaporated under vacuum to afford N-(2-tert-butoxycarbonylamino-phenyl)-N-[cyclohexyl-(4-morpholin-4-yl-phenylcarbamoyl)-methyl]-terephthalamic acid methyl ester, 158 mg (49%). MS (ES+): 671 (M+H).

3.2

Concentrated HCl (25% in water, 0.5 mL) was added to a solution of crude {2-[(4-chloro-benzoyl)-(1-cyclohexylcarbamoyl-3-methyl-butyl)-amino]-phenyl}-carbamic acid tert-butyl ester (83 mg, 0.12 mmol) in methanol (2.0 mL). The reaction mixture was heated in a focussed microwave (CEM Discovery) at 145° C. for 3 minutes with stirring. The reaction mixture was evaporated, purified by preparative HPLC (gradient elution: with water/acetonitrile under neutral conditions) and evaporated under vacuum, to afford 4-{1-[cyclohexyl-(4-morpholin-4-yl-phenylcarbamoyl)-methyl]1H-benzoimidazol-2-yl}-benzoic acid methyl ester hydrogen chloride, 78 mg (60%) as a colorless oil. MS (ES+): 553 (M+H).

Example 4

2,N-dicyclohexyl-2-[5,6-dichloro-2-(2,4-dimethoxy-phenyl)-benzoimidazol-1-yl]-acetamide 4.1

Di-tert-butyl dicarbonate (1.36 g, 6.21 mmol, 1.1 equiv.) was added to a stirred solution of 4,5-dichloro-benzene-1,2-diamine (1.00 g, 5.65 mmol, 1.0 equiv.) in tetrahydrofuran (10 mL) and N,N-diisopropylethylamine (0.81 g, 6.21 mmol, 1.1 equiv.) at 0° C. and the reaction mixture was stirred for 16 hours and allowed to warm to room temperature. The reaction mixture was evaporated in-vacuo and the crude product dry-loaded onto SiO$_2$ and purified by column chromatography (SiO$_2$, ethyl acetate:n-heptane 1:9 to 1:2) to afford (2-amino-4,5-dichloro-phenyl)-carbamic acid tert-butyl ester, 0.81 g (52%) as an off-white solid. MS (ES+): 221, 277 (M-tert-butyl, M+H).

4.2

In analogy to examples 2.1-2.2, benzoic acid, cyclohexanecarbaldehyde, cyclohexyl isocyanide, and (2-amino-4,5-dichloro-phenyl)-carbamic acid tert-butyl ester gave 2,N-dicyclohexyl-2-[5,6-dichloro-2-(2,4-dimethoxy-phenyl)-benzoimidazol-1-yl]-acetamide as a colorless oil. MS (ES+): 544 (M+H).

Example 5

2-cyclohexyl-2-[2-(2,4-dimethoxy-phenyl)-benzoimidazol-1-yl]-N-isopropyl-acetamide hydrogen chloride In analogy to examples 3.1-3.2, 2,4-dimethoxy-benzoic acid, cyclohexanecarbaldehyde, isopropyl isocyanide, and N-tert-butoxycarbonyl phenylene diamine gave 2-cyclohexyl-2-[2-(2,4-dimethoxy-phenyl)-benzoimidazol-1-yl]-N-isopropyl-acetamide hydrogen chloride as a brown solid, MS (ES+): 436 (M+H).

Example 6

2,N-dicyclohexyl-2-[2-(4-methoxy-phenyl)-benzoimidazol-1-yl]-acetamide hydrogen chloride In analogy to examples 3.1-3.2, 4-methoxy-benzoic acid, cyclohexanecarbaldehyde, cyclohexyl isocyanide, and N-tert-butoxycarbonyl phenylene diamine gave 2,N-dicyclohexyl-2-[2-(4-methoxy-phenyl)-benzoimidazol-1-yl]-acetamide hydrogen chloride as a brown solid, MS (ES+): 446 (M+H).

Example 7

2,N-dicyclohexyl-2-[2-(3-methoxy-phenyl)-benzoimidazol-1-yl]-acetamide hydrogen chloride In analogy to examples 3.1-3.2, 3-methoxy-benzoic acid, cyclohexanecarbaldehyde, cyclohexyl isocyanide, and N-tert-butoxycarbonyl phenylene diamine gave 2,N-dicyclohexyl-2-[2-(3-methoxy-phenyl)-benzoimidazol-1-yl]-acetamide hydrogen chloride as a brown solid, MS (ES+): 446 (M+H).

Example 8

2,N-dicyclohexyl-2-[2-(2-methoxy-phenyl)-benzoimidazol-1-yl]-acetamide hydrogen chloride In analogy to examples 3.1-3.2, 2-methoxy-benzoic acid, cyclohexanecarbaldehyde, cyclohexyl isocyanide, and N-tert-butoxycarbonyl phenylene diamine gave 2,N-dicyclohexyl-2-[2-(2-methoxy-phenyl)-benzoimidazol-1-yl]-acetamide hydrogen chloride as a yellow oil, MS (ES+): 446 (M+H).

Example 9

2,N-dicyclohexyl-2-(2-naphthalen-1-yl-benzoimidazol-1-yl)-acetamide hydrogen chloride In analogy to examples 3.1-3.2, naphthalene-1-carboxylic acid, cyclohexanecarbaldehyde, cyclohexyl isocyanide, and N-tert-butoxycarbonyl phenylene diamine gave 2,N-dicyclohexyl-2-(2-naphthalen-1-yl-benzoimidazol-1-yl)-acetamide hydrogen chloride as a yellow oil, MS (ES+): 466 (M+H).

Example 10

2,N-dicyclohexyl-2-[2-(3-ethoxy-phenyl)-benzoimidazol-1-yl]-acetamide hydrogen chloride In analogy to examples 3.1-3.2, 3-ethoxy-benzoic acid, cyclohexanecarbaldehyde, cyclohexyl isocyanide, and N-tert-butoxycarbonyl phenylene diamine gave 2,N-dicyclohexyl-2-[2-(3-ethoxy-phenyl)-benzoimidazol-1-yl]-acetamide hydrogen chloride as a brown solid, MS (ES+): 460 (M+H).

Example 11

N-cyclohexyl-2-[2-(2,4-dimethoxy-phenyl)-benzoimidazol-1-yl]-4-phenyl-butyramide In analogy to example 28.3, 2,4-dimethoxy-benzoic acid, 3-phenylpropanal, cyclohexyl isocyanide, and 2-azido-phenylamine gave N-cyclohexyl-2-[2-(2,4-dimethoxy-phenyl)-benzoimidazol-1-yl]-4-phenyl-butyramide, MS (ES+): 498 (M+H).

Example 12

N-cyclohexyl-2-[2-(2,4-dimethoxy-phenyl)-benzoimidazol-1-yl]-3-methyl-butyramide hydrogen chloride In analogy to examples 3.1-3.2, 2,4-dimethoxy-benzoic acid, 2-methyl propanal, cyclohexyl isocyanide, and N-tert-butoxycarbonyl phenylene diamine gave N-cyclohexyl-2-[2-(2,4-dimethoxy-phenyl)-benzoimidazol-1-yl]-3-methyl-butyramide hydrogen chloride as a brown solid, MS (ES+): 436 (M+H).

Example 13

N-cyclohexyl-2-[2-(2,4-dimethoxy-phenyl)-benzoimidazol-1-yl]-3-phenyl-propionamide hydrogen chloride In analogy to examples 3.1-3.2, 2,4-dimethoxy-benzoic acid, phenylacetaldehyde cyclohexyl isocyanide, and N-tert-butoxycarbonyl phenylene diamine gave N-cyclohexyl-2-[2-(2,4-dimethoxy-phenyl)-benzoimidazol-1-yl]-3-phenyl-propionamide hydrogen chloride as a off-white solid, MS (ES+): 484 (M+H).

Example 14

N-cyclohexyl-2-[2-(2,4-dimethoxy-phenyl)-benzoimidazol-1-yl]-2-pyridin-2-yl-acetamide hydrogen chloride In analogy to examples 3.1-3.2, 2,4-dimethoxy-benzoic acid, pyridine-2-carbaldehyde, cyclohexyl isocyanide, and N-tert-butoxycarbonyl phenylene diamine gave N-cyclohexyl-2-[2-(2,4-dimethoxy-phenyl)-benzoimidazol-1-yl]-2-pyridin-2-yl-acetamide hydrogen chloride as a brown oil, MS (ES+): 471 (M+H).

Example 15

N-cyclohexyl-2-cyclopentyl-2-[2-(2,4-dimethoxy-phenyl)-benzoimidazol-1-yl]-acetamide hydrogen chloride In analogy to examples 3.1-3.2, 2,4-dimethoxy-benzoic acid, cyclopentylcarbaldehyde, cyclohexyl isocyanide, and N-tert-butoxycarbonyl phenylene diamine gave N-cyclohexyl-2-cyclopentyl-2-[2-(2,4-dimethoxy-phenyl)-benzoimidazol-1-yl]-acetamide hydrogen chloride as green solid, MS (ES+): 462 (M+H).

Example 16

4-{[1-cyclohexyl-(cyclohexylcarbamoyl-methyl)]-1H-benzoimidazol-2-yl}-benzoic acid methyl ester In analogy to examples 2.1-2.2, terephthalic acid monomethyl ester, cyclohexanecarbaldehyde, cyclohexyl isocyanide, and N-tert-butoxycarbonyl phenylene diamine gave 4-{[1-cyclohexyl-(cyclohexylcarbamoyl-methyl)]-1H-benzoimidazol-2-yl}-benzoic acid methyl ester as white solid, MS (ES+): 474 (M+H).

Example 17

2,N-dicyclohexyl-2-(2-naphthalen-2-yl-benzoimidazol-1-yl)-acetamide

In analogy to examples 2.1-2.2, naphthalene-2-carboxylic acid, cyclohexanecarbaldehyde, cyclohexyl isocyanide, and N-tert-butoxycarbonyl phenylene diamine gave 2,N-dicyclohexyl-2-(2-naphthalen-2-yl-benzoimidazol-1-yl)-acetamide as a white solid, MS (ES+): 466 (M+H).

Example 18

2,N-dicyclohexyl-2-[2-(3-thiophen-2-yl-phenyl)-benzoimidazol-1-yl]-acetamide

In analogy to examples 2.1-2.2, 3-thiophen-2-yl-benzoic acid, cyclohexanecarbaldehyde, cyclohexyl isocyanide, and N-tert-butoxycarbonyl phenylene diamine gave 2,N-dicyclohexyl-2-[2-(3-thiophen-2-yl-phenyl)-benzoimidazol-1-yl]-acetamide hydrogen chloride as a white solid, MS (ES+): 498 (M+H).

Example 19

2,N-dicyclohexyl-2-[2-(5-phenyl-thiophen-2-yl)-benzoimidazol-1-yl]-acetamide

In analogy to examples 2.1-2.2, 5-phenyl-thiophene-2-carboxylic acid, cyclohexanecarbaldehyde, cyclohexyl isocyanide, and N-tert-butoxycarbonyl phenylene diamine gave 2,N-dicyclohexyl-2-[2-(5-phenyl-thiophen-2-yl)-benzoimidazol-1-yl]-acetamide as a white solid, MS (ES+): 498 (M+H).

Example 20

3-{[1-cyclohexyl-(cyclohexylcarbamoyl-methyl)]-1H-benzoimidazol-2-yl}-benzoic acid methyl ester In analogy to examples 2.1-2.2, isophthalic acid monomethyl ester, cyclohexanecarbaldehyde, cyclohexyl isocyanide, and N-tert-butoxycarbonyl phenylene diamine gave 3-{[1-cyclohexyl-(cyclohexylcarbamoyl-methyl)]-1H-benzoimidazol-2-yl}-benzoic acid methyl ester as a white solid, MS (ES+): 474 (M+H).

Example 21

2-[2-(3-hydroxy-phenyl)-benzoimidazol-1-yl]-4-methyl-pentanoic acid cyclohexylamide In analogy to examples 2.1-2.2, 3-hydroxy benzoic acid, 3-methyl butyraldehyde, cyclohexyl isocyanide, and N-tert-butoxycarbonyl phenylene diamine gave 2-[2-(3-hydroxyphenyl)-benzoimidazol-1-yl]-4-methyl-pentanoic acid cyclohexylamide as a white solid, MS (ES+): 406 (M+H).

Example 22

2-[2-(4-hydroxymethyl-phenyl)-benzoimidazol-1-yl]-4-methyl-pentanoic acid cyclohexylamide In analogy to examples 2.1-2.2, 4-hydroxymethyl benzoic acid, 3-methyl butyraldehyde, cyclohexyl isocyanide, and N-tert-butoxycarbonyl phenylene diamine gave 2-[2-(4-hydroxymethyl-phenyl)-benzoimidazol-1-yl]-4-methyl-pentanoic acid cyclohexylamide as a white solid, MS (ES+): 420 (M+H).

Example 23

2-[2-(1H-indol-5-yl)-benzoimidazol-1-yl]-4-methyl-pentanoic acid cyclohexylamide In analogy to examples 2.1-2.2, 1H-indole-5-carboxylic acid, 3-methyl butyraldehyde, cyclohexyl isocyanide, and N-tert-butoxycarbonyl phenylene diamine gave 2-[2-(1H-indol-5-yl)-benzoimidazol-1-yl]-4-methyl-pentanoic acid cyclohexylamide as a white solid, MS (ES+): 429 (M+H).

Example 24

2-[2-(1H-indol-6-yl)-benzoimidazol-1-yl]-4-methyl-pentanoic acid cyclohexylamide In analogy to examples 2.1-2.2, 1H-indole-6-carboxylic acid, 3-methyl butyraldehyde, cyclohexyl isocyanide, and N-tert-butoxycarbonyl phenylene diamine gave 2-[2-(1H-indol-6-yl)-benzoimidazol-1-yl]-4-methyl-pentanoic acid cyclohexylamide hydrogen chloride as a yellow solid, MS (ES+): 429 (M+H).

Example 25

2-[2-(4-amino-phenyl)-benzoimidazol-1-yl]-4-methyl-pentanoic acid cyclohexylamide In analogy to examples 2.1-2.2, 4-amino benzoic acid, 3-methyl butyraldehyde, cyclohexyl isocyanide, and N-tert-butoxycarbonyl phenylene diamine gave 2-[2-(4-amino-phenyl)-benzoimidazol-1-yl]-4-methyl-pentanoic acid cyclohexylamide hydrogen chloride as white solid, MS (ES+): 405 (M+H).

Example 26

2-cyclohexyl-2-[2-(2,4-dimethoxy-phenyl)-benzoimidazol-1-yl]-N—((R)1-phenyl-ethyl)-acetamide In analogy to examples 2.1-2.2, 2,4-dimethoxy-benzoic acid, cyclohexanecarbaldehyde, (1-isocyano-ethyl)-benzene, and N-tert-butoxycarbonyl phenylene diamine gave 2-cyclohexyl-2-[2-(2,4-dimethoxy-phenyl)-benzoimidazol-1-yl]-N—((R)1-phenyl-ethyl)-acetamide as a white solid, MS (ES+): 498 (M+H).

Example 27

2,N-dicyclohexyl-2-[2-(4-hydroxymethyl-phenyl)-benzoimidazol-1-yl]-acetamide

In analogy to examples 2.1-2.2, 4-hydroxymethyl benzoic acid, cyclohexanecarbaldehyde, cyclohexyl isocyanide, and N-tert-butoxycarbonyl phenylene diamine gave 2,N-dicyclohexyl-2-[2-(4-hydroxymethyl-phenyl)-benzoimidazol-1-yl]-acetamide as a white solid, MS (ES+): 446 (M+H).

Example 28

N-cyclohexyl-2-[2-(2,3-dimethoxy-phenyl)-benzoimidazol-1-yl]-4-phenyl-butyramide 28.1
Anthranilic acid (12.3 g, 90 mmol) was dissolved in a mixture of aqueous HCl (36%, 50 mL), H₂O (100 mL), dioxane (50 mL) and methanol (50 mL) at 0° C. and treated dropwise with NaNO₂ (7.6 g, 110 mmol) dissolved in H₂O (50 ml) whereas the temperature of the reaction mixture was kept below 5° C. After 1 h at 0° C. the mixture was poured onto an icy solution of sodium acetate (26 g, 317 mmol) and sodium azide (15 g, 230 mmol) in ca. 300 ml of water. Repeated (ca. 3 times) extraction of the resulting suspension with ethylacetate, drying of the combined organic phases, and evaporation of the solvent gave (8.5 g, 58%) of 2-azido-benzoic acid. MS (ES+): 164 (M+H).

28.2
2-Azido-benzoic acid (3.7 g, 22.7 mmol) in dimethylformamide (75 mL) was cooled to −10° C. and treated with ethylchloroformate (2.6 g, 24 mmol). After stirring for 1 h at −10° C., NaN₃ (7.28 g, 112 mmol) dissolved in H₂O (50 mL) was added and the mixture allowed to reach ambient temperature. H₂O (300 ml) was added and the mixture extracted 3 times with ethylacetate. The ethylacetate phases were dried with Na₂SO₄ and stirred for 96 hrs at ambient temperature. The precipitate that had formed was filtered and chromatographed on SiO₂ with ethylacetate/hexane as eluent too give 304 mg (19%) of 2-azido-phenylamine. MS (ES+): 135 (M+H).

28.3
A mixture of 2-azido-phenylamine (68 mg, 0.5 mmol), 2,3-dimethoxy benzoic acid (91 mg, 0.5 mmol), 3-phenylpropanal (67 mg, 0.5 mmol), cyclohexyl isocyanide (55 mg, 0.5 mmol) in 2 ml of methanol was stirred 64 hrs at RT. The mixture was diluted with 7 ml of dichloromethane and treated with 25 µl of diisopropylethylamine. After cooling to 0° C. 450 mg of polymer bound triphenylphosphine (SP-15002B154, 3 mmol/g) were added and the mixture allowed to reach RT within 5 hrs. The resin was then filtered off, washed with dichloromethane and stirred 8 hrs in toluene at 100° C. Removal of the resin by filtration and evaporation of the solvent gave 70 mg (28%) of N-cyclohexyl-2-[2-(2,3-dimethoxy-phenyl)-benzoimidazol-1-yl]-4-phenyl-butyramide as a brown solid, MS (ES+): 498 (M+H).

Example 29

2-[2-(3-cyano-phenyl)-benzoimidazol-1-yl]-2,N-dicyclohexyl-acetamide

In analogy to examples 2.1-2.2, 3-cyano benzoic acid, cyclohexanecarbaldehyde, cyclohexyl isocyanide, and N-tert-butoxycarbonyl phenylene diamine gave 2-[2-(3-cyano-phenyl)-benzoimidazol-1-yl]-2,N-dicyclohexyl-acetamide as a white solid, MS (ES+): 441 (M+H).

Example 30

2,N-dicyclohexyl-2-{2-[4-(1H-tetrazol-5-yl)-phenyl]-benzoimidazol-1-yl}-acetamide hydrogen chloride In analogy to examples 3.1-3.2, 4-(1H-tetrazol-5-yl)-benzoic acid, cyclohexanecarbaldehyde, cyclohexyl isocyanide, and N-tert-butoxycarbonyl phenylene diamine gave 2,N-Dicyclohexyl-2-{2-[4-(1H-tetrazol-5-yl)-phenyl]-benzoimidazol-1-yl}-acetamide hydrogen chloride as an off-white solid, MS (ES+): 484 (M+H).

Example 31

3-[1-(benzylcarbamoyl-cyclopentyl-methyl)-1H-benzoimidazol-2-yl]-benzoic acid methyl ester In analogy to examples 2.1-2.2, 3-methoxycarbonyl-benzoic acid, cyclopentanecarbaldehyde, benzyl isocyanide, and N-tert-butoxycarbonyl phenylene diamine gave 3-[1-(benzylcarbamoyl-cyclopentyl-methyl)-1H-benzoimidazol-2-yl]-benzoic acid methyl ester as a white solid, MS (ES+): 468 (M+H).

Example 32

2-[2-(2,4-dimethoxy-phenyl)-benzoimidazol-1-yl]-hexanoic acid cyclohexylamide

In analogy to example 28.3, 2,3-dimethoxy-benzoic acid, pentanal, cyclohexyl isocyanide, and 2-azido-phenylamine gave 2-[2-(2,4-dimethoxy-phenyl)-benzoimidazol-1-yl]-hexanoic acid cyclohexylamide, MS (ES+): 450 (M+H).

Example 33

2,N-dicyclohexyl-2-[2-(3-methanesulfonyl-phenyl)-benzoimidazol-1-yl]-acetamide hydrogen chloride In analogy to examples 3.1-3.2, 3-methanesulfonyl-benzoic acid, cyclohexanecarbaldehyde, cyclohexyl isocyanide, and N-tert-butoxycarbonyl phenylene diamine gave 2,N-dicyclohexyl-2-[2-(3-methanesulfonyl-phenyl)-benzoimidazol-1-yl]-acetamide hydrogen chloride as a brown solid, MS (ES+): 494 (M+H).

Example 34

N-benzyl-2-cyclohexyl-2-[2-(2,4-dimethoxy-phenyl)-benzoimidazol-1-yl]-acetamide

In analogy to examples 2.1-2.2, 2,4-dimethoxy-benzoic acid, cyclohexanecarbaldehyde, benzylisocyanide, and N-tert-butoxycarbonyl phenylene diamine gave N-benzyl-2-cyclohexyl-2-[2-(2,4-dimethoxy-phenyl)-benzoimidazol-1-yl]-acetamide as a yellow oil, MS (ES+): 484 (M+H).

Example 35

2-cyclohexyl-2-[2-(2,4-dimethoxy-phenyl)-benzoimidazol-1-yl]-N-(1-methyl-butyl)-acetamide In analogy to examples 2.1-2.2, 2,4-dimethoxy-benzoic acid, cyclohexanecarbaldehyde, 2-isocyanopentane, and N-tert-butoxycarbonyl phenylene diamine gave 2-cyclohexyl-2-[2-(2,4-dimethoxy-phenyl)-benzoimidazol-1-yl]-N-(1-methyl-butyl)-acetamide as an orange solid, MS (ES+): 464 (M+H).

Example 36

4-[1-(benzylcarbamoyl-cyclopentyl-methyl)-1H-benzoimidazol-2-yl]-benzoic acid methyl ester In analogy to examples 2.1-2.2, 4-methoxycarbonyl-benzoic acid, cyclopentanecarbaldehyde, benzyl isocyanide, and N-tert-butoxycarbonyl phenylene diamine gave 4-[1-(benzylcarbamoyl-cyclopentyl-methyl)-1H-benzoimidazol-2-yl]-benzoic acid methyl ester as a white solid, MS (ES+): 468 (M+H).

Example 37

N-cyclopentyl-2-[2-(3-methoxy-phenyl)-benzoimidazol-1-yl]-4-phenyl-butyramide hydrogen chloride In analogy to examples 3.1-3.2, 3-methoxy-benzoic acid, 3-phenylpropanal, cyclopentyl isocyanide, and N-tert-butoxycarbonyl phenylene diamine gave N-cyclopentyl-2-[2-(3-methoxy-phenyl)-benzoimidazol-1-yl]-4-phenyl-butyramide hydrogen chloride as a brown solid, MS (ES+): 454 (M+H).

Example 38

2,N-dicyclohexyl-2-[2-(2,4-dimethoxy-phenyl)-5-methyl-benzoimidazol-1-yl]-acetamide hydrogen chloride In analogy to examples 3.1-3.2, 2,4-dimethoxy-benzoic acid, cyclohexanecarbaldehyde, cyclohexylisocyanide, and N-tert-butoxycarbonyl 5-methyl phenylene diamine gave 2,N-dicyclohexyl-2-[2-(2,4-dimethoxy-phenyl)-5-methyl-benzoimidazol-1-yl]-acetamide hydrogen chloride as a white solid, MS (ES+): 490 (M+H).

Example 39

2-[2-(4-chloro-phenyl)-benzoimidazol-1-yl]-2,N-dicyclopentyl-acetamide hydrogen chloride In analogy to examples 3.1-3.2, 4-chloro-benzoic acid, cyclopentanecarbaldehyde, cyclopentylisocyanide, and N-tert-butoxycarbonyl phenylene diamine gave 2-[2-(4-chloro-phenyl)-benzoimidazol-1-yl]-2,N-dicyclopentyl-acetamide hydrogen chloride as a white solid, MS (ES+): 422 (M+H).

Example 40

N-benzhydryl-2-cyclohexyl-2-[2-(2,4-dimethoxy-phenyl)-benzoimidazol-1-yl]-acetamide In analogy to examples 2.1-2.2, 2,4-dimethoxy-benzoic acid, cyclohexanecarbaldehyde, diphenylmethylisocyanide, and N-tert-butoxycarbonyl phenylene diamine gave N-benzhydryl-2-cyclohexyl-2-[2-(2,4-dimethoxy-phenyl)-benzoimidazol-1-yl]-acetamide as a brown solid, MS (ES+): 560 (M+H).

Example 41

N-benzyl-2-(2-naphthalen-1-yl-benzoimidazol-1-yl)-4-phenyl-butyramide

In analogy to examples 2.1-2.2, naphthalene-1-carboxylic acid, 3-phenylpropanal, benzyl isocyanide, and N-tert-butoxycarbonyl phenylene diamine gave N-benzyl-2-(2-naphthalen-1-yl-benzoimidazol-1-yl)-4-phenyl-butyramide as a white solid, MS (ES+): 496 (M+H).

Example 42

2-cyclohexyl-2-[2-(2,4-dimethoxy-phenyl)-benzoimidazol-1-yl]-N-(4-methoxy-phenyl)-acetamide In analogy to examples 2.1-2.2, 2,4-dimethoxy-benzoic acid, cyclohexanecarbaldehyde, 4-methoxyphenylisocyanide, and N-tert-butoxycarbonyl phenylene diamine gave 2-cyclohexyl-2-[2-(2,4-dimethoxy-phenyl)-benzoimidazol-1-yl]-N-(4-methoxy-phenyl)-acetamide as a yellow oil, MS (ES+): 500 (M+H).

Example 43

2,N-dicyclohexyl-2-[2-(2,4-dimethoxy-phenyl)-4-methyl-benzoimidazol-1-yl]-acetamide In analogy to examples 2.1-2.2, 2,4-dimethoxy-benzoic acid, cyclohexanecarbaldehyde, cyclohexylisocyanide, and N-tert-butoxycarbonyl 6-methyl phenylene diamine gave 2,N-dicyclohexyl-2-[2-(2,4-dimethoxy-phenyl)-4-methyl-benzoimidazol-1-yl]-acetamide as a brown solid, MS (ES+): 490 (M+H).

Example 44

2,N-dicyclohexyl-2-{2-[3-(2-oxo-pyrrolidin-1-yl)-phenyl]-benzoimidazol-1-yl}-acetamide hydrogen chloride In analogy to examples 3.1-3.2, 3-(2-oxo-pyrrolidin-1-yl)-benzoic acid, cyclohexanecarbaldehyde, cyclohexylisocyanide, and N-tert-butoxycarbonyl phenylene diamine gave 2,N-dicyclohexyl-2-{2-[3-(2-oxo-pyrrolidin-1-yl)-phenyl]-benzoimidazol-1-yl}-acetamide hydrogen chloride as a white solid, MS (ES+): 499 (M+H).

Example 45

2,N-dicyclohexyl-2-[2-(2-oxo-1,2-dihydro-pyridin-4-yl)-benzoimidazol-1-yl]-acetamide In analogy to examples 2.1-2.2, 2-methoxy-isonicotinic acid, cyclohexanecarbaldehyde, cyclohexylisocyanide, and N-tert-butoxycarbonyl phenylene diamine gave, in a process accompanied by hydrolysis of the 2-methoxypyridino moiety to a 2-oxo-1,2-dihydro-pyridino moiety, 2,N-dicyclohexyl-2-[2-(2-oxo-1,2-dihydro-pyridin-4-yl)-benzoimidazol-1-yl]-acetamide as an off-white solid, MS (ES+): 433 (M+H).

Example 46

N-cyclopentyl-2-[2-(2-methoxy-phenyl)-benzoimidazol-1-yl]-4-phenyl-butyramide

In analogy to examples 2.1-2.2, 2-methoxy benzoic acid, 3-phenylpropanal, cyclopentyl isocyanide, and N-tert-butoxycarbonyl phenylene diamine gave N-cyclopentyl-2-[2-(2-methoxy-phenyl)-benzoimidazol-1-yl]-4-phenyl-butyramide as a white solid, MS (ES+): 454 (M+H).

Example 47

2-cyclohexyl-2-[2-(2,4-dimethoxy-phenyl)-benzoimidazol-1-yl]-N-pentyl-acetamide

In analogy to examples 2.1-2.2, 2,4-dimethoxy-benzoic acid, cyclohexanecarbaldehyde, pentylisocyanide, and N-tert-butoxycarbonyl phenylene diamine gave 2-cyclohexyl-2-[2-(2,4-dimethoxy-phenyl)-benzoimidazol-1-yl]-N-pentyl-acetamide as a white solid, MS (ES+): 464 (M+H).

Example 48

N-benzyl-2-[2-(4-chloro-phenyl)-benzoimidazol-1-yl]-2-cyclopentyl-acetamide hydrogen chloride In analogy to examples 3.1-3.2, 4-chlorobenzoic acid, cyclopentanecarbaldehyde, benzylisocyanide, and N-tert-butoxycarbonyl phenylene diamine gave N-benzyl-2-[2-(4-chloro-phenyl)-benzoimidazol-1-yl]-2-cyclopentyl-acetamide hydrogen chloride as a brown solid, MS (ES+): 444 (M+H).

Example 49

2,N-dicyclopentyl-2-(2-naphthalene-1-yl-benzoimidazol-1-yl)-acetamide

In analogy to examples 2.1-2.2, naphthalene-1-carboxylic acid, cyclopentanecarbaldehyde, cyclopentylisocyanide, and N-tert-butoxycarbonyl phenylene diamine gave 2,N-dicyclopentyl-2-(2-naphthalen-1-yl-benzoimidazol-1-yl)-acetamide as a white solid, MS (ES+): 438 (M+H).

Example 50

2-[2-(3-cyano-phenyl)-benzoimidazol-1-yl]-N-cyclohexyl-4-phenyl-butyramide

In analogy to example 28.3, 3-cyanobenzoic acid, 3-phenylpropanal, cyclohexylisocyanide, and 2-azido-phenylamine gave 2-[2-(3-cyano-phenyl)-benzoimidazol-1-yl]-N-cyclohexyl-4-phenyl-butyramide, MS (ES+): 463 (M+H).

Example 51

2-[2-(4-hydroxy-phenyl)-benzoimidazol-1-yl]-4-methyl-pentanoic acid cyclohexylamide hydrogen chloride In analogy to examples 3.1-3.2, 4-hydroxybenzoic acid, 3-methylbutyraldehyde, cyclohexylisocyanide, and N-tert-butoxycarbonyl phenylene diamine gave 2-[2-(4-hydroxy-phenyl)-benzoimidazol-1-yl]-4-methyl-pentanoic acid cyclohexylamide hydrogen chloride as a brown solid, MS (ES+): 406 (M+H).

Example 52

N-tert-butyl-2-cyclohexyl-2-[2-(2,4-dimethoxy-phenyl)-benzoimidazol-1-yl]-acetamide In analogy to examples 2.1-2.2, 2,4-dimethoxy-benzoic acid, cyclohexane carbaldehyde, tert-butylisocyanide, and N-tert-butoxycarbonyl phenylene diamine gave N-tert-butyl-2-cyclohexyl-2-[2-(2,4-dimethoxy-phenyl)-benzoimidazol-1-yl]-acetamide as a white solid, MS (ES+): 450 (M+H).

Example 53

4-[1-(1-benzylcarbamoyl-3-phenyl-propyl)-1H-benzoimidazol-2-yl]-benzoic acid methyl ester In analogy to examples 2.1-2.2, terephthalic acid monomethylester, 3-phenylpropanal, benzylisocyanide, and N-tert-butoxycarbonyl phenylene diamine gave 4-[1-(1-benzylcarbamoyl-3-phenyl-propyl)-1H-benzoimidazol-2-yl]-benzoic acid methyl ester as a white solid, MS (ES+): 504 (M+H).

Example 54

4-[1-(1-cyclohexylcarbamoyl-3-phenyl-propyl)-1H-benzoimidazol-2-yl]-benzoic acid methyl ester In analogy to example 28.3, terephthalic acid monomethylester, 3-phenylpropanal, cyclohexyl isocyanide, and 2-azido-phenylamine gave 4-[1-(1-benzylcarbamoyl-3-phenyl-propyl)-1H-benzoimidazol-2-yl]-benzoic acid methyl ester as a brown solid, MS (ES+): 496 (M+H).

Example 55

2,N-dicyclopentyl-2-[2-(2-methoxy-phenyl)-benzoimidazol-1-yl]-acetamide

In analogy to examples 2.1-2.2, 2-methoxy benzoic acid, cyclopentanecarbaldehyde, cyclopentyl isocyanide, and N-tert-butoxycarbonyl phenylene diamine gave 2,N-dicyclopentyl-2-[2-(2-methoxy-phenyl)-benzoimidazol-1-yl]-acetamide as cream solid, MS (ES+): 418 (M+H).

Example 56

2,N-dicyclohexyl-2-[2-(2,4-dimethoxy-phenyl)-naphtho[2,3-d]imidazol-1-yl]-acetamide In analogy to examples 2.1-2.2, 2,4-dimethoxy-benzoic acid, cyclohexanecarbaldehyde, cyclohexylisocyanide, and (3-amino-naphthalen-2-yl)-carbamic acid tert-butyl ester gave 2,N-dicyclohexyl-2-[2-(2,4-dimethoxy-phenyl)-naphtho[2,3-d]imidazol-1-yl]-acetamide as a yellow solid, MS (ES+): 526 (M+H).

Example 57

2-[2-(2,3-dimethoxy-phenyl)-benzoimidazol-1-yl]-4-methyl-pentanoic acid cyclohexylamide In analogy to example 28.3, 2,3-dimethoxy benzoic acid, 3-methyl butanal, cyclohexyl isocyanide, and 2-azido-phenylamine gave 2-[2-(2,3-dimethoxy-phenyl)-benzoimidazol-1-yl]-4-methyl-pentanoic acid cyclohexylamide, MS (ES+): 450 (M+H).

Example 58

N-benzyl-2-[2-(2-methoxy-phenyl)-benzoimidazol-1-yl]-4-phenyl-butyramide

In analogy to examples 2.1-2.2, 2-methoxy benzoic acid, 3-phenylpropanal, benzylisocyanide, and N-tert-butoxycarbonyl phenylene diamine gave N-benzyl-2-[2-(2-methoxy-phenyl)-benzoimidazol-1-yl]-4-phenyl-butyramide as a white solid, MS (ES+): 476 (M+H).

Example 59

2-cyclohexyl-2-[2-(2,4-dimethoxy-phenyl)-benzoimidazol-1-yl]-N-(3-isopropoxy-propyl)-acetamide In analogy to examples 2.1-2.2, 2,4-dimethoxy benzoic acid, cyclohexanecarbaldehyde, 1-isocyano-3-isopropoxy-propane, and N-tert-butoxycarbonyl phenylene diamine gave 2-cyclohexyl-2-[2-(2,4-dimethoxy-phenyl)-benzoimidazol-1-yl]-N-(3-isopropoxy-propyl)-acetamide as a colorless oil, MS (ES+): 494 (M+H).

Example 60

2-[2-(2,4-dimethoxy-phenyl)-benzoimidazol-1-yl]-N-isopropyl-4-phenyl-butyramide

In analogy to example 28.3, 2,4-dimethoxy benzoic acid, 3-phenylpropanal, isopropyl isocyanide, and 2-azido-phenylamine gave 2-[2-(2,4-dimethoxy-phenyl)-benzoimidazol-1-yl]-N-isopropyl-4-phenyl-butyramide, MS (ES+): 458 (M+H).

Example 61

N-benzyl-2-cyclopentyl-2-(2-naphthalen-1-yl-benzoimidazol-1-yl)-acetamide

In analogy to examples 2.1-2.2, naphthalene-1-carboxylic acid, cyclopentanecarbaldehyde, benzylisocyanide, and N-tert-butoxycarbonyl phenylene diamine gave N-benzyl-2-cyclopentyl-2-(2-naphthalen-1-yl-benzoimidazol-1-yl)-acetamide as a white solid, MS (ES+): 460 (M+H).

Example 62

2,N-dicyclohexyl-2-[2-(2,3-dimethoxy-phenyl)-benzoimidazol-1-yl]-acetamide

In analogy to example 28.3, 2,3-dimethoxy benzoic acid, cyclohexanecarbaldehyde, cyclohexyl isocyanide, and 2-azido-phenylamine gave 2,N-dicyclohexyl-2-[2-(2,3-dimethoxy-phenyl)-benzoimidazol-1-yl]-acetamide, MS (ES+): 476 (M+H).

Example 63

2-[2-(2,4-dimethoxy-phenyl)-benzoimidazol-1-yl]-4-methyl-pentanoic acid cyclohexylamide In analogy to example 28.3, 2,4-dimethoxy benzoic acid, 3-methyl butanal, cyclohexyl isocyanide, and 2-azido-phenylamine gave 2-[2-(2,4-dimethoxy-phenyl)-benzoimidazol-1-yl]-4-methyl-pentanoic acid cyclohexylamide, MS (ES+): 450 (M+H).

Example 64

2-cyclohexyl-2-[2-(2,3-dimethoxy-phenyl)-benzoimidazol-1-yl]-N-isopropyl-acetamide In analogy to example 28.3, 2,3-dimethoxy benzoic acid, cyclohexanecarbaldehyde, isopropyl isocyanide, and 2-azido-phenylamine gave 2-cyclohexyl-2-[2-(2,3-dimethoxy-phenyl)-benzoimidazol-1-yl]-N-isopropyl-acetamide, MS (ES+): 436 (M+H).

Example 65

2-[2-(2,3-dimethoxy-phenyl)-benzoimidazol-1-yl]-N-isopropyl-4-phenyl-butyramide

In analogy to example 28.3, 2,3-dimethoxy benzoic acid, 3-phenylpropanal, isopropyl isocyanide, and 2-azido-phenylamine gave 2-[2-(2,3-dimethoxy-phenyl)-benzoimidazol-1-yl]-N-isopropyl-4-phenyl-butyramide, MS (ES+): 458 (M+H).

Example 66

2-[2-(4-Acetyl-phenyl)-benzoimidazol-1-yl]-N-cyclohexyl-4-phenyl-butyramide

In analogy to example 28.3, 2,4-acetyl benzoic acid, 3-phenylpropanal, cyclohexyl isocyanide, and 2-azido-phenylamine gave 2-[2-(4-Acetyl-phenyl)-benzoimidazol-1-yl]-N-cyclohexyl-4-phenyl-butyramide, MS (ES+): 480 (M+H).

Example 67

N-benzyl-2-[2-(4-chloro-phenyl)-benzoimidazol-1-yl]-4-phenyl-butyramide hydrogen chloride In analogy to examples 3.1-3.2, 4-chloro benzoic acid, 3-phenylpropanal, benzylisocyanide, and N-tert-butoxycarbonyl phenylene diamine gave N-benzyl-2-[2-(4-chloro-phenyl)-benzoimidazol-1-yl]-4-phenyl-butyramide hydrogen chloride as a white solid, MS (ES+): 480 (M+H).

Example 68

4-[1-(1-isopropylcarbamoyl-pentyl)-1H-benzoimidazol-2-yl]-benzoic acid methyl ester In analogy to example 28.3, terephthalic acid monomethylester, pentanal, isopropylisocyanide, and 2-azido-phenylamine gave 4-[1-(1-isopropylcarbamoyl-pentyl)-1H-benzoimidazol-2-yl]-benzoic acid methyl ester, MS (ES+): 408 (M+H).

Example 69

N-butyl-2-[2-(2,4-dimethoxy-phenyl)-benzoimidazol-1-yl]-2-phenyl-acetamide

In analogy to example 28.3, 2,4-dimethoxy benzoic acid, benzaldehyde, butylisocyanide, and 2-azido-phenylamine gave N-butyl-2-[2-(2,4-dimethoxy-phenyl)-benzoimidazol-1-yl]-2-phenyl-acetamide, MS (ES+): 444 (M+H).

Example 70

2-[2-(2,3-dimethoxy-phenyl)-benzoimidazol-1-yl]-4-methyl-pentanoic acid isopropylamide In analogy to example 28.3, 2,3-dimethoxy benzoic acid, 3-methylbutanal, isopropylisocyanide, and 2-azido-phenylamine gave 2-[2-(2,3-dimethoxy-phenyl)-benzoimidazol-1-yl]-4-methyl-pentanoic acid isopropylamide, MS (ES+): 410 (M+H).

Example 71

2-benzo[1,3]dioxol-5-yl-N-butyl-2-[2-(2,3-dimethoxy-phenyl)-benzoimidazol-1-yl]-acetamide In analogy to example 28.3, 2,3-dimethoxy benzoic acid, benzo[1,3]dioxole-5-carbaldehyde, butylisocyanide, and 2-azido-phenylamine gave 2-benzo[1,3]dioxol-5-yl-N-butyl-2-[2-(2,3-dimethoxy-phenyl)-benzoimidazol-1-yl]-acetamide, MS (ES+): 488 (M+H).

Example 72

2-benzo[1,3]dioxol-5-yl-N-butyl-2-[2-(2,4-dimethoxy-phenyl)-benzoimidazol-1-yl]-acetamide In analogy to example 28.3, 2,4-dimethoxy benzoic acid, benzo[1,3]dioxole-5-carbaldehyde, butylisocyanide, and 2-azido-phenylamine gave 2-benzo[1,3]dioxol-5-yl-N-butyl-2-[2-(2,3-dimethoxy-phenyl)-benzoimidazol-1-yl]-acetamide, MS (ES+): 488 (M+H).

Example 73

N-butyl-2-[2-(2,4-dimethoxy-phenyl)-benzoimidazol-1-yl]-2-(2-fluoro-phenyl)-acetamide In analogy to example 28.3, 2,4-dimethoxy benzoic acid, 2-fluorobenzaldehyde, butylisocyanide, and 2-azido-phenylamine gave N-butyl-2-[2-(2,4-dimethoxy-phenyl)-benzoimidazol-1-yl]-2-(2-fluoro-phenyl)-acetamide, MS (ES+): 462 (M+H).

Example 74

N-cyclopentyl-2-[2-(3-hydroxy-phenyl)-benzoimidazol-1-yl]-4-phenyl-butyramide

In analogy to examples 2.1-2.2, 3-hydroxybenzoic acid, 3-phenyl propanal, cyclopentylisocyanide, and N-tert-butoxycarbonyl phenylene diamine gave N-cyclopentyl-2-[2-

(3-hydroxy-phenyl)-benzoimidazol-1-yl]-4-phenyl-butyramide hydrogen chloride as a white solid, MS (ES+): 440 (M+H).

Example 75

2-[2-(4-acetyl-phenyl)-benzoimidazol-1-yl]-hexanoic acid isopropylamide

In analogy to example 28.3, 4-acetyl benzoic acid, pentanal, isopropyl isocyanide, and 2-azido-phenylamine gave 2-[2-(4-acetyl-phenyl)-benzoimidazol-1-yl]-hexanoic acid isopropylamide, MS (ES+): 392 (M+H).

Example 76

N-butyl-2-[2-(2,3-dimethoxy-phenyl)-benzoimidazol-1-yl]-2-phenyl-acetamide

In analogy to example 28.3, 2,3-dimethoxy benzoic acid, benzaldehyde, butylisocyanide, and 2-azido-phenylamine gave N-butyl-2-[2-(2,3-dimethoxy-phenyl)-benzoimidazol-1-yl]-2-phenyl-acetamide as a brown solid. MS (ES+): 444 (M+H).

Example 77

2-[2-(4-acetyl-phenyl)-benzoimidazol-1-yl]-4-methyl-pentanoic acid cyclohexylamide In analogy to example 28.3, 4-acetyl benzoic acid, 3-methylbutanal, cyclohexyl isocyanide, and 2-azido-phenylamine gave 2-[2-(4-acetyl-phenyl)-benzoimidazol-1-yl]-4-methyl-pentanoic acid cyclohexylamide, MS (ES+): 432 (M+H).

Example 78

N-butyl-2-[2-(2,3-dimethoxy-phenyl)-benzoimidazol-1-yl]-2-o-tolyl-acetamide

In analogy to example 28.3, 2,3-dimethoxy benzoic acid, 2-methylbenzaldehyde, butylisocyanide, and 2-azido-phenylamine gave N-butyl-2-[2-(2,3-dimethoxy-phenyl)-benzoimidazol-1-yl]-2-o-tolyl-acetamide, MS (ES+): 458 (M+H).

Example 79

N-butyl-2-[2-(2,3-dimethoxy-phenyl)-benzoimidazol-1-yl]-2-(4-methoxy-phenyl)-acetamide In analogy to example 28.3, 2,3-dimethoxybenzoic acid, 4-methoxybenzaldehyde, butylisocyanide, and 2-azido-phenylamine gave N-butyl-2-[2-(2,3-dimethoxy-phenyl)-benzoimidazol-1-yl]-2-(4-methoxy-phenyl)-acetamide, MS (ES+): 474 (M+H).

Example 80

N-butyl-2-[2-(2,3-dimethoxy-phenyl)-benzoimidazol-1-yl]-2-(2-fluoro-phenyl)-acetamide In analogy to example 28.3, 2,3-dimethoxybenzoic acid, 2-fluorobenzaldehyde, butylisocyanide, and 2-azido-phenylamine gave N-butyl-2-[2-(2,3-dimethoxy-phenyl)-benzoimidazol-1-yl]-2-(2-fluoro-phenyl)-acetamide, MS (ES+): 462 (M+H).

Example 81

N-butyl-2-[2-(2,3-dimethoxy-phenyl)-benzoimidazol-1-yl]-2-(4-dimethylamino-phenyl)-acetamide In analogy to example 28.3, 2,3-dimethoxybenzoic acid, 4-dimethylaminobenzaldehyde, butylisocyanide, and 2-azido-phenylamine gave N-butyl-2-[2-(2,3-dimethoxy-phenyl)-benzoimidazol-1-yl]-2-(4-dimethylamino-phenyl)-acetamide, MS (ES+): 487 (M+H).

Example 82

2-[2-(2,3-dimethoxy-phenyl)-benzoimidazol-1-yl]-hexanoic acid isopropylamide

In analogy to example 28.3, 2,3-dimethoxybenzoic acid, pentanal, isopropylisocyanide, and 2-azido-phenylamine gave 2-[2-(2,3-dimethoxy-phenyl)-benzoimidazol-1-yl]-hexanoic acid isopropylamide, MS (ES+): 410 (M+H).

Example 83

4-{1-[(2-fluoro-phenyl)-isopropylcarbamoyl-methyl]-1H-benzoimidazol-2-yl}-benzoic acid methyl ester In analogy to example 28.3, terephthalic acid monomethylester, 2-fluorobenzaldehyde, isopropylisocyanide, and 2-azido-phenylamine gave 4-{1-[(2-fluoro-phenyl)-isopropylcarbamoyl-methyl]-1H-benzoimidazol-2-yl}-benzoic acid methyl ester, MS (ES+): 446 (M+H).

Example 84

2-[2-(3-cyano-phenyl)-benzoimidazol-1-yl]-4-methyl-pentanoic acid cyclohexylamide In analogy to example 28.3, 3-cyano benzoic acid, 3-methylbutanal, cyclohexyl isocyanide, and 2-azido-phenylamine gave 2-[2-(3-cyano-phenyl)-benzoimidazol-1-yl]-4-methyl-pentanoic acid cyclohexylamide, MS (ES+): 415 (M+H).

Example 85

2-[2-(3-chloro-phenyl)-benzoimidazol-1-yl]-4-methyl-pentanoic acid cyclohexylamide In analogy to example 28.3, 3-chloro benzoic acid, 3-methylbutanal, cyclohexyl isocyanide, and 2-azido-phenylamine gave 2-[2-(3-chloro-phenyl)-benzoimidazol-1-yl]-4-methyl-pentanoic acid cyclohexylamide, MS (ES+): 415 (M+H).

Example 86

N-butyl-2-[2-(2,4-dimethoxy-phenyl)-benzoimidazol-1-yl]-2-(4-methoxy-phenyl)-acetamide In analogy to example 28.3, 2,4-dimethoxy benzoic acid, 4-methoxybenzaldehyde, butylisocyanide, and 2-azido-phenylamine gave N-butyl-2-[2-(2,4-dimethoxy-phenyl)-benzoimidazol-1-yl]-2-(4-methoxy-phenyl)-acetamide, MS (ES+): 474 (M+H).

Example 87

N-benzyl-2-[2-(3-methoxy-phenyl)-benzoimidazol-1-yl]-4-phenyl-butyramide hydrogen chloride In analogy to examples 3.1-3.2, 3-methoxy benzoic acid, 3-phenylpropanal, benzylisocyanide, and N-tert-butoxycarbonyl phenylene diamine gave N-benzyl-2-[2-(3-methoxy-phenyl)-benzoimidazol-1-yl]-4-phenyl-butyramide hydrogen chloride as a brown solid, MS (ES+): 476 (M+H).

Example 88

2-(4-chloro-phenyl)-2-[2-(2,3-dimethoxy-phenyl)-benzoimidazol-1-yl]-N-isopropyl-acetamide In analogy to example 28.3, 2,3-dimethoxybenzoic acid, 4-chlorobenzaldehyde, isopropylisocyanide, and 2-azido-phenylamine gave 2-(4-chloro-phenyl)-2-[2-(2,3-dimethoxy-phenyl)-benzoimidazol-1-yl]-N-isopropyl-acetamide, MS (ES+): 464 (M+H).

Example 89

N-butyl-2-[2-(2,4-dimethoxy-phenyl)-benzoimidazol-1-yl]-2-(4-dimethylamino-phenyl)-acetamide In analogy to example 28.3, 2,4-dimethoxybenzoic acid, 4-dimethylaminobenzaldehyde, butylisocyanide, and 2-azido-phenylamine gave N-butyl-2-[2-(2,4-dimethoxy-phenyl)-benzoimidazol-1-yl]-2-(4-dimethylamino-phenyl)-acetamide, MS (ES+): 487 (M+H).

Example 90

2-[2-(4-hydroxy-phenyl)-benzoimidazol-1-yl]-N-isopropyl-4-phenyl-butyramide

In analogy to example 28.3, 4-hydroxybenzoic acid, 3-phenylpropanal, isopropylisocyanide, and 2-azido-phenylamine gave 2-[2-(4-hydroxy-phenyl)-benzoimidazol-1-yl]-N-isopropyl-4-phenyl-butyramide, MS (ES+): 414 (M+H).

Example 91

2-[2-(4-hydroxy-phenyl)-benzoimidazol-1-yl]-4-methyl-pentanoic acid cyclohexylamide In analogy to example 28.3, 4-hydroxybenzoic acid, 3-methylpropanal, cyclohexylisocyanide, and 2-azido-phenylamine gave 2-[2-(4-hydroxy-phenyl)-benzoimidazol-1-yl]-4-methyl-pentanoic acid cyclohexylamide, MS (ES+): 406 (M+H).

Example 92

2-[2-(3-chloro-phenyl)-benzoimidazol-1-yl]-N-isopropyl-4-phenyl-butyramide

In analogy to example 28.3, 3-chlorobenzoic acid, 3-phenylpropionaldehyde, isopropylisocyanide, and 2-azido-phenylamine gave 2-[2-(3-chloro-phenyl)-benzoimidazol-1-yl]-N-isopropyl-4-phenyl-butyramide, MS (ES+): 432 (M+H).

Example 93

N-butyl-2-(4-chloro-phenyl)-2-[2-(2,4-dimethoxy-phenyl)-benzoimidazol-1-yl]-acetamide In analogy to example 28.3, 2,4-dimethoxybenzoic acid, 4-chlorobenzaldehyde, butylisocyanide, and 2-azido-phenylamine gave N-butyl-2-(4-chloro-phenyl)-2-[2-(2,4-dimethoxy-phenyl)-benzoimidazol-1-yl]-acetamide, MS (ES+): 478 (M+H).

Example 94

2-[2-(3-cyano-phenyl)-benzoimidazol-1-yl]-N-isopropyl-4-phenyl-butyramide

In analogy to example 28.3, 3-cyanobenzoic acid, 3-phenyl propionaldehyde, isopropylisocyanide, and 2-azido-phenylamine gave 2-[2-(3-cyano-phenyl)-benzoimidazol-1-yl]-N-isopropyl-4-phenyl-butyramide, MS (ES+): 423 (M+H).

Example 95

2-[2-(4-acetyl-phenyl)-benzoimidazol-1-yl]-N-isopropyl-2-(4-methoxy-phenyl)acetamide In analogy to example 28.3, 4-acetylbenzoic acid, 4-methoxybenzaldehyde, isopropylisocyanide, and 2-azido-phenylamine gave 2-[2-(4-acetyl-phenyl)-benzoimidazol-1-yl]-N-isopropyl-2-(4-methoxy-phenyl)acetamide, MS (ES+): 442 (M+H).

Example 96

4-{1-[isopropylcarbamoyl-(4-methoxy-phenyl)-methyl]-1H-benzoimidazol-2-yl}-benzoic acid methyl ester In analogy to example 28.3, terephthalic acid monomethylester, 4-methoxybenzaldehyde, isopropylisocyanide, and 2-azido-phenylamine gave 4-{1-[isopropylcarbamoyl-(4-methoxy-phenyl)-methyl]-1H-benzoimidazol-2-yl}-benzoic acid methyl ester, MS (ES+): 458 (M+H).

Example 97

4-[1-(isopropylcarbamoyl-phenyl-methyl)-1H-benzoimidazol-2-yl]-benzoic acid methyl ester In analogy to example 28.3, terephthalic acid monomethylester, benzaldehyde, isopropylisocyanide, and 2-azido-phenylamine gave 4-[1-(isopropylcarbamoyl-phenyl-methyl)-1H-benzoimidazol-2-yl]-benzoic acid methyl ester, MS (ES+): 428 (M+H).

Example 98

N-isopropyl-2-[2-(1-methyl-1H-pyrrol-2-yl)-benzoimidazol-1-yl]-4-phenyl-butyramide In analogy to example 28.3, 1-methyl-1H-pyrrole-2-carboxylic acid, 3-phenyl propanal, isopropylisocyanide, and 2-azido-phenylamine gave N-isopropyl-2-[2-(1-methyl-1H-pyrrol-2-yl)-benzoimidazol-1-yl]-4-phenyl-butyramide, MS (ES+): 401 (M+H).

Example 99

2-[2-(3-cyano-phenyl)-benzoimidazol-1-yl]-hexanoic acid isopropylamide

In analogy to example 28.3, 3-cyano benzoic acid, pentanal, isopropylisocyanide, and 2-azido-phenylamine gave 2-[2-(3-cyano-phenyl)-benzoimidazol-1-yl]-hexanoic acid isopropylamide, MS (ES+): 375 (M+H).

Example 100

2-[2-(4-hydroxy-phenyl)-benzoimidazol-1-yl]-pentanoic acid isopropylamide

In analogy to example 28.3, 4-hydroxy benzoic acid, butanal, isopropylisocyanide, and 2-azido-phenylamine gave 2-[2-(4-hydroxy-phenyl)-benzoimidazol-1-yl]-pentanoic acid isopropylamide, MS (ES+): 352 (M+H).

Example 101

2-benzo[1,3]dioxol-5-yl-N-butyl-2-[2-(1-methyl-1H-pyrrol-2-yl)-benzoimidazol-1-yl]-acetamide In analogy to example 28.3, 1-methyl-1H-pyrrole-2-carboxylic acid, benzo[1,3]dioxole-5-carbaldehyde, butylisocyanide, and 2-azido-phenylamine gave 2-benzo[1,3]dioxol-5-yl-N-butyl-2-[2-(1-methyl-1H-pyrrol-2-yl)-benzoimidazol-1-yl]-acetamide, MS (ES+): 431 (M+H).

Example 102

2-cyclohexyl-2-[2-(2,4-dimethoxy-phenyl)-benzoimidazol-1-yl]-N-(2,6-dimethyl-phenyl)-acetamide In analogy to example 28.3, 2,4-dimethoxy benzoic acid, cyclohexanecarbaldehyde, 2-isocyano-1,3-dimethyl-benzene, and 2-azido-phenylamine gave 2-cyclohexyl-2-[2-(2,4-dimethoxy-phenyl)-benzoimidazol-1-yl]-N-(2,6-dimethyl-phenyl)-acetamide, MS (ES+): 498 (M+H).

Example 103

2,N-dicyclohexyl-2-[2-(2,4-dimethoxy-phenyl)-benzoimidazol-1-yl]-acetamide

In analogy to example 28.3, 2,4-dimethoxy benzoic acid, cyclohexanecarbaldehyde, cyclohexylisocyanide, and 2-azido-phenylamine diamine gave 2,N-dicyclohexyl-2-[2-(2,4-dimethoxy-phenyl)-benzoimidazol-1-yl]-acetamide as a colorless solid, MS (ES+): 476 (M+H).

Example 104

2-cyclohex-3-enyl-N-cyclohexyl-2-[2-(2,4-dimethoxy-phenyl)-benzoimidazol-1-yl]-acetamide In analogy to examples 2.1-2.2, 2,4-dimethoxy benzoic acid, cyclohex-3-enecarbaldehyde, cyclohexylisocyanide, and N-tert-butoxycarbonyl phenylene diamine gave 2-cyclohex-3-enyl-N-cyclohexyl-2-[2-(2,4-dimethoxy-phenyl)-benzoimidazol-1-yl]-acetamide as a colorless solid, MS (ES+): 474 (M+H).

Example 105

2-[2-(4-cyano-phenyl)-benzoimidazol-1-yl]-2,N-dicyclohexyl-acetamide hydrogen chloride In analogy to examples 3.1-3.2, 4-cyano benzoic acid, cyclohexanecarbaldehyde, cyclohexylisocyanide, and N-tert-butoxycarbonyl phenylene diamine gave 2-[2-(4-cyano-phenyl)-benzoimidazol-1-yl]-2,N-dicyclohexyl-acetamide hydrogen chloride as a brown solid, MS (ES+): 441 (M+H).

Example 106

2-cyclohexyl-N-cyclopentyl-2-[2-(2,4-dimethoxy-phenyl)-benzoimidazol-1-yl]-acetamide In analogy to examples 2.1-2.2, 2,4-dimethoxy benzoic acid, cyclohexanecarbaldehyde, cyclopentylisocyanide, and N-tert-butoxycarbonyl phenylene diamine gave 2-cyclohexyl-N-cyclopentyl-2-[2-(2,4-dimethoxy-phenyl)-benzoimidazol-1-yl]-acetamide as an off-white solid, MS (ES+): 462 (M+H).

Example 107

2,N-dicyclohexyl-2-[2-(2,4-dimethoxy-phenyl)-5,6-difluoro-benzoimidazol-1-yl]-acetamide In analogy to examples 2.1-2.2, 2,4-dimethoxy benzoic acid, cyclohexanecarbaldehyde, cyclohexylisocyanide, and (2-Amino-4,5-difluoro-phenyl)-carbamic acid tert-butyl ester gave 2,N-dicyclohexyl-2-[2-(2,4-dimethoxy-phenyl)-5,6-difluoro-benzoimidazol-1-yl]-acetamide as a white solid, MS (ES+): 512 (M+H).

Example 108

2,N-dicyclohexyl-2-[2-(2,4-dimethoxy-phenyl)-6-methyl-benzoimidazol-1-yl]-acetamide In analogy to examples 3.1-3.2, 2,4-dimethoxy benzoic acid, cyclohexanecarbaldehyde, cyclohexylisocyanide, and (2-amino-4-methyl-phenyl)-carbamic acid tert-butyl ester gave 2,N-dicyclohexyl-2-[2-(2,4-dimethoxy-phenyl)-6-methyl-benzoimidazol-1-yl]-acetamide as white solid, MS (ES+): 490 (M+H).

Example 109

2-[2-(4-chloro-phenyl)-benzoimidazol-1-yl]-2,N-dicyclohexyl-acetamide

In analogy to examples 2.1-2.2, 4-chloro benzoic acid, cyclohexanecarbaldehyde, cyclohexylisocyanide, and N-tert-butoxycarbonyl phenylene diamine gave 2-[2-(4-chloro-phenyl)-benzoimidazol-1-yl]-2,N-dicyclohexyl-acetamide as a white solid, MS (ES+): 450 (M+H).

Example 110

2,N-dicyclohexyl-2-[2-(4-sulfamoyl-phenyl)-benzoimidazol-1-yl]-acetamide hydrogen chloride In analogy to examples 3.1-3.2, 4-sulfamoyl benzoic acid, cyclohexanecarbaldehyde, cyclohexylisocyanide, and N-tert-butoxycarbonyl phenylene diamine gave 2,N-dicyclohexyl-2-[2-(4-sulfamoyl-phenyl)-benzoimidazol-1-yl]-acetamide hydrogen chloride as a brown solid, MS (ES+): 495 (M+H).

Example 111

2-cyclohexyl-2-[2-(2,4-dimethoxy-phenyl)-benzoimidazol-1-yl]-N-(1,1,3,3-tetramethyl-butyl)-acetamide In analogy to example 28.3, 2,4-dimethoxy benzoic acid, cyclohexanecarbaldehyde, 2-isocyano-2,4,4-trimethyl-pentane, and 2-azido-phenylamine gave 2-cyclohexyl-2-[2-(2,4-dimethoxy-phenyl)-benzoimidazol-1-yl]-N-(1,1,3,3-tetramethyl-butyl)-acetamide as a yellow, oil, MS (ES+): 506 (M+H).

Example 112

4-{[1-cyclopentyl-(cyclopentylcarbamoyl-methyl)]-1H-benzoimidazol-2-yl}-benzoic acid methyl ester hydrogen chloride In analogy to examples 3.1-3.2, terephthalic acid monomethylester, cyclopentanecarbaldehyde, cyclopentylisocyanide, and N-tert-butoxycarbonyl phenylene diamine gave 4-{[1-cyclopentyl-(cyclopentylcarbamoyl-methyl)]-1H-benzoimidazol-2-yl}-benzoic acid methyl ester hydrogen chloride as a white solid, MS (ES+): 446 (M+H).

Example 113

2,N-dicyclohexyl-2-(2-quinolin-6-yl-benzoimidazol-1-yl)-acetamide hydrogen chloride In analogy to examples 3.1-3.2, quinoline-6-carboxylic acid, cyclohexanecarbaldehyde, cyclohexylisocyanide, and N-tert-butoxycarbonyl phenylene diamine gave 2,N-dicyclohexyl-2-(2-quinolin-6-yl-benzoimidazol-1-yl)-acetamide acid methyl ester hydrogen chloride as a white solid, MS (ES+): 467 (M+H).

Example 114

2-[2-(4-amino-phenyl)-benzoimidazol-1-yl]-2,N-dicyclohexyl-acetamide

In analogy to examples 2.1-2.2, 2-acetamidobenzoic acid, cyclohexanecarbaldehyde, cyclohexylisocyanide, and N-tert-butoxycarbonyl phenylene diamine gave, in a process accompanied by deacetylation of the 4-acetylamino-phenyl moiety, 2-[2-(4-amino-phenyl)-benzoimidazol-1-yl]-2,N-dicyclohexyl-acetamide as a white solid, MS (ES+): 431 (M+H).

Example 115

2-[2-(2,4-dimethoxy-phenyl)-benzoimidazol-1-yl]-5-phenyl-pentanoic acid cyclohexylamide hydrogen chloride 115.1
Tetrapropylammonium perruthenate(VII) (117 mg, 0.33 mmol, 0.1 equiv.) was added to a solution of 4 methylmorpholine N-oxide (580 mg, 5.00 mmol, 1.5 equiv.) and 4-phenyl-1-butanol (500 mg, 3.33 mmol, 1.0 equiv.) in acetonitrile (30 mL). The reaction mixture was stirred for 16 hours at room temperature then filtered through celite® then through a pad of silica (5 g) which was washed with acetonitrile (20 ml). The solvent was evaporated and the crude product purified by flash column chromatography (SiO$_2$, ethyl acetate: heptane 5% to 50%) to afford crude 4-phenyl-1-butanal as a colourless oil, 62 mg (13% yield).

115.2
In analogy to examples 3.1-3.2, 2,4-dimethoxybenzoic acid, 4-phenylbutanal, cyclohexylisocyanide, and N-tert-butoxycarbonyl phenylene diamine gave 2-[2-(2,4-dimethoxy-phenyl)-benzoimidazol-1-yl]-5-phenyl-pentanoic acid cyclohexylamide hydrogen chloride as a brown solid, MS (ES+): 512 (M+H).

Example 116

4-[1-(1-cyclopentylcarbamoyl-3-phenyl-propyl)-1H-benzoimidazol-2-yl]-benzoic acid methyl ester In analogy to examples 2.1-2.2, methoxycarbonylbenzoic acid, 3-phenyl propanal, cyclopentylisocyanide, and N-tert-butoxycarbonyl phenylene diamine gave 4-[1-(1-cyclopentylcarbamoyl-3-phenyl-propyl)-1H-benzoimidazol-2-yl]-benzoic acid methyl ester as a white solid, MS (ES+): 482 (M+H).

Example 117

2,N-dicyclohexyl-2-[2-(4-dimethylsulfamoyl-phenyl)-benzoimidazol-1-yl]-acetamide hydrogen chloride In analogy to examples 3.1-3.2, 4-dimethylsulfamoylbenzoic acid, cyclohexanecarbaldehyde, cyclohexylisocyanide, and N-tert-butoxycarbonyl phenylene diamine gave 2,N-dicyclohexyl-2-[2-(4-dimethylsulfamoyl-phenyl)-benzoimidazol-1-yl]-acetamide hydrogen chloride as a brown solid, MS (ES+): 523 (M+H).

Example 118

2,N-dicyclohexyl-2-[2-(3-sulfamoyl-phenyl)-benzoimidazol-1-yl]-acetamide hydrogen chloride In analogy to examples 3.1-3.2, 3-sulfamoylbenzoic acid, cyclohexanecarbaldehyde, cyclohexylisocyanide, and N-tert-butoxycarbonyl phenylene diamine gave 2,N-dicyclohexyl-2-[2-(3-sulfamoyl-phenyl)-benzoimidazol-1-yl]-acetamide hydrogen chloride as a brown oil, MS (ES+): 495 (M+H).

Example 119

2,N-dicyclohexyl-2-{2-[3-(1H-tetrazol-5-yl)-phenyl]-benzoimidazol-1-yl}-acetamide hydrogen chloride In analogy to examples 3.1-3.2, 3-(1H-tetrazol-5-yl)-benzoic acid, cyclohexanecarbaldehyde, cyclohexylisocyanide, and N-tert-butoxycarbonyl phenylene diamine gave 2,N-dicyclohexyl-2-{2-[3-(1H-tetrazol-5-yl)-phenyl]-benzoimidazol-1-yl}-acetamide hydrogen chloride as a yellow oil, MS (ES+): 484 (M+H).

Example 120

2,N-dicyclohexyl-2-{2-[4-(1H-imidazol-2-yl)-phenyl]-benzoimidazol-1-yl}-acetamide hydrogen chloride In analogy to examples 3.1-3.2, 4-(1H-imidazol-2-yl)-benzoic acid, cyclohexanecarbaldehyde, cyclohexylisocyanide, and N-tert-butoxycarbonyl phenylene diamine gave 2,N-dicyclohexyl-2-{2-[4-(1H-imidazol-2-yl)-phenyl]-benzoimidazol-1-yl}-acetamide hydrogen chloride as a orange oil, MS (ES+): 482 (M+H).

Example 121

2,N-dicyclohexyl-2-[2-(4-imidazol-1-yl-phenyl)-benzoimidazol-1-yl]-acetamide hydrogen chloride In analogy to examples 3.1-3.2, 4-imidazol-1-yl-benzoic acid, cyclohexanecarbaldehyde, cyclohexylisocyanide, and N-tert-butoxycarbonyl phenylene diamine gave 2,N-dicyclohexyl-2-[2-(4-imidazol-1-yl-phenyl)-benzoimidazol-1-yl]-acetamide hydrogen chloride as a brown solid, MS (ES+): 482 (M+H).

Example 122

2,N-dicyclohexyl-2-[2-(4-[1,2,4]triazol-4-yl-phenyl)-benzoimidazol-1-yl]-acetamide hydrogen chloride In analogy to examples 3.1-3.2, 4-[1,2,4]triazol-4-yl-benzoic acid, cyclohexanecarbaldehyde, cyclohexylisocyanide, and N-tert-butoxycarbonyl phenylene diamine gave 2,N-dicyclohexyl-2-[2-(4-[1,2,4]triazol-4-yl-phenyl)-benzoimidazol-1-yl]-acetamide hydrogen chloride as a colorless oil, MS (ES+): 483 (M+H).

Example 123

2,N-dicyclohexyl-2-{2-[4-(1H-pyrazol-4-yl)-phenyl]-benzoimidazol-1-yl}-acetamide hydrogen chloride In analogy to examples 3.1-3.2, 4-(1H-pyrazol-4-yl)-benzoic acid, cyclohexanecarbaldehyde, cyclohexylisocyanide, and N-tert-butoxycarbonyl phenylene diamine gave 2,N-dicyclohexyl-2-{2-[4-(1H-pyrazol-4-yl)-phenyl]-benzoimidazol-1-yl}-acetamide hydrogen chloride as a colorless oil, MS (ES+): 482 (M+H).

Example 124

2,N-dicyclohexyl-2-[2-(4-[1,2,3]thiadiazol-4-yl-phenyl)-benzoimidazol-1-yl]-acetamide hydrogen chloride In analogy to examples 3.1-3.2, 4-[1,2,3]thiadiazol-4-yl-benzoic acid, cyclohexanecarbaldehyde, cyclohexylisocyanide, and N-tert-butoxycarbonyl phenylene diamine gave 2,N-dicyclohexyl-2-[2-(4-[1,2,3]thiadiazol-4-yl-phenyl)-benzoimidazol-1-yl]-acetamide hydrogen chloride as a colorless oil, MS (ES+): 500 (M+H).

Example 125

2,N-dicyclohexyl-2-[2-(1,3-dioxo-2,3-dihydro-1H-isoindol-5-yl)-benzoimidazol-1-yl]-acetamide hydrogen chloride In analogy to examples 3.1-3.2, 1,3-dioxo-2,3-dihydro-1H-isoindole-5-carboxylic acid, cyclohexanecarbaldehyde, cyclohexylisocyanide, and N-tert-butoxycarbonyl phenylene diamine gave 2,N-dicyclohexyl-2-[2-(4-[1,2,4]triazol-4-yl-phenyl)-benzoimidazol-1-yl]-acetamide hydrogen chloride as a yellow oil, MS (ES+): 485 (M+H).

Example 126

2,N-dicyclohexyl-2-[2-(3-tetrazol-1-yl-phenyl)-benzoimidazol-1-yl]-acetamide hydrogen chloride In analogy to examples 3.1-3.2, 3-tetrazol-1-yl-benzoic acid, cyclohexanecarbaldehyde, cyclohexylisocyanide, and N-tert-butoxycarbonyl phenylene diamine gave 2,N-dicyclohexyl-2-[2-(3-tetrazol-1-yl-phenyl)-benzoimidazol-1-yl]-acetamide hydrogen chloride as a colorless oil, MS (ES+): 484 (M+H).

Example 127

4-[1-(cyclohexyl-3-methoxycarbonylphenylcarbamoyl-methyl)-1H-benzoimidazol-2-yl]-benzoic acid methyl ester hydrogen chloride In analogy to examples 3.1-3.2, terephthalic acid monomethylester, cyclohexanecarbaldehyde, 3-methyoxycarbonylphenylisocyanide, and N-tert-butoxycarbonyl phenylene diamine gave 4-[1-(cyclohexyl-3-methoxycarbonylphenylcarbamoyl-methyl)-1H-benzoimidazol-2-yl]-benzoic acid methyl ester hydrogen chloride as a white solid, MS (ES+): 526 (M+H).

Example 128 trans 4-(1-{cyclohexyl-[(4-methoxycarbonyl-cyclohexylmethyl)-carbamoyl]-methyl}-1H-benzoimidazol-2-yl)-benzoic acid methyl ester hydrogen chloride In analogy to examples 3.1-3.2, terephthalic acid monomethylester, cyclohexanecarbaldehyde, trans 4-isocyanomethyl-cyclohexanecarboxylic acid methyl ester, and N-tert-butoxycarbonyl phenylene diamine gave trans 4-(1-{cyclohexyl-[(4-methoxycarbonyl-cyclohexylmethyl)-carbamoyl]-methyl}-1H-benzoimidazol-2-yl)-benzoic acid methyl ester hydrogen chloride as a colorless oil, MS (ES+): 546 (M+H).

Example 129

4-{2-cyclohexyl-2-[2-(4-methoxycarbonyl-phenyl)-benzoimidazol-1-yl]-acetylamino}-piperidine-1-carboxylic acid ethyl ester hydrogen chloride In analogy to examples 3.1-3.2, terephthalic acid monomethylester, cyclohexanecarbaldehyde, 4-isocyano-piperidine-1-carboxylic acid ethyl ester, and N-tert-butoxycarbonyl phenylene diamine gave 4-{2-cyclohexyl-2-[2-(4-methoxycarbonyl-phenyl)-benzoimidazol-1-yl]- acetylamino}-piperidine-1-carboxylic acid ethyl ester hydrogen chloride as a white solid, MS (ES+): 547 (M+H).

Example 130

N-cyclohexyl-2-[2-(2,4-dimethoxy-phenyl)-benzoimidazol-1-yl]-2-phenyl-acetamide hydrogen chloride In analogy to examples 3.1-3.2, 2,4-dimethoxy-benzoic acid, benzaldehyde, cyclohexyl isocyanide, and N-tert-butoxycarbonyl phenylene diamine gave N-cyclohexyl-2-[2-(2,4-dimethoxy-phenyl)-benzoimidazol-1-yl]-2-phenyl-acetamide hydrogen chloride as white solid, MS (ES+): 470 (M+H).

Example 131

4-(1-{cyclohexyl-[3-(2-oxo-pyrrolidin-1-yl)-propyl-carbamoyl]-methyl}-1H-benzoimidazol-2-yl)-benzoic acid methyl ester hydrogen chloride In analogy to examples 3.1-3.2, terephthalic acid monomethylester, cyclohexanecarbaldehyde, 1-(3-isocyano-propyl)-pyrrolidin-2-one, and N-tert-butoxycarbonyl phenylene diamine gave 4-(1-{cyclohexyl-[3-(2-oxo-pyrrolidin-1-yl)-propylcarbamoyl]-methyl}-1H-benzoimidazol-2-yl)-benzoic acid methyl ester hydrogen chloride as a colorless oil, MS (ES+): 517 (M+H).

Example 132

4-{1-[cyclohexyl-(3-methoxycarbonyl-propylcarbamoyl)-methyl]-1H-benzoimidazol-2-yl}-benzoic acid methyl ester hydrogen chloride In analogy to examples 3.1-3.2, terephthalic acid monomethylester, cyclohexanecarbaldehyde, 4-isocyano-butanoic acid methyl ester, and N-tert-butoxycarbonyl phenylene diamine gave 4-{1-[cyclohexyl-(4-methoxycarbonyl-propylcarbamoyl)-methyl]-1H-benzoimidazol-2-yl}-benzoic acid methyl ester hydrogen chloride as a colorless oil, MS (ES+): 492 (M+H).

Example 133

4-{1-[cyclohexyl-(4-methoxycarbonyl-butylcarbamoyl)-methyl]-1H-benzoimidazol-2-yl}-benzoic acid methyl ester hydrogen chloride In analogy to examples 3.1-3.2, terephthalic acid monomethylester, cyclohexanecarbaldehyde, 5-isocyano-pentanoic acid methyl ester, and N-tert-butoxycarbonyl phenylene diamine gave 4-{1-[cyclohexyl-(4-methoxycarbonyl-butylcarbamoyl)-methyl]-1H-benzoimidazol-2-yl}-benzoic acid methyl ester hydrogen chloride as a colorless oil, LC @215 nm; Rt 2.13: 100%, MS (ES+): 506 (M+H).

Example 134

4-{1-[cyclohexyl-(5-methoxycarbonyl-pentylcarbamoyl)-methyl]-1H-benzoimidazol-2-yl}-benzoic acid methyl ester hydrogen chloride In analogy to examples 3.1-3.2, terephthalic acid monomethylester, cyclohexanecarbaldehyde, 6-isocyano-hexanoic acid methyl ester, and N-tert-butoxycarbonyl phenylene diamine gave 4-{1-[cyclohexyl-(5-methoxycarbonyl-pentyl-carbamoyl)-methyl]-1H-benzoimidazol-2-yl}-benzoic acid methyl ester hydrogen chloride as a colorless oil, MS (ES+): 520 (M+H).

Example 135

2-cyclohexyl-2-[2-(2,4-dimethoxy-phenyl)-benzoimidazol-1-yl]-N-methyl-acetamide hydrogen chloride In analogy to examples 3.1-3.2, 2,4-dimethoxy benzoic acid, cyclohexanecarbaldehyde, methylisocyanide, and N-tert-butoxycarbonyl phenylene diamine gave 2-cyclohexyl-2-[2-(2,4-dimethoxy-phenyl)-benzoimidazol-1-yl]-N-methyl-acetamide hydrogen chloride as a white solid, MS (ES+): 408 (M+H).

Example 136

2-[2-(4-Acetylamino-phenyl)-benzoimidazol-1-yl]-2,N-dicyclohexyl-acetamide 136.1

In analogy to examples 31.-3.2, 4-tert-butoxycarbonylamino-benzoic acid, cyclohexanecarbaldehyde, cyclohexyl isocyanide, N-tert-butoxycarbonyl phenylene diamine gave, in a process accompanied by de-tert-butoxycarbonylation of the 4-tert-butoxycarbonylaminophenyl moiety, 2-[2-(4-amino-phenyl)-benzoimidazol-1-yl]-2,N-dicyclohexyl-acetamide hydrogen chloride as a white solid, MS (ES+): 431 (M+H).

136.2

Acetic anhydride (175 mg, 1.71 mmol, 1.0 equiv.) was added to a solution of 2-[2-(4-amino-phenyl)-benzoimidazol-1-yl]-2,N-dicyclohexyl-acetamide hydrogen chloride (example 34) (74 mg, 1.71 mmol, 1.0 equiv.) and pyridine (13 mg, 1.71 mmol, 1.0 equiv.) in dichloromethane (2 mL). The reaction was stirred at room temperature for 16 hours then retreated with pyridine (13 mg, 1.71 mmol, 1.0 equiv.) and acetic anhydride (17 mg, 0.17 mmol, 0.1 equiv.) and stirred at room temperature for a further 24 hours. The reaction mixture was added to 1 N HCl (2 mL) and the resultant precipitate was filtered and washed with dichloromethane. The solid was dissolved in hot ethyl acetate (3 mL) and filtered, the filtrate was concentrated in vacuo to afford 2-[2-(4-acetylamino-phenyl)-benzoimidazol-1-yl]-2,N-dicyclohexyl-acetamide as a cream solid, 26 mg (32%), MS (ES+): 473 (M+H).

Example 137

2-[2-(3-acetylamino-phenyl)-benzoimidazol-1-yl]-2,N-dicyclohexyl-acetamide 137.1

In analogy to examples 31.-3.2, 3-tert-butoxycarbonylamino-benzoic acid, cyclohexanecarbaldehyde, cyclohexyl isocyanide, N-tert-butoxycarbonyl phenylene diamine gave, in a process accompanied by de-tert-butoxycarbonylation of the 3-tert-butoxycarbonylaminophenyl moiety, 2-[2-(3-amino-phenyl)-benzoimidazol-1-yl]-2,N-dicyclohexyl-acetamide hydrogen chloride as a white solid, MS (ES+): 431 (M+H).

137.2

In analogy to example 136.2, 2-[2-(3-amino-phenyl)-benzoimidazol-1-yl]-2,N-dicyclohexyl-acetamide hydrogen chloride gave 2-[2-(3-acetylamino-phenyl)-benzoimidazol-1-yl]-2,N-dicyclohexyl-acetamide as a colorless oil, MS (ES+): 473 (M+H).

Example 138

4-{1-[cyclohexyl-(3-formylamino-phenylcarbamoyl)-methyl]-1H-benzoimidazol-2-yl}-benzoic acid methyl ester hydrogen chloride 138.1

In analogy to examples 3.1-3.2, terephthalic acid monomethylester, cyclohexanecarbaldehyde, N-(3-isocyano-phenyl)-formamide, and N-tert-butoxycarbonyl phenylene diamine gave 4-{1-[(3-amino-phenylcarbamoyl)-cyclohexyl-methyl]-1H-benzoimidazol-2-yl}-benzoic acid methyl ester hydrogen chloride, MS (ES+): 483 (M+H).

138.2

A mixture of acetic anhydride (162 mg, 1.58 mmol, 2.2 equiv.) and formic acid (73 mg, 1.58 mmol, 2.2 equiv.) was heated to 60° C. for 15 minutes. The reaction was cooled to room temperature and a solution of 4-{1-[(3-amino-phenylcarbamoyl)-cyclohexyl-methyl]-1H-benzoimidazol-2-yl}-benzoic acid methyl ester (35 mg, 0.72 mmol, 1.0 equiv.) in dichloromethane (2 mL) was added and the reaction mixture stirred at room temperature for 16 hours. The reaction mixture was washed with 1 N HCl (2 mL) and the organic layer dried over magnesium sulphate. The reaction mixture was concentrated in vacuo to afford 4-{1-[cyclohexyl-(3-formylamino-phenylcarbamoyl)-methyl]-1H-benzoimidazol-2-yl}-benzoic acid methyl ester, 23 mg (62% yield) as a yellow solid, MS (ES+): 511 (M+H).

Example 139

N-cyclopentyl-2-(2-naphthalen-1-yl-benzoimidazol-1-yl)-propionamide

In analogy to examples 2.1-2.2, naphthalene-1-carboxylic acid, acetaldehyde, cyclopentylisocyanide, and N-tert-butoxycarbonyl phenylene diamine gave N-cyclopentyl-2-(2-naphthalen-1-yl-benzoimidazol-1-yl)-propionamide as a white solid, MS (ES+): 438 (M+H).

Example 140

2,N-Dicyclohexyl-2-(2-phenyl-benzoimidazol-1-yl)-acetamide

Benzoic acid (12.2 mg, 0.1 mmol, 1 equiv.) was added to a solution of cyclohexanecarbaldehyde (16.8 mg, 0.15 mmol, 1.5 equiv.), cyclohexyl isocyanide (10.9 mg, 0.1 mmol, 1 equiv.) and N-tert-butoxycarbonyl phenylene diamine (20.8 mg, 0.1 mmol, 1 equiv.) in methanol (1 mL) and the mixture was stirred at room temperature for 16 hours. The solvent was evaporated and the crude intermediate dissolved in TFA (1 ml) and stirred at room temperature for 16 hours. The TFA was evaporated and the product isolated via preparative HPLC (gradient elution: water/acetonitrile with 0.1% trifluoroacetic acid). MS (ES+): 416 (M+H).

Example 141

2-[1-(Cyclohexyl-cyclohexylcarbamoyl-methyl)-1H-benzoimidazol-2-yl]-benzamide

N-tert-butoxycarbonyl phenylene diamine (208.3 mg, 1 mmol, 1 equiv.) was added to a solution of cyclohexanecarbaldehyde (168.3 mg, 1.5 mmol, 1.5 equiv.), cyclohexyl isocyanide (109.2 mg, 1 mmol, 1 equiv.) and phthalic acid monomethyl ester (180.2 mg, 1 mmol, 1 equiv.) in methanol (20 mL). The mixture was stirred at room temperature for 16 hours. After evaporation of the solvent the crude intermediate was dissolved in TFA (10 ml) and stirred at room temperature for 16 hours. After evaporation the crude was dissolved in acetic acid and stirred at 80° C. for 16 h. After evaporation the crude was dissolved in ethyl acetate and extracted from aq. NaHCO$_3$. The residue obtained after the evaporation of the organic layer was dissolved in Methanol (10 ml) and treated with 2N NaOH (5 ml) at room temperature for 16 h. The resulting carboxylic acid was isolated via preperative HPLC. 46 mg (0.1 mmol, 1 equiv.) were dissolved in DMF (1 ml). 38 mg (0.1 mmol, 1 equiv.) of HATU were added and the mixture stirred at room temperature for 10 min. 200 ul of a saturated NH3/MeOH solution were added. The reaction was stirred at room temperature for 16 h. The product was isolated via prep. HPLC. MS (ES+): 460 (M+H).

Example 142

2-[2-(5-Amino-pyridin-2-yl)-benzoimidazol-1-yl]-2,N-dicyclohexyl-acetamide

In analogy to example 140, 5-Amino-pyridine-2-carboxylic acid, cyclohexanecarbaldehyde, cyclohexyl isocyanide and N-tert-butoxycarbonyl phenylene diamine. MS (ES+): 432 (M+H).

Example 143

2,N-Dicyclohexyl-2-[2-(2-ethyl-5-methyl-2H-pyrazol-3-yl)-benzoimidazol-1-yl]-acetamide In analogy to example 140, 1-Ethyl-3-methyl-1H-pyrazole-5-carboxylic acid, cyclohexanecarbaldehyde, cyclohexyl isocyanide and N-tert-butoxycarbonyl phenylene diamine. MS (ES+): 449 (M+H).

Example 144

2,N-Dicyclohexyl-2-[2-(5-methyl-isoxazol-4-yl)-benzoimidazol-1-yl]-acetamide

In analogy to example 140, 5-Methylisoxazole-4-carboxylic acid, cyclohexanecarbaldehyde, cyclohexyl isocyanide and N-tert-butoxycarbonyl phenylene diamine. MS (ES+): 421 (M+H).

Example 145

2,N-Dicyclohexyl-2-[2-(1H-pyrrol-2-yl)-benzoimidazol-1-yl]-acetamide

In analogy to example 140, Pyrrazole-2-carboxylic acid, cyclohexanecarbaldehyde, cyclohexyl isocyanide and N-tert-butoxycarbonyl phenylene diamine. MS (ES+): 405 (M+H).

Example 146

2-(1'H-[2,5']Bibenzoimidazolyl-1-yl)-2,N-dicyclohexyl-acetamide

In analogy to example 140, 5-Benzimidazolecarboxylic acid, cyclohexanecarbaldehyde, cyclohexyl isocyanide and N-tert-butoxycarbonyl phenylene diamine. MS (ES+): 456 (M+H).

Example 147

2,N-Dicyclohexyl-2-(2-furan-2-yl-benzoimidazol-1-yl)-acetamide

In analogy to example 140, 2-Furoic acid, cyclohexanecarbaldehyde, cyclohexyl isocyanide and N-tert-butoxycarbonyl phenylene diamine. MS (ES+): 406 (M+H).

Example 148

2-[6-Bromo-2-(4-chloro-phenyl)-benzoimidazol-1-yl]-2,N-dicyclohexyl-acetamide

In analogy to example 140, 4-Chlorobenzoic acid, cyclohexanecarbaldehyde, cyclohexyl isocyanide and (2-Amino-4-bromo-phenyl)-carbamic acid tert-butyl ester. MS (ES+): 530 (M+H).

Example 149

2-[6-Chloro-2-(4-chloro-phenyl)-benzoimidazol-1-yl]-2,N-dicyclohexyl-acetamide

In analogy to example 140, 4-Chlorobenzoic acid, cyclohexanecarbaldehyde, cyclohexyl isocyanide and (2-Amino-4-chloro-phenyl)-carbamic acid tert-butyl ester. MS (ES+): 485 (M+H).

Example 150

2-[2-(4-Chloro-phenyl)-6-methoxy-benzoimidazol-1-yl]-2,N-dicyclohexyl-acetamide

In analogy to example 140, 4-Chlorobenzoic acid, cyclohexanecarbaldehyde, cyclohexyl isocyanide and (2-Amino-4-methoxy-phenyl)-carbamic acid tert-butyl ester. MS (ES+): 481 (M+H).

Example 151

2-[6-Chloro-2-(4-chloro-phenyl)-5-fluoro-benzoimidazol-1-yl]-2,N-dicyclohexyl-acetamide In analogy to example 140, 4-Chlorobenzoic acid, cyclohexanecarbaldehyde, cyclohexyl isocyanide and (2-Amino-4-chloro-5-fluoro-phenyl)-carbamic acid tert-butyl ester. MS (ES+): 503 (M+H).

Example 152

(S)-2,N-Dicyclohexyl-2-[2-(2,4-dimethoxy-phenyl)-benzoimidazol-1-yl]-acetamide

In analogy to example 140, 2,4-Dimethoxybenzoic acid, cyclohexanecarbaldehyde, cyclohexyl isocyanide and N-tert-butoxycarbonyl phenylene diamine. MS (ES+): 476 (M+H).

Example 153

(S)-2-[2-(4-Chloro-phenyl)-benzoimidazol-1-yl]-2,N-dicyclohexyl-acetamide

In analogy to example 140, 4-Chlorobenzoic acid, cyclohexanecarbaldehyde, cyclohexyl isocyanide and N-tert-butoxycarbonyl phenylene diamine. MS (ES+): 451 (M+H).

Example 154

2-[1-(Cyclohexyl-cyclohexylcarbamoyl-methyl)-1H-benzoimidazol-2-yl]-N-methyl-benzamide In analogy to example 141, phthalic acid monomethyl ester, cyclohexanecarbaldehyde, cyclohexyl isocyanide, N-tert-butoxycarbonyl phenylene diamine and methylamine. MS (ES+): 473 (M+H).

Example 155

2,N-Dicyclohexyl-2-(2-furan-3-yl-benzoimidazol-1-yl)-acetamide

In analogy to example 140, 3-Furoic acid, cyclohexanecarbaldehyde, cyclohexyl isocyanide and N-tert-butoxycarbonyl phenylene diamine. MS (ES+): 406 (M+H).

Example 156

2,N-Dicyclohexyl-2-[2-(3-methyl-furan-2-yl)-benzoimidazol-1-yl]-acetamide

In analogy to example 140, 3-Methyl-2-furoic acid, cyclohexanecarbaldehyde, cyclohexyl isocyanide and N-tert-butoxycarbonyl phenylene diamine. MS (ES+): 420 (M+H).

Example 157

2,N-Dicyclohexyl-2-[2-(3-methyl-isoxazol-5-yl)-benzoimidazol-1-yl]-acetamide

In analogy to example 140, 3-Methyl-isoxazole-5-carboxylic acid, cyclohexanecarbaldehyde, cyclohexyl isocyanide and N-tert-butoxycarbonyl phenylene diamine. MS (ES+): 421 (M+H).

Example 158

2,N-Dicyclohexyl-2-(2-m-tolyl-benzoimidazol-1-yl)-acetamide

In analogy to example 140, m-Toluic acid, cyclohexanecarbaldehyde, cyclohexyl isocyanide and N-tert-butoxycarbonyl phenylene diamine. MS (ES+): 430 (M+H).

Example 159

2,N-Dicyclohexyl-2-[2-(3-fluoro-phenyl)-benzoimidazol-1-yl]-acetamide

In analogy to example 140, 3-Fluorobenzoic acid, cyclohexanecarbaldehyde, cyclohexyl isocyanide and N-tert-butoxycarbonyl phenylene diamine. MS (ES+): 434 (M+H).

Example 160

2,N-Dicyclohexyl-2-[2-(2-fluoro-phenyl)-benzoimidazol-1-yl]-acetamide

In analogy to example 140, 2-Fluorobenzoic acid, cyclohexanecarbaldehyde, cyclohexyl isocyanide and N-tert-butoxycarbonyl phenylene diamine. MS (ES+): 434 (M+H).

Example 161

2,N-Dicyclohexyl-2-[2-(3,5-dimethyl-isoxazol-4-yl)-benzoimidazol-1-yl]-acetamide In analogy to example 140, 3,5-Dimethylisoxazole-4-carboxylic acid, cyclohexanecarbaldehyde, cyclohexyl isocyanide and N-tert-butoxycarbonyl phenylene diamine. MS (ES+): 435 (M+H).

Example 162

2,N-Dicyclohexyl-2-[2-(3-methyl-thiophen-2-yl)-benzoimidazol-1-yl]-acetamide

In analogy to example 140, 3-Methyl-2-thiophenecarboxylic acid, cyclohexanecarbaldehyde, cyclohexyl isocyanide and N-tert-butoxycarbonyl phenylene diamine. MS (ES+): 436 (M+H).

Example 163

2,N-Dicyclohexyl-2-[2-(4-vinyl-phenyl)-benzoimidazol-1-yl]-acetamide

In analogy to example 140, 4-Vinylbenzoic acid, cyclohexanecarbaldehyde, cyclohexyl isocyanide and N-tert-butoxycarbonyl phenylene diamine. MS (ES+): 442 (M+H).

Example 164

2,N-Dicyclohexyl-2-[2-(2,3-dimethyl-phenyl)-benzoimidazol-1-yl]-acetamide

In analogy to example 140, 2,3-Dimethylbenzoic acid, cyclohexanecarbaldehyde, cyclohexyl isocyanide and N-tert-butoxycarbonyl phenylene diamine. MS (ES+): 444 (M+H).

Example 165

2,N-Dicyclohexyl-2-[2-(3,4-dimethyl-phenyl)-benzoimidazol-1-yl]-acetamide

In analogy to example 140, 3,4-Dimethylbenzoic acid, cyclohexanecarbaldehyde, cyclohexyl isocyanide and N-tert-butoxycarbonyl phenylene diamine. MS (ES+): 444 (M+H).

Example 166

2,N-Dicyclohexyl-2-[2-(4-ethyl-phenyl)-benzoimidazol-1-yl]-acetamide

In analogy to example 140, 4-Ethylbenzoic acid, cyclohexanecarbaldehyde, cyclohexyl isocyanide and N-tert-butoxycarbonyl phenylene diamine. MS (ES+): 444 (M+H).

Example 167

2,N-Dicyclohexyl-2-[2-(2,4-dimethyl-phenyl)-benzoimidazol-1-yl]-acetamide

In analogy to example 140, 2,4-Dimethylbenzoic acid, cyclohexanecarbaldehyde, cyclohexyl isocyanide and N-tert-butoxycarbonyl phenylene diamine. MS (ES+): 444 (M+H).

Example 168

2,N-Dicyclohexyl-2-[2-(2-ethyl-phenyl)-benzoimidazol-1-yl]-acetamide

In analogy to example 140, 2-Ethylbenzoic acid, cyclohexanecarbaldehyde, cyclohexyl isocyanide and N-tert-butoxycarbonyl phenylene diamine. MS (ES+): 444 (M+H).

Example 169

2,N-Dicyclohexyl-2-[2-(4-fluoro-3-methyl-phenyl)-benzoimidazol-1-yl]-acetamide

In analogy to example 140, 4-Fluoro-3-methylbenzoic acid, cyclohexanecarbaldehyde, cyclohexyl isocyanide and N-tert-butoxycarbonyl phenylene diamine. MS (ES+): 448 (M+H).

Example 170

2,N-Dicyclohexyl-2-[2-(3-fluoro-4-methyl-phenyl)-benzoimidazol-1-yl]-acetamide

In analogy to example 140, 3-Fluoro-4-methylbenzoic acid, cyclohexanecarbaldehyde, cyclohexyl isocyanide and N-tert-butoxycarbonyl phenylene diamine. MS (ES+): 448 (M+H).

Example 171

2,N-Dicyclohexyl-2-[2-(2,6-difluoro-phenyl)-benzoimidazol-1-yl]-acetamide

In analogy to example 140, 2,6-Difluorobenzoic acid, cyclohexanecarbaldehyde, cyclohexyl isocyanide and N-tert-butoxycarbonyl phenylene diamine. MS (ES+): 452 (M+H).

Example 172

2,N-Dicyclohexyl-2-[2-(3,5-difluoro-phenyl)-benzoimidazol-1-yl]-acetamide

In analogy to example 140, 3,5-Difluorobenzoic acid, cyclohexanecarbaldehyde, cyclohexyl isocyanide and N-tert-butoxycarbonyl phenylene diamine. MS (ES+): 452 (M+H).

Example 173

2,N-Dicyclohexyl-2-[2-(2,5-difluoro-phenyl)-benzoimidazol-1-yl]-acetamide

In analogy to example 140, 2,5-Difluorobenzoic acid, cyclohexanecarbaldehyde, cyclohexyl isocyanide and N-tert-butoxycarbonyl phenylene diamine. MS (ES+): 452 (M+H).

Example 174

2,N-Dicyclohexyl-2-[2-(3,4-difluoro-phenyl)-benzoimidazol-1-yl]-acetamide

In analogy to example 140, 3,4-Difluorobenzoic acid, cyclohexanecarbaldehyde, cyclohexyl isocyanide and N-tert-butoxycarbonyl phenylene diamine. MS (ES+): 452 (M+H).

Example 175

2,N-Dicyclohexyl-2-[2-(2,3-difluoro-phenyl)-benzoimidazol-1-yl]-acetamide

In analogy to example 140, 2,3-Difluorobenzoic acid, cyclohexanecarbaldehyde, cyclohexyl isocyanide and N-tert-butoxycarbonyl phenylene diamine. MS (ES+): 452 (M+H).

Example 176

2,N-Dicyclohexyl-2-[2-(1H-indol-4-yl)-benzoimidazol-1-yl]-acetamide

In analogy to example 140, Indole-4-carboxylic acid, cyclohexanecarbaldehyde, cyclohexyl isocyanide and N-tert-butoxycarbonyl phenylene diamine. MS (ES+): 455 (M+H).

Example 177

2,N-Dicyclohexyl-2-[2-(1H-indol-6-yl)-benzoimidazol-1-yl]-acetamide

In analogy to example 140, Indole-6-carboxylic acid, cyclohexanecarbaldehyde, cyclohexyl isocyanide and N-tert-butoxycarbonyl phenylene diamine. MS (ES+): 455 (M+H).

Example 178

2-[2-(5-Chloro-thiophen-2-yl)-benzoimidazol-1-yl]-2,N-dicyclohexyl-acetamide

In analogy to example 140, 5-Chlorothiophene-2-carboxylic acid, cyclohexanecarbaldehyde, cyclohexyl isocyanide and N-tert-butoxycarbonyl phenylene diamine. MS (ES+): 457 (M+H).

Example 179

2-[2-(4-Acetyl-phenyl)-benzoimidazol-1-yl]-2,N-dicyclohexyl-acetamide

In analogy to example 140, 4-Acetylbenzoic acid, cyclohexanecarbaldehyde, cyclohexyl isocyanide and N-tert-butoxycarbonyl phenylene diamine. MS (ES+): 458 (M+H).

Example 180

2-[2-(2-Acetyl-phenyl)-benzoimidazol-1-yl]-2,N-dicyclohexyl-acetamide

In analogy to example 140, 2-Acetylbenzoic acid, cyclohexanecarbaldehyde, cyclohexyl isocyanide and N-tert-butoxycarbonyl phenylene diamine. MS (ES+): 458 (M+H).

Example 181

2,N-Dicyclohexyl-2-[2-(4-isopropyl-phenyl)-benzoimidazol-1-yl]-acetamide

In analogy to example 140, 4-Isopropylbenzoic acid, cyclohexanecarbaldehyde, cyclohexyl isocyanide and N-tert-butoxycarbonyl phenylene diamine. MS (ES+): 458 (M+H).

Example 182

2-[2-(4-Cyano-2-fluoro-phenyl)-benzoimidazol-1-yl]-2,N-dicyclohexyl-acetamide

In analogy to example 140, 4-Cyano-2-fluorobenzoic acid, cyclohexanecarbaldehyde, cyclohexyl isocyanide and N-tert-butoxycarbonyl phenylene diamine. MS (ES+): 459 (M+H).

Example 183

2,N-Dicyclohexyl-2-[2-(2-dimethylamino-phenyl)-benzoimidazol-1-yl]-acetamide

In analogy to example 140, 2-Dimethylaminobenzoic acid, cyclohexanecarbaldehyde, cyclohexyl isocyanide and N-tert-butoxycarbonyl phenylene diamine. MS (ES+): 459 (M+H).

Example 184

2,N-Dicyclohexyl-2-[2-(3-dimethylamino-phenyl)-benzoimidazol-1-yl]-acetamide

In analogy to example 140, 3-Dimethylaminobenzoic acid, cyclohexanecarbaldehyde, cyclohexyl isocyanide and N-tert-butoxycarbonyl phenylene diamine. MS (ES+): 459 (M+H).

Example 185

2,N-Dicyclohexyl-2-[2-(4-methoxy-3-methyl-phenyl)-benzoimidazol-1-yl]-acetamide

In analogy to example 140, 4-Methoxy-3-methylbenzoic acid, cyclohexanecarbaldehyde, cyclohexyl isocyanide and N-tert-butoxycarbonyl phenylene diamine. MS (ES+): 460 (M+H).

Example 186

2,N-Dicyclohexyl-2-[2-(4-methoxy-2-methyl-phenyl)-benzoimidazol-1-yl]-acetamide

In analogy to example 140, 4-Methoxy-2-methylbenzoic acid, cyclohexanecarbaldehyde, cyclohexyl isocyanide and N-tert-butoxycarbonyl phenylene diamine. MS (ES+): 460 (M+H).

Example 187

2,N-Dicyclohexyl-2-[2-(3-methoxy-4-methyl-phenyl)-benzoimidazol-1-yl]-acetamide

In analogy to example 140, 3-Methoxy-4-methylbenzoic acid, cyclohexanecarbaldehyde, cyclohexyl isocyanide and N-tert-butoxycarbonyl phenylene diamine. MS (ES+): 460 (M+H).

Example 188

2,N-Dicyclohexyl-2-[2-(2-ethoxy-phenyl)-benzoimidazol-1-yl]-acetamide

In analogy to example 140, 2-Ethoxybenzoic acid, cyclohexanecarbaldehyde, cyclohexyl isocyanide and N-tert-butoxycarbonyl phenylene diamine. MS (ES+): 460 (M+H).

Example 189

2-[2-(6-Chloro-pyridin-3-yl)-benzoimidazol-1-yl]-2,N-dicyclohexyl-acetamide

In analogy to example 140, 6-Chloronicotinic acid, cyclohexanecarbaldehyde, cyclohexyl isocyanide and N-tert-butoxycarbonyl phenylene diamine. MS (ES+): 452 (M+H).

Example 190

2-[2-(2-Chloro-pyridin-4-yl)-benzoimidazol-1-yl]-2,N-dicyclohexyl-acetamide

In analogy to example 140, 2-Chloroisonicotinic acid, cyclohexanecarbaldehyde, cyclohexyl isocyanide and N-tert-butoxycarbonyl phenylene diamine. MS (ES+): 452 (M+H).

Example 191

2-[2-(4-Chloro-phenyl)-6-fluoro-benzoimidazol-1-yl]-2,N-dicyclohexyl-acetamide

In analogy to example 140, 4-Chlorobenzoic acid, cyclohexanecarbaldehyde, cyclohexyl isocyanide and (2-amino-4-fluoro-phenyl)-carbamic acid tert-butyl ester. MS (ES+): 468 (M+H).

Example 192

2,N-Dicyclohexyl-2-[2-(3-fluoro-4-methoxy-phenyl)-benzoimidazol-1-yl]-acetamide

In analogy to example 140, 3-Fluoro-4-methoxybenzoic acid, cyclohexanecarbaldehyde, cyclohexyl isocyanide and N-tert-butoxycarbonyl phenylene diamine. MS (ES+): 420 (M+H).

Example 193

2-[2-(4-Chloro-3-methyl-phenyl)-benzoimidazol-1-yl]-2,N-dicyclohexyl-acetamide

In analogy to example 140, 4-Chloro-3-methylbenzoic acid, cyclohexanecarbaldehyde, cyclohexyl isocyanide and N-tert-butoxycarbonyl phenylene diamine. MS (ES+): 464 (M+H).

Example 194

2-[2-(3-Chloro-2-methyl-phenyl)-benzoimidazol-1-yl]-2,N-dicyclohexyl-acetamide

In analogy to example 140, 3-Chloro-2-methylbenzoic acid, cyclohexanecarbaldehyde, cyclohexyl isocyanide and N-tert-butoxycarbonyl phenylene diamine. MS (ES+): 464 (M+H).

Example 195

2-[2-(4-Chloro-3-fluoro-phenyl)-benzoimidazol-1-yl]-2,N-dicyclohexyl-acetamide

In analogy to example 140, 4-Chloro-3-fluorobenzoic acid, cyclohexanecarbaldehyde, cyclohexyl isocyanide and N-tert-butoxycarbonyl phenylene diamine. MS (ES+): 468 (M+H).

Example 196

2-[2-(3-Chloro-4-fluoro-phenyl)-benzoimidazol-1-yl]-2,N-dicyclohexyl-acetamide

In analogy to example 140, 3-Chloro-4-fluorobenzoic acid, cyclohexanecarbaldehyde, cyclohexyl isocyanide and N-tert-butoxycarbonyl phenylene diamine. MS (ES+): 468 (M+H).

Example 197

2,N-Dicyclohexyl-2-[2-(5-methyl-1H-indol-2-yl)-benzoimidazol-1-yl]-acetamide

In analogy to example 140, 5-Methylindole-2-carboxylic acid, cyclohexanecarbaldehyde, cyclohexyl isocyanide and N-tert-butoxycarbonyl phenylene diamine. MS (ES+): 469 (M+H).

Example 198

2,N-Dicyclohexyl-2-[2-(2,3,4-trifluoro-phenyl)-benzoimidazol-1-yl]-acetamide

In analogy to example 140, 2,3,4-Trifluorobenzoic acid, cyclohexanecarbaldehyde, cyclohexyl isocyanide and N-tert-butoxycarbonyl phenylene diamine. MS (ES+): 470 (M+H).

Example 199

2,N-Dicyclohexyl-2-[2-(2,4,5-trifluoro-phenyl)-benzoimidazol-1-yl]-acetamide

In analogy to example 140, 2,4,5-Trifluorobenzoic acid, cyclohexanecarbaldehyde, cyclohexyl isocyanide and N-tert-butoxycarbonyl phenylene diamine. MS (ES+): 470 (M+H).

Example 200

2-(2-Benzo[b]thiophen-2-yl-benzoimidazol-1-yl)-2,N-dicyclohexyl-acetamide

In analogy to example 140, Benzthiophene-2-carboxylic acid, cyclohexanecarbaldehyde, cyclohexyl isocyanide and N-tert-butoxycarbonyl phenylene diamine. MS (ES+): 472 (M+H).

Example 201

2,N-Dicyclohexyl-2-[2-(5-fluoro-1H-indol-2-yl)-benzoimidazol-1-yl]-acetamide

In analogy to example 140, 5-Fluoroindole-2-carboxylic acid, cyclohexanecarbaldehyde, cyclohexyl isocyanide and N-tert-butoxycarbonyl phenylene diamine. MS (ES+): 473 (M+H).

Example 202

2-(2-Benzothiazol-6-yl-benzoimidazol-1-yl)-2,N-dicyclohexyl-acetamide

In analogy to example 140, Benzothiazole-2-carboxylic acid, cyclohexanecarbaldehyde, cyclohexyl isocyanide and N-tert-butoxycarbonyl phenylene diamine. MS (ES+): 473 (M+H).

Example 203

2,N-Dicyclohexyl-2-[2-(4-isopropoxy-phenyl)-benzoimidazol-1-yl]-acetamide

In analogy to example 140, 4-Isopropoxybenzoic acid, cyclohexanecarbaldehyde, cyclohexyl isocyanide and N-tert-butoxycarbonyl phenylene diamine. MS (ES+): 475 (M+H).

Example 204

2,N-Dicyclohexyl-2-[2-(3,4-dimethoxy-phenyl)-benzoimidazol-1-yl]-acetamide

In analogy to example 140, 3,4-Dimethoxybenzoic acid, cyclohexanecarbaldehyde, cyclohexyl isocyanide and N-tert-butoxycarbonyl phenylene diamine. MS (ES+): 476 (M+H).

Example 205

2,N-Dicyclohexyl-2-[2-(2,5-dimethoxy-phenyl)-benzoimidazol-1-yl]-acetamide

In analogy to example 140, 2,5-Dimethoxybenzoic acid, cyclohexanecarbaldehyde, cyclohexyl isocyanide and N-tert-butoxycarbonyl phenylene diamine. MS (ES+): 476 (M+H).

Example 206

2,N-Dicyclohexyl-2-[2-(2-difluoromethoxy-phenyl)-benzoimidazol-1-yl]-acetamide

In analogy to example 140, 2-(Difluoromethoxy)benzoic acid, cyclohexanecarbaldehyde, cyclohexyl isocyanide and N-tert-butoxycarbonyl phenylene diamine. MS (ES+): 482 (M+H).

Example 207

2,N-Dicyclohexyl-2-[2-(4-difluoromethoxy-phenyl)-benzoimidazol-1-yl]-acetamide

In analogy to example 140, 4-(Difluoromethoxy)benzoic acid, cyclohexanecarbaldehyde, cyclohexyl isocyanide and N-tert-butoxycarbonyl phenylene diamine. MS (ES+): 482 (M+H).

Example 208

2,N-Dicyclohexyl-2-[2-(3-difluoromethoxy-phenyl)-benzoimidazol-1-yl]-acetamide

In analogy to example 140, 3-(Difluoromethoxy)benzoic acid, cyclohexanecarbaldehyde, cyclohexyl isocyanide and N-tert-butoxycarbonyl phenylene diamine. MS (ES+): 482 (M+H).

Example 209

2,N-Dicyclohexyl-2-[2-(4-trifluoromethyl-phenyl)-benzoimidazol-1-yl]-acetamide

In analogy to example 140, 4-Trifluoromethylbenzoic acid, cyclohexanecarbaldehyde, cyclohexyl isocyanide and N-tert-butoxycarbonyl phenylene diamine. MS (ES+): 484 (M+H).

Example 210

2,N-Dicyclohexyl-2-[2-(3,4-dichloro-phenyl)-benzoimidazol-1-yl]-acetamide

In analogy to example 140, 3,4-Dichlorobenzoic acid, cyclohexanecarbaldehyde, cyclohexyl isocyanide and N-tert-butoxycarbonyl phenylene diamine. MS (ES+): 485 (M+H).

Example 211

2-[2-(4-Bromo-phenyl)-benzoimidazol-1-yl]-2,N-dicyclohexyl-acetamide

In analogy to example 140, 4-Bromobenzoic acid, cyclohexanecarbaldehyde, cyclohexyl isocyanide and N-tert-butoxycarbonyl phenylene diamine. MS (ES+): 495 (M+H).

Example 212

2,N-Dicyclohexyl-2-[2-(6-methoxy-naphthalen-2-yl)-benzoimidazol-1-yl]-acetamide

In analogy to example 140, 6-Methoxy-2-naphthoic acid, cyclohexanecarbaldehyde, cyclohexyl isocyanide and N-tert-butoxycarbonyl phenylene diamine. MS (ES+): 497 (M+H).

Example 213

2,N-Dicyclohexyl-2-[2-(3-trifluoromethoxy-phenyl)-benzoimidazol-1-yl]-acetamide

In analogy to example 140, 3-(Trifluoromethoxy)benzoic acid, cyclohexanecarbaldehyde, cyclohexyl isocyanide and N-tert-butoxycarbonyl phenylene diamine. MS (ES+): 500 (M+H).

Example 214

2,N-Dicyclohexyl-2-[2-(7-ethoxy-benzofuran-2-yl)-benzoimidazol-1-yl]-acetamide

In analogy to example 140, 7-Ethoxybenzofuran-2-carboxylic acid, cyclohexanecarbaldehyde, cyclohexyl isocyanide and N-tert-butoxycarbonyl phenylene diamine. MS (ES+): 500 (M+H).

Example 215

2,N-Dicyclohexyl-2-[2-(3-fluoro-4-trifluoromethyl-phenyl)-benzoimidazol-1-yl]-acetamide In analogy to example 140, 3-Fluoro-4-(trifluoromethyl)benzoic acid, cyclohexanecarbaldehyde, cyclohexyl isocyanide and N-tert-butoxycarbonyl phenylene diamine. MS (ES+): 502 (M+H).

Example 216

2,N-Dicyclohexyl-2-[2-(6-diethylamino-pyridin-3-yl)-benzoimidazol-1-yl]-acetamide 90 mg of 2-[2-(6-Chloro-pyridin-3-yl)-benzoimidazol-1-yl]-2,N-dicyclohexyl-acetamide (example 189) (0.2 mmol, 1 equiv.) were dissolved in DMF (1 ml). 102 ul (1 mmol, 5 equiv.) of diethylamine are added. The mixture was heated to 120° C. for 15 min using microwave heating). The product was isolated via preperative HPLC. MS (ES+): 489 (M+H).

Example 217

2-[2-(2-Chloro-5-methyl-phenyl)-benzoimidazol-1-yl]-2,N-dicyclohexyl-acetamide

In analogy to example 140, 2-Chloro-5-methylbenzoic acid, cyclohexanecarbaldehyde, cyclohexyl isocyanide and N-tert-butoxycarbonyl phenylene diamine. MS (ES+): 464 (M+H).

Example 218

2-[2-(5-Chloro-2-methyl-phenyl)-benzoimidazol-1-yl]-2,N-dicyclohexyl-acetamide

In analogy to example 140, 5-Chloro-2-methylbenzoic acid, cyclohexanecarbaldehyde, cyclohexyl isocyanide and N-tert-butoxycarbonyl phenylene diamine. MS (ES+): 464 (M+H).

Example 219

2-[2-(2-Chloro-6-methyl-phenyl)-benzoimidazol-1-yl]-2,N-dicyclohexyl-acetamide

In analogy to example 140, 2-Chloro-6-methylbenzoic acid, cyclohexanecarbaldehyde, cyclohexyl isocyanide and N-tert-butoxycarbonyl phenylene diamine. MS (ES+): 464 (M+H).

Example 220

2,N-Dicyclohexyl-2-(2-quinoxalin-6-yl-benzoimidazol-1-yl)-acetamide

In analogy to example 140, Quinoxaline-6-carboxylic acid, cyclohexanecarbaldehyde, cyclohexyl isocyanide and N-tert-butoxycarbonyl phenylene diamine. MS (ES+): 468 (M+H).

Example 221

2-[2-(5-Chloro-2-fluoro-phenyl)-benzoimidazol-1-yl]-2,N-dicyclohexyl-acetamide

In analogy to example 140, 5-Chloro-2-fluorobenzoic acid, cyclohexanecarbaldehyde, cyclohexyl isocyanide and N-tert-butoxycarbonyl phenylene diamine. MS (ES+): 468 (M+H).

Example 222

2,N-Dicyclohexyl-2-[2-(4-methoxy-3,5-dimethyl-phenyl)-benzoimidazol-1-yl]-acetamide In analogy to example 140, 3,5-Dimethyl-p-anisic acid, cyclohexanecarbaldehyde, cyclohexyl isocyanide and N-tert-butoxycarbonyl phenylene diamine. MS (ES+): 475 (M+H).

Example 223

2,N-Dicyclohexyl-2-[2-(2,3-dimethoxy-phenyl)-benzoimidazol-1-yl]-acetamide

In analogy to example 140, 2,3-Dimethoxybenzoic acid, cyclohexanecarbaldehyde, cyclohexyl isocyanide and N-tert-butoxycarbonyl phenylene diamine. MS (ES+): 476 (M+H).

Example 224

2-[2-(3-Chloro-4-methoxy-phenyl)-benzoimidazol-1-yl]-2,N-dicyclohexyl-acetamide

In analogy to example 140, 3-Chloro-4-methoxybenzoic acid, cyclohexanecarbaldehyde, cyclohexyl isocyanide and N-tert-butoxycarbonyl phenylene diamine. MS (ES+): 481 (M+H).

Example 225

2,N-Dicyclohexyl-2-[2-(2,5-dichloro-phenyl)-benzoimidazol-1-yl]-acetamide

In analogy to example 140, 2,5-Dichlorobenzoic acid, cyclohexanecarbaldehyde, cyclohexyl isocyanide and N-tert-butoxycarbonyl phenylene diamine. MS (ES+): 485 (M+H).

Example 226

2-[2-(3-Chloro-2,4-difluoro-phenyl)-benzoimidazol-1-yl]-2,N-dicyclohexyl-acetamide In analogy to example 140, 3-Chloro-2,4-difluorobenzoic acid, cyclohexanecarbaldehyde, cyclohexyl isocyanide and N-tert-butoxycarbonyl phenylene diamine. MS (ES+): 486 (M+H).

Example 227

2-[2-(2-Chloro-4,5-difluoro-phenyl)-benzoimidazol-1-yl]-2,N-dicyclohexyl-acetamide In analogy to example 140, 2-Chloro-4,5-difluorobenzoic acid, cyclohexanecarbaldehyde, cyclohexyl isocyanide and N-tert-butoxycarbonyl phenylene diamine. MS (ES+): 486 (M+H).

Example 228

2,N-Dicyclohexyl-2-[2-(4-diethylamino-phenyl)-benzoimidazol-1-yl]-acetamide

In analogy to example 140, 4-Diethylaminobenzoic acid, cyclohexanecarbaldehyde, cyclohexyl isocyanide and N-tert-butoxycarbonyl phenylene diamine. MS (ES+): 487 (M+H).

Example 229

2-[2-(4-Benzoyl-phenyl)-benzoimidazol-1-yl]-2,N-dicyclohexyl-acetamide

In analogy to example 140, 4-Benzoylbenzoic acid, cyclohexanecarbaldehyde, cyclohexyl isocyanide and N-tert-butoxycarbonyl phenylene diamine. MS (ES+): 520 (M+H).

Example 230

(S)-2-[2-(4-Cyano-phenyl)-benzoimidazol-1-yl]-2,N-dicyclohexyl-acetamide

In analogy to example 140, 4-Cyanobenzoic acid, cyclohexanecarbaldehyde, cyclohexyl isocyanide and N-tert-butoxycarbonyl phenylene diamine. MS (ES+): 441 (M+H).

Example 231

2,N-Dicyclohexyl-2-[2-(4-phenoxy-phenyl)-benzoimidazol-1-yl]-acetamide

In analogy to example 140, 4-Phenoxybenzoic acid, cyclohexanecarbaldehyde, cyclohexyl isocyanide and N-tert-butoxycarbonyl phenylene diamine. MS (ES+): 509 (M+H).

Example 232

2,N-Dicyclohexyl-2-[2-(2-phenoxy-phenyl)-benzoimidazol-1-yl]-acetamide

In analogy to example 140, 2-Phenoxybenzoic acid, cyclohexanecarbaldehyde, cyclohexyl isocyanide and N-tert-butoxycarbonyl phenylene diamine. MS (ES+): 509 (M+H).

Example 233

2,N-Dicyclohexyl-2-[2-(3-phenoxy-phenyl)-benzoimidazol-1-yl]-acetamide

In analogy to example 140, 3-Phenoxybenzoic acid, cyclohexanecarbaldehyde, cyclohexyl isocyanide and N-tert-butoxycarbonyl phenylene diamine. MS (ES+): 509 (M+H).

Example 234

2,N-Dicyclohexyl-2-{2-[2-(1,1,2,2-tetrafluoro-ethoxy)-phenyl]-benzoimidazol-1-yl}-acetamide In analogy to example 140, 2-(1,1,2,2-Tetrafluoroethoxy) benzoic acid, cyclohexanecarbaldehyde, cyclohexyl isocyanide and N-tert-butoxycarbonyl phenylene diamine. MS (ES+): 532 (M+H).

Example 235

2,N-Dicyclohexyl-2-{2-[3-(1,1,2,2-tetrafluoro-ethoxy)-phenyl]-benzoimidazol-1-yl}-acetamide In analogy to example 140, 3-(1,1,2,2-Tetrafluoroethoxy) benzoic acid, cyclohexanecarbaldehyde, cyclohexyl isocyanide and N-tert-butoxycarbonyl phenylene diamine. MS (ES+): 532 (M+H).

Example 236

2,N-Dicyclohexyl-2-{2-[4-(1,1,2,2-tetrafluoro-ethoxy)-phenyl]-benzoimidazol-1-yl}-acetamide In analogy to example 140, 4-(1,1,2,2-Tetrafluoroethoxy) benzoic acid, cyclohexanecarbaldehyde, cyclohexyl isocyanide and N-tert-butoxycarbonyl phenylene diamine. MS (ES+): 532 (M+H).

Example 237

2,N-Dicyclohexyl-2-[2-(4'-trifluoromethyl-biphenyl-4-yl)-benzoimidazol-1-yl]-acetamide In analogy to example 140, 4'-Trifluoromethyl-biphenyl-4-carboxylic acid, cyclohexanecarbaldehyde, cyclohexyl isocyanide and N-tert-butoxycarbonyl phenylene diamine. MS (ES+): 561 (M+H).

Example 238

2,N-Dicyclohexyl-2-[2-(3',4'-dichloro-biphenyl-4-yl)-benzoimidazol-1-yl]-acetamide In analogy to example 140, 4-(3,4-Dichlorophenyl)benzoic acid, cyclohexanecarbaldehyde, cyclohexyl isocyanide and N-tert-butoxycarbonyl phenylene diamine. MS (ES+): 561 (M+H).

Example 239

2,N-Dicyclohexyl-2-[2-(2,4-dichloro-5-sulfamoyl-phenyl)-benzoimidazol-1-yl]-acetamide In analogy to example 140, 2,4-Dichloro-5-sulfamoylbenzoic acid, cyclohexanecarbaldehyde, cyclohexyl isocyanide and N-tert-butoxycarbonyl phenylene diamine. MS (ES+): 563 (M+H).

Example 240

(S)-2-[6-Chloro-2-(4-chloro-phenyl)-5-fluoro-benzoimidazol-1-yl]-2,N-dicyclohexyl-acetamide In analogy to example 140, 4-Chlorobenzoic acid, cyclohexanecarbaldehyde, cyclohexyl isocyanide and (2-Amino-4-chloro-5-fluoro-phenyl)-carbamic acid tert-butyl ester. MS (ES+): 503 (M+H).

Example 241

2,N-Dicyclohexyl-2-(2-pyridin-2-yl-benzoimidazol-1-yl)-acetamide

In analogy to example 140, Picolinic acid, cyclohexanecarbaldehyde, cyclohexyl isocyanide and N-tert-butoxycarbonyl phenylene diamine. MS (ES+): 417 (M+H).

Example 242

2,N-Dicyclohexyl-2-[2-(6-methyl-pyridin-3-yl)-benzoimidazol-1-yl]-acetamide

In analogy to example 140, 6-Methylnicotinic acid, cyclohexanecarbaldehyde, cyclohexyl isocyanide and N-tert-butoxycarbonyl phenylene diamine. MS (ES+): 431 (M+H).

Example 243

2,N-Dicyclohexyl-2-[2-(3-methyl-pyridin-2-yl)-benzoimidazol-1-yl]-acetamide

In analogy to example 140, 3-Methylnicotinic acid, cyclohexanecarbaldehyde, cyclohexyl isocyanide and N-tert-butoxycarbonyl phenylene diamine. MS (ES+): 431 (M+H).

Example 244

2,N-Dicyclohexyl-2-[2-(6-methyl-pyridin-2-yl)-benzoimidazol-1-yl]-acetamide

In analogy to example 140, 6-Methylpicolinic acid, cyclohexanecarbaldehyde, cyclohexyl isocyanide and N-tert-butoxycarbonyl phenylene diamine. MS (ES+): 431 (M+H).

Example 245

2-[2-(2-Amino-pyridin-3-yl)-benzoimidazol-1-yl]-2,N-dicyclohexyl-acetamide

In analogy to example 140, 2-Aminonicotinic acid, cyclohexanecarbaldehyde, cyclohexyl isocyanide and N-tert-butoxycarbonyl phenylene diamine. MS (ES+): 432 (M+H).

Example 246

2-[2-(6-Cyano-pyridin-3-yl)-benzoimidazol-1-yl]-2,N-dicyclohexyl-acetamide

In analogy to example 140, 6-Cyanonicotinic acid, cyclohexanecarbaldehyde, cyclohexyl isocyanide and N-tert-butoxycarbonyl phenylene diamine. MS (ES+): 442 (M+H).

Example 247

2,N-Dicyclohexyl-2-[2-(2-methoxy-pyridin-3-yl)-benzoimidazol-1-yl]-acetamide

In analogy to example 140, 2-Methoxynicotinic acid, cyclohexanecarbaldehyde, cyclohexyl isocyanide and N-tert-butoxycarbonyl phenylene diamine. MS (ES+): 447 (M+H).

Example 248

2-[2-(2-Chloro-6-methyl-pyridin-3-yl)-benzoimidazol-1-yl]-2,N-dicyclohexyl-acetamide In analogy to example 140, 2-Chloro-6-methylnicotinic acid, cyclohexanecarbaldehyde, cyclohexyl isocyanide and N-tert-butoxycarbonyl phenylene diamine. MS (ES+): 466 (M+H).

Example 249

2-[2-(2-Chloro-6-methyl-pyridin-4-yl)-benzoimidazol-1-yl]-2,N-dicyclohexyl-acetamide In analogy to example 140, 2-Chloro-6-methylpyridine-4-carboxylic acid, cyclohexanecarbaldehyde, cyclohexyl isocyanide and N-tert-butoxycarbonyl phenylene diamine. MS (ES+): 466 (M+H).

Example 250

2,N-Dicyclohexyl-2-(2-quinolin-3-yl-benzoimidazol-1-yl)-acetamide

In analogy to example 140, Quinoline-3-carboxylic acid, cyclohexanecarbaldehyde, cyclohexyl isocyanide and N-tert-butoxycarbonyl phenylene diamine. MS (ES+): 467 (M+H).

Example 251

2,N-Dicyclohexyl-2-(2-quinolin-4-yl-benzoimidazol-1-yl)-acetamide

In analogy to example 140, Quinoline-4-carboxylic acid, cyclohexanecarbaldehyde, cyclohexyl isocyanide and N-tert-butoxycarbonyl phenylene diamine. MS (ES+): 467 (M+H).

Example 252

2-[2-(3-Chloro-4-trifluoromethyl-phenyl)-benzoimidazol-1-yl]-2,N-dicyclohexyl-acetamide In analogy to example 140, 3-Chloro-4-trifluoromethyl-benzoic acid, cyclohexanecarbaldehyde, cyclohexyl isocyanide and N-tert-butoxycarbonyl phenylene diamine. MS (ES+): 519 (M+H).

Example 253

(S)-2-[2-(4-Chloro-phenyl)-benzoimidazol-1-yl]-4-methyl-pentanoic acid cyclohexylamide In analogy to example 140, 4-Chlorobenzoic acid, isovaleraldehyde, cyclohexyl isocyanide and N-tert-butoxycarbonyl phenylene diamine. MS (ES+): 424 (M+H).

Example 254

2-(4-Chloro-phenyl)-2-[2-(4-chloro-phenyl)-benzoimidazol-1-yl]-N-cyclohexyl-acetamide In analogy to example 140, 4-Chlorobenzoic acid, 4-chlorobenzaldehyde, cyclohexyl isocyanide and N-tert-butoxycarbonyl phenylene diamine. MS (ES+): 479 (M+H).

Example 255

2-[2-(4-Chloro-phenyl)-benzoimidazol-1-yl]-N-cyclohexyl-2-(4-trifluoromethyl-phenyl)-acetamide In analogy to example 140, 4-Chlorobenzoic acid, 4-(trifluoromethyl)benzaldehyde, cyclohexyl isocyanide and N-tert-butoxycarbonyl phenylene diamine. MS (ES+): 512 (M+H).

Example 256

2-[2-(4-Chloro-phenyl)-benzoimidazol-1-yl]-N-cyclohexyl-2-(3,4-dichloro-phenyl)-acetamide In analogy to example 140, 4-Chlorobenzoic acid, 3,4-dichlorobenzaldehyde, cyclohexyl isocyanide and N-tert-butoxycarbonyl phenylene diamine. MS (ES+): 514 (M+H).

Example 257

2-[2-(4-Chloro-phenyl)-benzoimidazol-1-yl]-N-cyclohexyl-2-(3-methoxy-phenyl)-acetamide In analogy to example 140, 4-Chlorobenzoic acid, 3-methoxybenzaldehyde, cyclohexyl isocyanide and N-tert-butoxycarbonyl phenylene diamine. MS (ES+): 474 (M+H).

Example 258

2-[2-(4-Chloro-phenyl)-benzoimidazol-1-yl]-N-cyclohexyl-2-p-tolyl-acetamide

In analogy to example 140, 4-Chlorobenzoic acid, p-tolualdehyde, cyclohexyl isocyanide and N-tert-butoxycarbonyl phenylene diamine. MS (ES+): 458 (M+H).

Example 259

2-[2-(4-Chloro-phenyl)-benzoimidazol-1-yl]-N-cyclohexyl-2-(3-fluoro-phenyl)-acetamide In analogy to example 140, 4-Chlorobenzoic acid, 3-fluorobenzaldehyde, cyclohexyl isocyanide and N-tert-butoxycarbonyl phenylene diamine. MS (ES+): 462 (M+H).

Example 260

2-[2-(4-Chloro-phenyl)-benzoimidazol-1-yl]-N-cyclohexyl-2-(4-difluoromethoxy-phenyl)-acetamide In analogy to example 140, 4-Chlorobenzoic acid, 4-(difluoromethoxy)benzaldehyde, cyclohexyl isocyanide and N-tert-butoxycarbonyl phenylene diamine. MS (ES+): 510 (M+H).

Example 261

2-[2-(4-Chloro-phenyl)-benzoimidazol-1-yl]-N-cyclohexyl-2-(2,5-difluoro-phenyl)-acetamide In analogy to example 140, 4-Chlorobenzoic acid, 2,5-difluorobenzaldehyde, cyclohexyl isocyanide and N-tert-butoxycarbonyl phenylene diamine. MS (ES+): 480 (M+H).

Example 262

2-[2-(4-Chloro-phenyl)-benzoimidazol-1-yl]-N-cyclohexyl-2-(2-fluoro-5-methoxy-phenyl)-acetamide In analogy to example 140, 4-Chlorobenzoic acid, 2-fluoro-5-methoxybenzaldehyde, cyclohexyl isocyanide and N-tert-butoxycarbonyl phenylene diamine. MS (ES+): 492 (M+H).

Example 263

(S)-2-[2-(5-Chloro-2-fluoro-phenyl)-benzoimidazol-1-yl]-2,N-dicyclohexyl-acetamide In analogy to example 140, 5-Chloro-2-fluorobenzoic acid, cyclohexanecarbaldehyde, cyclohexyl isocyanide and N-tert-butoxycarbonyl phenylene diamine. MS (ES+): 469 (M+H).

Example 264

(S)-2,N-Dicyclohexyl-2-[2-(2,3-dimethoxy-phenyl)-benzoimidazol-1-yl]-acetamide

In analogy to example 140, 2,3-Dimethoxybenzoic acid, cyclohexanecarbaldehyde, cyclohexyl isocyanide and N-tert-butoxycarbonyl phenylene diamine. MS (ES+): 476 (M+H).

Example 265

(S)-2-[2-(3-Chloro-4-methoxy-phenyl)-benzoimidazol-1-yl]-2,N-dicyclohexyl-acetamide In analogy to example 140, 3-Chloro-4-methoxybenzoic acid, cyclohexanecarbaldehyde, cyclohexyl isocyanide and N-tert-butoxycarbonyl phenylene diamine. MS (ES+): 480 (M+H).

Example 266

(S)-2-Cyclohexyl-2-[2-(2,4-dimethoxy-phenyl)-benzoimidazol-1-yl]-N-(2,6-dimethyl-phenyl)-acetamide In analogy to example 140, 2,4-Dimethoxybenzoic acid, cyclohexanecarbaldehyde, 2,6-dimethylphenylisocyanide and N-tert-butoxycarbonyl phenylene diamine. MS (ES+): 498 (M+H).

Example 267

2-[2-(4-Chloro-phenyl)-benzoimidazol-1-yl]-2-cyclohexyl-N-(4,4-difluoro-cyclohexyl)-acetamide In analogy to example 140, 4-Chlorobenzoic acid, cyclohexanecarbaldehyde, 1,1-Difluoro-4-isocyano-cyclohexane and N-tert-butoxycarbonyl phenylene diamine. MS (ES+): 486 (M+H).

Example 268

(S)-2-[2-(4-Chloro-phenyl)-benzoimidazol-1-yl]-2-cyclohexyl-N-(4,4-difluoro-cyclohexyl)-acetamide In analogy to example 140, 4-Chlorobenzoic acid, cyclohexanecarbaldehyde, 1,1-Difluoro-4-isocyano-cyclohexane and N-tert-butoxycarbonyl phenylene diamine. MS (ES+): 486 (M+H).

Example 269

(S)-2-[2-(2-Amino-pyridin-3-yl)-benzoimidazol-1-yl]-2,N-dicyclohexyl-acetamide

In analogy to example 140, 2-Aminonicotinic acid, cyclohexanecarbaldehyde, cyclohexyl isocyanide and N-tert-butoxycarbonyl phenylene diamine. MS (ES+): 432 (M+H).

Example 270

2,N-Dicyclohexyl-2-(6-fluoro-2-pyridin-2-yl-benzoimidazol-1-yl)-acetamide

In analogy to example 140, Picolinic acid, cyclohexanecarbaldehyde, cyclohexyl isocyanide and (2-amino-4-fluorophenyl)-carbamic acid tert-butyl ester. MS (ES+): 432 (M+H).

Example 271

2,N-Dicyclohexyl-2-[2-(2,4-dimethoxy-phenyl)-6-fluoro-benzoimidazol-1-yl]-acetamide In analogy to example 140, 2,4-Dimethoxybenzoic acid, cyclohexanecarbaldehyde, cyclohexyl isocyanide and (2-amino-4-fluoro-phenyl)-carbamic acid tert-butyl ester. MS (ES+): 494 (M+H).

Example 272

2,N-Dicyclohexyl-2-[6-fluoro-2-(4-methoxy-phenyl)-benzoimidazol-1-yl]-acetamide

In analogy to example 140, 4-Methoxybenzoic acid, cyclohexanecarbaldehyde, cyclohexyl isocyanide and (2-amino-4-fluoro-phenyl)-carbamic acid tert-butyl ester. MS (ES+): 464 (M+H).

Example 273

2,N-Dicyclohexyl-2-[2-(2,3-difluoro-phenyl)-6-fluoro-benzoimidazol-1-yl]-acetamide In analogy to example 140, 2,3-Difluorobenzoic acid, cyclohexanecarbaldehyde, cyclohexyl isocyanide and (2-amino-4-fluoro-phenyl)-carbamic acid tert-butyl ester. MS (ES+): 470 (M+H).

Example 274

2,N-Dicyclohexyl-2-[2-(2,3-dimethoxy-phenyl)-6-fluoro-benzoimidazol-1-yl]-acetamide In analogy to example 140, 2,4-Dimethoxybenzoic acid, cyclohexanecarbaldehyde, cyclohexyl isocyanide and (2-amino-4-fluoro-phenyl)-carbamic acid tert-butyl ester. MS (ES+): 494 (M+H).

Example 275

2,N-Dicyclohexyl-2-[2-(2-ethyl-5-methyl-2H-pyrazol-3-yl)-6-fluoro-benzoimidazol-1-yl]-acetamide In analogy to example 140, 1-Ethyl-3-methyl-1H-pyrazole-5-carboxylic acid, cyclohexanecarbaldehyde, cyclohexyl isocyanide and (2-amino-4-fluoro-phenyl)-carbamic acid tert-butyl ester. MS (ES+): 466 (M+H).

Example 276

2,N-Dicyclohexyl-2-[2-(3,5-dimethyl-isoxazol-4-yl)-6-fluoro-benzoimidazol-1-yl]-acetamide In analogy to example 140, 3,5-Dimethylisoxazole-4-carboxylic acid, cyclohexanecarbaldehyde, cyclohexyl isocyanide and (2-amino-4-fluoro-phenyl)-carbamic acid tert-butyl ester. MS (ES+): 453 (M+H).

Example 277

2,N-Dicyclohexyl-2-[6-fluoro-2-(1H-pyrazol-4-yl)-benzoimidazol-1-yl]-acetamide

In analogy to example 140, 4-Pyrazolecarboxylic acid, cyclohexanecarbaldehyde, cyclohexyl isocyanide and (2-amino-4-fluoro-phenyl)-carbamic acid tert-butyl ester. MS (ES+): 424 (M+H).

Example 278

2,N-Dicyclohexyl-2-[2-(1,5-dimethyl-1H-pyrazol-3-yl)-6-fluoro-benzoimidazol-1-yl]-acetamide In analogy to example 140, 1,5-Dimethyl-1H-pyrazole-3-carboxylic acid, cyclohexanecarbaldehyde, cyclohexyl isocyanide and (2-amino-4-fluoro-phenyl)-carbamic acid tert-butyl ester. MS (ES+): 452 (M+H).

Example 279

2,N-Dicyclohexyl-2-[6-fluoro-2-(3-methyl-isoxazol-5-yl)-benzoimidazol-1-yl]-acetamide In analogy to example 140, 3-Methyl-isoxazole-5-carboxylic acid, cyclohexanecarbaldehyde, cyclohexyl isocyanide and (2-amino-4-fluoro-phenyl)-carbamic acid tert-butyl ester. MS (ES+): 439 (M+H).

Example 280

2,N-Dicyclohexyl-2-[6-fluoro-2-(1H-pyrrol-2-yl)-benzoimidazol-1-yl]-acetamide

In analogy to example 140, Pyrrole-2-carboxylic acid, cyclohexanecarbaldehyde, cyclohexyl isocyanide and (2-amino-4-fluoro-phenyl)-carbamic acid tert-butyl ester. MS (ES+): 423 (M+H).

Example 281

2,N-Dicyclohexyl-2-[6-fluoro-2-(3-methyl-thiophen-2-yl)-benzoimidazol-1-yl]-acetamide In analogy to example 140, 3-Methyl-2-thiophenecarboxylic acid, cyclohexanecarbaldehyde, cyclohexyl isocyanide and (2-amino-4-fluoro-phenyl)-carbamic acid tert-butyl ester. MS (ES+): 454 (M+H).

Example 282

N-Benzyl-2-[2-(4-chloro-phenyl)-benzoimidazol-1-yl]-2-cyclohexyl-acetamide

In analogy to example 140, 4-Chlorobenzoic acid, cyclohexanecarbaldehyde, benzyl isocyanide and N-tert-butoxycarbonyl phenylene diamine. MS (ES+): 458 (M+H).

Example 283

N-Butyl-2-[2-(4-chloro-phenyl)-benzoimidazol-1-yl]-2-cyclohexyl-acetamide

In analogy to example 140, 4-Chlorobenzoic acid, cyclohexanecarbaldehyde, butyl isocyanide and N-tert-butoxycarbonyl phenylene diamine. MS (ES+): 424 (M+H).

Example 284

2-[2-(4-Chloro-phenyl)-benzoimidazol-1-yl]-N-cyclohexyl-2-(tetrahydro-pyran-4-yl)-acetamide In analogy to example 140, 4-Chlorobenzoic acid, tetrahydro-pyran-4-carbaldehyde, cyclohexyl isocyanide and N-tert-butoxycarbonyl phenylene diamine. MS (ES+): 452 (M+H).

Example 285

2-[5-Chloro-2-(4-chloro-phenyl)-6-fluoro-benzoimidazol-1-yl]-2,N-dicyclohexyl-acetamide In analogy to example 140, 4-Chlorobenzoic acid, cyclohexanecarbaldehyde, cyclohexyl isocyanide and (2-amino-5-chloro-4-fluoro-phenyl)-carbamic acid tert-butyl ester. MS (ES+): 503 (M+H).

Example 286

2-[2-(4-Chloro-phenyl)-5,6-difluoro-benzoimidazol-1-yl]-2,N-dicyclohexyl-acetamide In analogy to example 140, 4-Chlorobenzoic acid, cyclohexanecarbaldehyde, cyclohexyl isocyanide and (2-amino-4,5-difluoro-phenyl)-carbamic acid tert-butyl ester. MS (ES+): 486 (M+H).

Example 287

2-[2-(4-Chloro-phenyl)-benzoimidazol-1-yl]-2-cyclohexyl-N-(tetrahydro-pyran-4-yl)-acetamide In analogy to example 140, 4-Chlorobenzoic acid, cyclohexanecarbaldehyde, 4-isocyano-tetrahydro-pyran and N-tert-butoxycarbonyl phenylene diamine. MS (ES+): 452 (M+H).

Example 288

2-[2-(4-Chloro-phenyl)-benzoimidazol-1-yl]-2-cyclohexyl-N-cyclopropyl-acetamide

In analogy to example 140, 4-Chlorobenzoic acid, cyclohexanecarbaldehyde, cyclopropyl isocyanide and N-tert-butoxycarbonyl phenylene diamine. MS (ES+): 408 (M+H).

Example 289

2,N-Dicyclohexyl-2-[2-(6-morpholin-4-yl-pyridin-3-yl)-benzoimidazol-1-yl]-acetamide In analogy to example 140, 6-Morpholinnicotinic acid, cyclohexanecarbaldehyde, cyclohexyl isocyanide and N-tert-butoxycarbonyl phenylene diamine. MS (ES+): 502 (M+H).

Example 290

(S)-2-[2-(4-Chloro-phenyl)-benzoimidazol-1-yl]-2-cyclohexyl-N-(tetrahydro-pyran-4-yl)-acetamide In analogy to example 140, 4-Chlorobenzoic acid, cyclohexanecarbaldehyde, 4-isocyano-tetrahydro-pyran and N-tert-butoxycarbonyl phenylene diamine. MS (ES+): 452 (M+H).

Example 291

(S)-2,N-Dicyclohexyl-2-[2-(4-methanesulfonyl-phenyl)-benzoimidazol-1-yl]-acetamide In analogy to example 140, 4-(Methylsulfonyl)benzoic acid, cyclohexanecarbaldehyde, cyclohexyl isocyanide and N-tert-butoxycarbonyl phenylene diamine. MS (ES+): 494 (M+H).

Example 292

(S)-2-[2-(4-Chloro-phenyl)-benzoimidazol-1-yl]-2-cyclohexyl-N-cyclopropyl-acetamide In analogy to example 140, 4-Chlorobenzoic acid, cyclohexanecarbaldehyde, cyclopropyl isocyanide and N-tert-butoxycarbonyl phenylene diamine. MS (ES+): 408 (M+H).

Example 293

2-[6-Chloro-2-(4-chloro-phenyl)-5-fluoro-benzoimidazol-1-yl]-N-cyclohexyl-2-(tetrahydro-pyran-4-yl)-acetamide In analogy to example 140, 4-Chlorobenzoic acid, tetrahydro-pyran-4-carbaldehyde, cyclohexyl isocyanide and (2-amino-4-chloro-5-fluoro-phenyl)-carbamic acid tert-butyl ester. MS (ES+): 505 (M+H).

Example 294

(S)-2-[2-(4-Chloro-phenyl)-benzoimidazol-1-yl]-N-cyclohexyl-2-(tetrahydro-pyran-4-yl)-acetamide In analogy to example 140, 4-Chlorobenzoic acid, tetrahydro-pyran-4-carbaldehyde, cyclohexyl isocyanide and N-tert-butoxycarbonyl phenylene diamine. MS (ES+): 452 (M+H).

Example 295

(S)-2-[6-Chloro-2-(4-chloro-phenyl)-5-fluoro-benzoimidazol-1-yl]-N-cyclohexyl-2-(tetrahydro-pyran-4-yl)-acetamide In analogy to example 140, 4-Chlorobenzoic acid, tetrahydro-pyran-4-carbaldehyde, cyclohexyl isocyanide and (2-amino-4-chloro-5-fluoro-phenyl)-carbamic acid tert-butyl ester. MS (ES+): 505 (M+H).

Example 296

(S)-2-[2-(4-Chloro-phenyl)-5,6-difluoro-benzoimidazol-1-yl]-2,N-dicyclohexyl-acetamide In analogy to example 140, 4-Chlorobenzoic acid, cyclohexanecarbaldehyde, cyclohexyl isocyanide and (2-amino-4,5-difluoro-phenyl)-carbamic acid tert-butyl ester. MS (ES+): 487 (M+H).

Example 297

(S)-2-[2-(5-Chloro-thiophen-2-yl)-benzoimidazol-1-yl]-2,N-dicyclohexyl-acetamide In analogy to example 140, 5-Chlorothiophene-2-carboxylic acid, cyclohexanecarbaldehyde, cyclohexyl isocyanide and N-tert-butoxycarbonyl phenylene diamine. MS (ES+): 456 (M+H).

Example 298

(S)-2,N-Dicyclohexyl-2-[2-(2,3-difluoro-phenyl)-6-fluoro-benzoimidazol-1-yl]-acetamide In analogy to example 140, 2,3-Difluorobenzoic acid, cyclohexanecarbaldehyde, cyclohexyl isocyanide and (2-amino-4-fluoro-phenyl)-carbamic acid tert-butyl ester. MS (ES+): 470 (M+H).

Example 299

2-[6-Chloro-2-(4-chloro-phenyl)-5-fluoro-benzoimidazol-1-yl]-N-cyclohexyl-2-cyclopentyl-acetamide In analogy to example 140, 4-Chlorobenzoic acid, cyclopentanecarbaldehyde, cyclohexyl isocyanide and (2-amino-4-chloro-5-fluoro-phenyl)-carbamic acid tert-butyl ester. MS (ES+): 489 (M+H).

Example 300

(S)-2-[6-Chloro-2-(4-chloro-phenyl)-5-fluoro-benzoimidazol-1-yl]-heptanoic acid cyclohexylamide In analogy to example 140, 4-Chlorobenzoic acid, hexanal, cyclohexyl isocyanide and (2-amino-4-chloro-5-fluoro-phenyl)-carbamic acid tert-butyl ester. MS (ES+): 491 (M+H).

Example 301

(S)-2-[6-Chloro-2-(4-chloro-phenyl)-5-fluoro-benzoimidazol-1-yl]-N-cyclohexyl-2-cyclopentyl-acetamide In analogy to example 140, 4-Chlorobenzoic acid, cyclopentanecarbaldehyde, cyclohexyl isocyanide and (2-amino-4-chloro-5-fluoro-phenyl)-carbamic acid tert-butyl ester. MS (ES+): 489 (M+H).

Example 302

2-[2-(4-Chloro-phenyl)-5-fluoro-benzoimidazol-1-yl]-2,N-dicyclohexyl-acetamide

4-Chlorobenzoic acid (156.6 mg, 1 mmol, 1 equiv.) was added to a solution of cyclohexanecarbaldehyde (168.3 mg, 1.5 mmol, 1.5 equiv.), cyclohexyl isocyanide (109.2 g, 1 mmol, 1 equiv.) and (2-amino-5-fluoro-phenyl)-carbamic acid allyl ester (210.2 mg, 1 mmol, 1 equiv.) in methanol (15 mL) and the mixture was stirred at room temperature for 16 hours. The solvent was evaporated and the crude product extracted from ethyl acetate and aq. NaHCO$_3$. After separation of the organic layer and evaporation of the solvent, the residue was taken up in Acetonitril. Morpholine (435.5 mg. 5 mmol, 5 equiv.) and etrakis(triphenylphosphine)palladium (231.1 mg, 0.2 mmol, 0.2 equiv.) were added and the mixture stirred at room temperature for 3 hours. The solvent was evaporated and the crude product extracted from ethyl acetate and aq. NaHCO$_3$. After separation of the organic layer and evaporation of the solvent, the residue was taken up in acetic acid. The mixture was stirred at 80° C. for 16 hours. The solvent was evaporated and the product isolated via preperative HPLC. MS (ES+): 469 (M+H).

Example 303

2-[1-(Cyclohexyl-cyclohexylcarbamoyl-methyl)-5,6-difluoro-1H-benzoimidazol-2-yl]-benzoic acid methyl ester In analogy to example 140, Phthalic acid monomethyl ester, cyclohexanecarbaldehyde, cyclohexyl isocyanide and (2-amino-4,5-difluoro-phenyl)-carbamic acid tert-butyl ester. MS (ES+): 510 (M+H).

Example 304

2,N-Dicyclohexyl-2-(5,6-difluoro-2-pyridin-2-yl-benzoimidazol-1-yl)-acetamide

In analogy to example 140, Pipecolic acid, cyclohexanecarbaldehyde, cyclohexyl isocyanide and (2-amino-4,5-difluoro-phenyl)-carbamic acid tert-butyl ester. MS (ES+): 453 (M+H).

Example 305

2-[2-(5-Chloro-thiophen-2-yl)-5,6-difluoro-benzoimidazol-1-yl]-2,N-dicyclohexyl-acetamide In analogy to example 140, 5-Chlorothiophene-2-carboxylic acid, cyclohexanecarbaldehyde, cyclohexyl isocyanide and (2-amino-4,5-difluoro-phenyl)-carbamic acid tert-butyl ester. MS (ES+): 493 (M+H).

Example 306

2-[6-Chloro-1-(cyclohexyl-cyclohexylcarbamoyl-methyl)-5-fluoro-1H-benzoimidazol-2-yl]-benzoic acid methyl ester In analogy to example 140, Phthalic acid monomethyl ester, cyclohexanecarbaldehyde, cyclohexyl isocyanide and (2-amino-4-chloro-5-fluoro-phenyl)-carbamic acid tert-butyl ester. MS (ES+): 526 (M+H).

Example 307

2-(6-Chloro-5-fluoro-2-pyridin-2-yl-benzoimidazol-1-yl)-2,N-dicyclohexyl-acetamide In analogy to example 140, Pipecolic Acid, cyclohexanecarbaldehyde, cyclohexyl isocyanide and (2-amino-4-chloro-5-fluoro-phenyl)-carbamic acid tert-butyl ester. MS (ES+): 469 (M+H).

Example 308

2-(6-Chloro-5-fluoro-2-pyridin-3-yl-benzoimidazol-1-yl)-2,N-dicyclohexyl-acetamide In analogy to example 140, Nicotinic Acid, cyclohexanecarbaldehyde, cyclohexyl isocyanide and (2-amino-4-chloro-5-fluoro-phenyl)-carbamic acid tert-butyl ester. MS (ES+): 469 (M+H).

Example 309

2-(6-Chloro-5-fluoro-2-pyridin-4-yl-benzoimidazol-1-yl)-2,N-dicyclohexyl-acetamide In analogy to example 140, Isonicotinic Acid, cyclohexanecarbaldehyde, cyclohexyl isocyanide and (2-amino-4-chloro-5-fluoro-phenyl)-carbamic acid tert-butyl ester. MS (ES+): 469 (M+H).

Example 310

2-[6-Chloro-2-(3-chloro-thiophen-2-yl)-5-fluoro-benzoimidazol-1-yl]-2,N-dicyclohexyl-acetamide In analogy to example 140, 3-Chlorothiophene-2-carboxylic acid, cyclohexanecarbaldehyde, cyclohexyl isocyanide and (2-amino-4-chloro-5-fluoro-phenyl)-carbamic acid tert-butyl ester. MS (ES+): 509 (M+H).

Example 311

2-[6-Chloro-2-(5-chloro-thiophen-2-yl)-5-fluoro-benzoimidazol-1-yl]-2,N-dicyclohexyl-acetamide In analogy to example 140, 5-Chlorothiophene-2-carboxylic acid, cyclohexanecarbaldehyde, cyclohexyl isocyanide and (2-amino-4-chloro-5-fluoro-phenyl)-carbamic acid tert-butyl ester. MS (ES+): 509 (M+H).

Example 312

(S)-2-[6-Chloro-2-(4-chloro-phenyl)-5-fluoro-benzoimidazol-1-yl]-3-ethyl-pentanoic acid cyclohexylamide In analogy to example 140, 4-Chlorobenzoic acid, 2-ethylbutyraldehyde, cyclohexyl isocyanide and (2-amino-4-chloro-5-fluoro-phenyl)-carbamic acid tert-butyl ester. MS (ES+): 491 (M+H).

Example 313

2-[6-Chloro-5-fluoro-2-(4-fluoro-phenyl)-benzoimidazol-1-yl]-2,N-dicyclohexyl-acetamide In analogy to example 140, 4-Fluorobenzoic acid, cyclohexanecarbaldehyde, cyclohexyl isocyanide and (2-amino-4-chloro-5-fluoro-phenyl)-carbamic acid tert-butyl ester. MS (ES+): 491 (M+H).

Example 314

2-[2-(4-Chloro-phenyl)-benzoimidazol-1-yl]-2-cyclohexyl-N-(1-isopropyl-2-methyl-propyl)-acetamide In analogy to example 140, 4-Chlorobenzoic acid, cyclohexanecarbaldehyde, 1-isopropyl-2-methylpropyl isocyanide and N-tert-butoxycarbonyl phenylene diamine. MS (ES+): 466 (M+H).

Example 315

2-[6-Chloro-2-(4-chloro-phenyl)-5-fluoro-benzoimidazol-1-yl]-2-cyclohexyl-N-cyclopentyl-acetamide In analogy to example 140, 4-Chlorobenzoic acid, cyclohexenecarbaldehyde, cyclopentyl isocyanide and (2-amino-4-chloro-5-fluoro-phenyl)-carbamic acid tert-butyl ester. MS (ES+): 489 (M+H).

Example 316

2-[2-(4-Chloro-phenyl)-5,6-difluoro-benzoimidazol-1-yl]-N-cyclohexyl-2-(tetrahydro-pyran-4-yl)-acetamide In analogy to example 140, 4-Chlorobenzoic acid, tetrahydro-pyran-4-carbaldehyde, cyclohexyl isocyanide and (2-amino-4,5-difluoro-phenyl)-carbamic acid tert-butyl ester. MS (ES+): 488 (M+H).

Example 317

(S)-2-[2-(4-Chloro-phenyl)-5-fluoro-benzoimidazol-1-yl]-2,N-dicyclohexyl-acetamide In analogy to example 302, 4-Chlorobenzoic acid, cyclohexanecarbaldehyde, cyclohexyl isocyanide and (2-amino-5-fluoro-phenyl)-carbamic acid allyl ester. MS (ES+): 468 (M+H).

Example 318

2-[2-(4-Chloro-phenyl)-5,6-difluoro-benzoimidazol-1-yl]-2-cyclohexyl-N-(tetrahydro-pyran-4-yl)-acetamide In analogy to example 140, 4-Chlorobenzoic acid, cyclohexanecarbaldehyde, 4-isocyano-tetrahydro-pyran and (2-amino-4,5-difluoro-phenyl)-carbamic acid tert-butyl ester. MS (ES+): 489 (M+H).

Example 319

2-[6-Chloro-2-(4-chloro-phenyl)-5-fluoro-benzoimidazol-1-yl]-2-cyclohexyl-N-(tetrahydro-pyran-4-yl)-acetamide In analogy to example 140, 4-Chlorobenzoic acid, cyclohexanecarbaldehyde, 4-isocyano-tetrahydro-pyran and (2-amino-4-chloro-5-fluoro-phenyl)-carbamic acid tert-butyl ester. MS (ES+): 505 (M+H).

Example 320

2,N-Dicyclohexyl-2-[2-(3-dimethylamino-phenyl)-5,6-difluoro-benzoimidazol-1-yl]-acetamide In analogy to example 140, 3-Dimethylaminobenzoic acid, cyclohexanecarbaldehyde, cyclohexyl isocyanide and (2-amino-4,5-difluoro-phenyl)-carbamic acid tert-butyl ester. MS (ES+): 495 (M+H).

Example 321

2,N-Dicyclohexyl-2-[2-(3-dimethylamino-phenyl)-6-fluoro-benzoimidazol-1-yl]-acetamide In analogy to example 140, 3-Dimethylaminobenzoic acid, cyclohexanecarbaldehyde, cyclohexyl isocyanide and (2-amino-4-fluoro-phenyl)-carbamic acid tert-butyl ester. MS (ES+): 477 (M+H).

Example 322

2-[2-(4-Chloro-phenyl)-5,6-difluoro-benzoimidazol-1-yl]-2-cyclohexyl-N-(1-isopropyl-2-methyl-propyl)-acetamide In analogy to example 140, 4-Chlorobenzoic acid, cyclohexanecarbaldehyde, 1-isopropyl-2-methylpropyl isocyanide and (2-amino-4,5-difluoro-phenyl)-carbamic acid tert-butyl ester. MS (ES+): 503 (M+H).

Example 323

2-[6-Chloro-2-(4-chloro-phenyl)-5-fluoro-benzoimidazol-1-yl]-2-cyclohexyl-N-(1-isopropyl-2-methyl-propyl)-acetamide In analogy to example 140, 4-Chlorobenzoic acid, cyclohexanecarbaldehyde, 1-isopropyl-2-methylpropyl isocyanide and (2-amino-4-chloro-5-fluoro-phenyl)-carbamic acid tert-butyl ester. MS (ES+): 519 (M+H).

Example 324

2-[2-(3-Chloro-phenyl)-5,6-difluoro-benzoimidazol-1-yl]-2,N-dicyclohexyl-acetamide In analogy to example 140, 3-Chlorobenzoic acid, cyclohexanecarbaldehyde, cyclohexyl isocyanide and (2-amino-4,5-difluoro-phenyl)-carbamic acid tert-butyl ester. MS (ES+): 487 (M+H).

Example 325

2-[2-(2-Chloro-phenyl)-5,6-difluoro-benzoimidazol-1-yl]-2,N-dicyclohexyl-acetamide In analogy to example 140, 2-Chlorobenzoic acid, cyclohexanecarbaldehyde, cyclohexyl isocyanide and (2-amino-4,5-difluoro-phenyl)-carbamic acid tert-butyl ester. MS (ES+): 487 (M+H).

Example 326

(S)-2-[6-Chloro-5-fluoro-2-(4-fluoro-phenyl)-benzoimidazol-1-yl]-2,N-dicyclohexyl-acetamide In analogy to example 140, 4-Fluorobenzoic acid, cyclohexanecarbaldehyde, cyclohexyl isocyanide and (2-amino-4-chloro-5-fluoro-phenyl)-carbamic acid tert-butyl ester. MS (ES+): 487 (M+H).

Example 327

(S)-2-[2-(4-Chloro-phenyl)-5,6-difluoro-benzoimidazol-1-yl]-N-cyclohexyl-2-(tetrahydro-pyran-4-yl)-acetamide In analogy to example 140, 4-Chlorobenzoic acid, tetrahydro-pyran-4-carbaldehyde, cyclohexyl isocyanide and (2-amino-4,5-difluoro-phenyl)-carbamic acid tert-butyl ester. MS (ES+): 488 (M+H).

Example 328

2-[2-(4-Chloro-phenyl)-5-fluoro-benzoimidazol-1-yl]-N-cyclohexyl-2-(tetrahydro-pyran-4-yl)-acetamide In analogy to example 302, 4-Chlorobenzoic acid, tetrahydro-pyran-4-carbaldehyde, cyclohexyl isocyanide and (2-amino-5-fluoro-phenyl)-carbamic acid allyl ester. MS (ES+): 470 (M+H).

Example 329

2-[2-(4-Chloro-phenyl)-6-fluoro-benzoimidazol-1-yl]-N-cyclohexyl-2-(tetrahydro-pyran-4-yl)-acetamide In analogy to example 140, 4-Chlorobenzoic acid, tetrahydro-pyran-4-carbaldehyde, cyclohexyl isocyanide and (2-amino-4-fluoro-phenyl)-carbamic acid tert-butyl ester. MS (ES+): 470 (M+H).

Example 330

2-[2-(4-Chloro-phenyl)-6-fluoro-benzoimidazol-1-yl]-N-cyclohexyl-2-(tetrahydro-pyran-2-yl)-acetamide In analogy to example 140, 4-Chlorobenzoic acid, tetrahydro-pyran-2-carbaldehyde, cyclohexyl isocyanide and (2-amino-4-fluoro-phenyl)-carbamic acid tert-butyl ester. MS (ES+): 470 (M+H).

Example 331

2-[6-Chloro-2-(4-chloro-phenyl)-5-fluoro-benzoimidazol-1-yl]-N-cyclohexyl-2-(tetrahydro-pyran-2-yl)-acetamide In analogy to example 140, 4-Chlorobenzoic acid, tetrahydro-pyran-2-carbaldehyde, cyclohexyl isocyanide and (2-amino-4-chloro-5-fluoro-phenyl)-carbamic acid tert-butyl ester. MS (ES+): 505 (M+H).

Example 332

(S)-2,N-Dicyclohexyl-2-[6-fluoro-2-(3-methyl-thiophen-2-yl)-benzoimidazol-1-yl]-acetamide In analogy to example 140, 3-Methyl-2-thiophenecarboxylic acid, cyclohexanecarbaldehyde, cyclohexyl isocyanide and (2-amino-4-fluoro-phenyl)-carbamic acid tert-butyl ester. MS (ES+): 454 (M+H).

Example 333

(S)-2-[2-(2-Chloro-phenyl)-5,6-difluoro-benzoimidazol-1-yl]-2,N-dicyclohexyl-acetamide In analogy to example 140, 2-Chlorobenzoic acid, cyclohexanecarbaldehyde, cyclohexyl isocyanide and (2-amino-4,5-difluoro-phenyl)-carbamic acid tert-butyl ester. MS (ES+): 487 (M+H).

Example 334

(S)-2-[2-(4-Chloro-phenyl)-5-fluoro-benzoimidazol-1-yl]-N-cyclohexyl-2-(tetrahydro-pyran-4-yl)-acetamide In analogy to example 302, 4-Chlorobenzoic acid, tetrahydro-pyran-4-carbaldehyde, cyclohexyl isocyanide and (2-amino-5-fluoro-phenyl)-carbamic acid allyl ester. MS (ES+): 470 (M+H).

Example 335

(S)-2-[2-(4-Chloro-phenyl)-6-fluoro-benzoimidazol-1-yl]-N-cyclohexyl-2-(tetrahydro-pyran-4-yl)-acetamide In analogy to example 140, 4-Chlorobenzoic acid, tetrahydro-pyran-4-carbaldehyde, cyclohexyl isocyanide and (2-amino-4-fluoro-phenyl)-carbamic acid tert-butyl ester. MS (ES+): 470 (M+H).

Example 336

(S)-2-[2-(4-Chloro-phenyl)-6-fluoro-benzoimidazol-1-yl]-N-cyclohexyl-2-(R)-tetrahydro-pyran-2-yl-acetamide In analogy to example 140, 4-Chlorobenzoic acid, tetrahydro-pyran-2-carbaldehyde, cyclohexyl isocyanide and (2-amino-4-fluoro-phenyl)-carbamic acid tert-butyl ester. MS (ES+): 470 (M+H).

Example 337

(S)-2-[2-(4-Chloro-phenyl)-6-fluoro-benzoimidazol-1-yl]-N-cyclohexyl-2-(S)-tetrahydro-pyran-2-yl-acetamide In analogy to example 140, 4-Chlorobenzoic acid, tetrahydro-pyran-2-carbaldehyde, cyclohexyl isocyanide and (2-amino-4-fluoro-phenyl)-carbamic acid tert-butyl ester. MS (ES+): 470 (M+H).

Example 338

2-[2-(4-Chloro-phenyl)-5-fluoro-benzoimidazol-1-yl]-N-cyclohexyl-2-(tetrahydro-pyran-2-yl)-acetamide In analogy to example 302, 4-Chlorobenzoic acid, tetrahydro-pyran-2-carbaldehyde, cyclohexyl isocyanide and (2-amino-5-fluoro-phenyl)-carbamic acid allyl ester. MS (ES+): 470 (M+H).

Example 339

2,N-Dicyclohexyl-2-[2-(3,4-dichloro-phenyl)-6-methoxy-benzoimidazol-1-yl]-acetamide In analogy to example 140, 3,4-Dichlorobenzoic acid, cyclohexanecarbaldehyde, cyclohexyl isocyanide and (2-amino-4-methoxy-phenyl)-carbamic acid tert-butyl ester. MS (ES+): 514 (M+H).

Example 340

2-[2-(4-Chloro-phenyl)-6-methoxy-benzoimidazol-1-yl]-2,N-dicyclohexyl-acetamide

In analogy to example 140, 4-Chlorobenzoic acid, cyclohexanecarbaldehyde, cyclohexyl isocyanide and (2-amino-4-methoxy-phenyl)-carbamic acid tert-butyl ester. MS (ES+): 480 (M+H).

Example 341

2-[2-(5-Chloro-thiophen-2-yl)-6-methoxy-benzoimidazol-1-yl]-2,N-dicyclohexyl-acetamide In analogy to example 140, 5-Chloro-thiophene-2-carboxylic acid, cyclohexanecarbaldehyde, cyclohexyl isocyanide and (2-amino-4-methoxy-phenyl)-carbamic acid tert-butyl ester. MS (ES+): 486 (M+H).

Example 342

2-[2-(3-Chloro-4-methoxy-phenyl)-6-methoxy-benzoimidazol-1-yl]-2,N-dicyclohexyl-acetamide In analogy to example 140, 3-Chloro-4-methoxybenzoic acid, cyclohexanecarbaldehyde, cyclohexyl isocyanide and (2-amino-4-methoxy-phenyl)-carbamic acid tert-butyl ester. MS (ES+): 510 (M+H).

Example 343

2-[2-(4-Chloro-3-fluoro-phenyl)-6-methoxy-benzoimidazol-1-yl]-2,N-dicyclohexyl-acetamide In analogy to example 140, 4-Chloro-3-fluorobenzoic acid, cyclohexanecarbaldehyde, cyclohexyl isocyanide and (2-amino-4-methoxy-phenyl)-carbamic acid tert-butyl ester. MS (ES+): 498 (M+H).

Example 344

2-Cyclohexyl-N-cyclopentyl-2-[2-(3,4-dichloro-phenyl)-6-methoxy-benzoimidazol-1-yl]-acetamide In analogy to example 140, 3,4-Dichlorobenzoic acid, cyclohexanecarbaldehyde, cyclopentyl isocyanide and (2-amino-4-methoxy-phenyl)-carbamic acid tert-butyl ester. MS (ES+): 500 (M+H).

Example 345

N-Cyclohexyl-2-cyclopentyl-2-[2-(3,4-dichloro-phenyl)-6-methoxy-benzoimidazol-1-yl]-acetamide In analogy to example 140, 3,4-Dichlorobenzoic acid, cyclopentanecarbaldehyde, cyclohexyl isocyanide and (2-amino-4-methoxy-phenyl)-carbamic acid tert-butyl ester. MS (ES+): 500 (M+H).

Example 346

2-[2-(4-Chloro-phenyl)-6-methoxy-benzoimidazol-1-yl]-2-cyclohexyl-N-cyclopentyl-acetamide In analogy to example 140, 4-Chlorobenzoic acid, cyclohexanecarbaldehyde, cyclopentyl isocyanide and (2-amino-4-methoxy-phenyl)-carbamic acid tert-butyl ester. MS (ES+): 466 (M+H).

Example 347

2-[2-(3-Chloro-phenyl)-6-methoxy-benzoimidazol-1-yl]-2,N-dicyclohexyl-acetamide

In analogy to example 140, 3-Chlorobenzoic acid, cyclohexanecarbaldehyde, cyclohexyl isocyanide and (2-amino-4-methoxy-phenyl)-carbamic acid tert-butyl ester. MS (ES+): 480 (M+H).

Example 348

2,N-Dicyclopentyl-2-[2-(3,4-dichloro-phenyl)-6-methoxy-benzoimidazol-1-yl]-acetamide In analogy to example 140, 3,4-Dichlorobenzoic acid, cyclopentanecarbaldehyde, cyclopentyl isocyanide and (2-amino-4-methoxy-phenyl)-carbamic acid tert-butyl ester. MS (ES+): 486 (M+H).

Example 349

2-[2-(4-Chloro-phenyl)-6-methoxy-benzoimidazol-1-yl]-N-cyclohexyl-2-cyclopentyl-acetamide In analogy to example 140, 4-Chlorobenzoic acid, cyclopentanecarbaldehyde, cyclohexyl isocyanide and (2-amino-4-methoxy-phenyl)-carbamic acid tert-butyl ester. MS (ES+): 466 (M+H).

Example 350

2-[2-(4-Chloro-3-fluoro-phenyl)-6-methoxy-benzoimidazol-1-yl]-2-cyclohexyl-N-cyclopentyl-acetamide In analogy to example 140, 4-Chloro-3-fluorobenzoic acid, cyclohexanecarbaldehyde, cyclopentyl isocyanide and (2-amino-4-methoxy-phenyl)-carbamic acid tert-butyl ester. MS (ES+): 484 (M+H).

Example 351

2-[2-(3-Chloro-4-methoxy-phenyl)-6-methoxy-benzoimidazol-1-yl]-2-cyclohexyl-N-cyclopentyl-acetamide In analogy to example 140, 3-Chloro-4-methoxybenzoic acid, cyclohexanecarbaldehyde, cyclopentyl isocyanide and (2-amino-4-methoxy-phenyl)-carbamic acid tert-butyl ester. MS (ES+): 496 (M+H).

Example 352

2,N-Dicyclohexyl-2-[2-(4-fluoro-phenyl)-6-methoxy-benzoimidazol-1-yl]-acetamide

In analogy to example 140, 4-Fluorobenzoic acid, cyclohexanecarbaldehyde, cyclohexyl isocyanide and (2-amino-4-methoxy-phenyl)-carbamic acid tert-butyl ester. MS (ES+): 464 (M+H).

Example 353

2-[2-(3-Chloro-phenyl)-6-methoxy-benzoimidazol-1-yl]-2-cyclohexyl-N-cyclopentyl-acetamide In analogy to example 140, 3-Chlorobenzoic acid, cyclohexanecarbaldehyde, cyclopentyl isocyanide and (2-amino-4-methoxy-phenyl)-carbamic acid tert-butyl ester. MS (ES+): 466 (M+H).

Example 354

2-[2-(3-Chloro-4-methoxy-phenyl)-6-methoxy-benzoimidazol-1-yl]-N-cyclohexyl-2-cyclopentyl-acetamide In analogy to example 140, 3-Chloro-4-methoxybenzoic acid, cyclopentanecarbaldehyde, cyclohexyl isocyanide and (2-amino-4-methoxy-phenyl)-carbamic acid tert-butyl ester. MS (ES+): 496 (M+H).

Example 355

2-[2-(5-Chloro-thiophen-2-yl)-6-methoxy-benzoimidazol-1-yl]-N-cyclohexyl-2-cyclopentyl-acetamide In analogy to example 140, 5-Chloro-thiophene-2-carboxylic acid, cyclopentanecarbaldehyde, cyclohexyl isocyanide and (2-amino-4-methoxy-phenyl)-carbamic acid tert-butyl ester. MS (ES+): 472 (M+H).

Example 356

2-Cyclobutyl-N-cyclohexyl-2-[2-(3,4-dichloro-phenyl)-6-methoxy-benzoimidazol-1-yl]-acetamide In analogy to example 140, 3,4-Dichlorobenzoic acid, cyclobutanecarbaldehyde, cyclohexyl isocyanide and (2-Amino-4-methoxy-phenyl)-carbamic acid tert-butyl ester. MS (ES+): 486 (M+H).

Example 357

2-[2-(5-Chloro-thiophen-2-yl)-6-methoxy-benzoimidazol-1-yl]-2-cyclohexyl-N-cyclopentyl-acetamide In analogy to example 140, 5-Chloro-thiophene-2-carboxylic acid, cyclohexanecarbaldehyde, cyclopentyl isocyanide and (2-amino-4-methoxy-phenyl)-carbamic acid tert-butyl ester. MS (ES+): 472 (M+H).

Example 358

2-[2-(6-Chloro-pyridin-3-yl)-6-methoxy-benzoimidazol-1-yl]-2,N-dicyclohexyl-acetamide In analogy to example 140, 6-Chloro-nicotinic acid, cyclohexanecarbaldehyde, cyclohexyl isocyanide and (2-amino-4-methoxy-phenyl)-carbamic acid tert-butyl ester. MS (ES+): 481 (M+H).

Example 359

2-[2-(3-Chloro-phenyl)-6-methoxy-benzoimidazol-1-yl]-N-cyclohexyl-2-cyclopentyl-acetamide In analogy to example 140, 3-Chlorobenzoic acid, cyclopentanecarbaldehyde, cyclohexyl isocyanide and (2-amino-4-methoxy-phenyl)-carbamic acid tert-butyl ester. MS (ES+): 466 (M+H).

Example 360

2-[2-(3-Chloro-4-methoxy-phenyl)-6-methoxy-benzoimidazol-1-yl]-2,N-dicyclopentyl-acetamide In analogy to example 140, 3-Chloro-4-methoxybenzoic acid, cyclopentanecarbaldehyde, cyclopentyl isocyanide and (2-amino-4-methoxy-phenyl)-carbamic acid tert-butyl ester. MS (ES+): 482 (M+H).

Example 361

2,N-Dicyclohexyl-2-[6-methoxy-2-(6-trifluoromethyl-pyridin-3-yl)-benzoimidazol-1-yl]-acetamide In analogy to example 140, 6-Trifluoromethyl-nicotinic acid, cyclohexanecarbaldehyde, cyclohexyl isocyanide and (2-amino-4-methoxy-phenyl)-carbamic acid tert-butyl ester. MS (ES+): 515 (M+H).

Example 362

2-[2-(5-Chloro-thiophen-2-yl)-6-methoxy-benzoimidazol-1-yl]-2-cyclobutyl-N-cyclohexyl-acetamide In analogy to example 140, 5-Chloro-thiophene-2-carboxylic acid, cyclobutanecarbaldehyde, cyclohexyl isocyanide and (2-amino-4-methoxy-phenyl)-carbamic acid tert-butyl ester. MS (ES+): 458 (M+H).

Example 363

2-[2-(3-Chloro-phenyl)-6-methoxy-benzoimidazol-1-yl]-2-cyclobutyl-N-cyclohexyl-acetamide In analogy to example 140, 3-Chlorobenzoic acid, cyclobutanecarbaldehyde, cyclohexyl isocyanide and (2-amino-4-methoxy-phenyl)-carbamic acid tert-butyl ester. MS (ES+): 452 (M+H).

Example 364

N-Cyclohexyl-2-cyclopentyl-2-[2-(4-fluoro-phenyl)-6-methoxy-benzoimidazol-1-yl]-acetamide In analogy to example 140, 4-Fluorobenzoic acid, cyclopentanecarbaldehyde, cyclohexyl isocyanide and (2-amino-4-methoxy-phenyl)-carbamic acid tert-butyl ester. MS (ES+): 450 (M+H).

Example 365

(2-Amino-4,5-difluoro-phenyl)-carbamic acid tert-butyl ester 4,5-Difluoro-2-nitro-phenylamine (6.0 g, 34 mmol, 1 equiv.) was added to a solution of di-tert-butyl dicarbonate (14.8 g, 68 mmol, 2 equiv.) and DMAP (211 mg, 0.2 mmol, 0.05 in THF (100 mL) and the mixture was stirred at room temperature for 72 hours. The solvent was evaporated and the crude extracted from ethylacetate and aq. $NaHCO_3$. The residue was taken up in DCM and cooled to 0° C. Trifluoroacetic acid (7.75 g, 68 mmol, 2 equiv) were added slowly and the mixture stirred for 48 h at 0° C. 2 N NaOH was added to adjust the pH to 7. The organic layer was separated and evaporated. The residue was taken up in ethyl acetate and the product extracted from aq. $NaHCO_3$. The intermediate was isolated via Kieselgel chromatography. 4.28 g (16 mmol, 1 equiv.) were dissolved in DMF (50 ml) and 13 ml of a saturated $NH_4Cl$ solution added. Zink powder (5.1 g, 78 mmol, 5 equiv.) was added and the suspension stirred for 30 minutes at 80° C. and another 2 hours at room temperature. The remaining solid was filtered off and the organic layer evaporated. The product was extracted from ethyl acetate and aq. $NaHCO_3$ and further purified via Kieselgel chromatography.

Example 366

(2-Amino-4-fluoro-phenyl)-carbamic acid tert-butyl ester

In analogy to example 365, starting from 4-Fluoro-2-nitro-phenylamine.

Example 367

(2-Amino-4-methoxy-phenyl)-carbamic acid tert-butyl ester

In analogy to example 365, starting from 4-Methoxy-2-nitro-phenylamine.

Example 368

(2-Amino-4-bromo-phenyl)-carbamic acid tert-butyl ester

In analogy to example 365, starting from 4-Bromo-2-nitro-phenylamine.

Example 369

(2-Amino-4-chloro-phenyl)-carbamic acid tert-butyl ester

In analogy to example 365, starting from 4-Chloro-2-nitro-phenylamine.

Example 370

(2-Amino-5-chloro-4-fluoro-phenyl)-carbamic acid tert-butyl ester

In analogy to example 365, starting from 5-Chloro-4-fluoro-2-nitro-phenylamine.

Example 371

(2-Amino-4-chloro-5-fluoro-phenyl)-carbamic acid tert-butyl ester

In analogy to example 365, starting from 4-Chloro-5-fluoro-2-nitro-phenylamine.

Example 372

(2-Amino-5-fluoro-phenyl)-carbamic acid allyl ester (2-Amino-4-fluoro-phenyl)-carbamic acid tert-butyl ester (5.0 g, 22 mmol, 1 equiv.) was added to a solution of DIPEA (3.62 ml, 22 mmol, 1 equiv.) in THF (80 ml). The mixture was cooled to 0° C. and allyl chloroformate (2.36 ml, 22 mmol, 1 equiv.) in THF added. The mixture was stirred at room temperature for 16 hours. The solvent was evaporated and the crude extracted from ethylacetate and aq. NaHCO$_3$. The residue was taken up in DCM and trifluoroacetic acid (1:1) for 2 hours. The product was obtained after evaporation of the organic solvents.

Example 373

1,1-Difluoro-4-isocyano-cyclohexane 4,4-Difluoro-cyclohexylamine hydrochloride (1.0 g, 5.8 mmol, 1 equiv.) was added to a mixture of NaOH (1.5 g, 37 mmol, 6.3 equiv.) and tetrabutylammonium hydrogen sulfate (40 mg, 0.12 mmol, 0.02 equiv.) in water (2.5 ml), chloroform (3 ml, 37 mmol) 6.3 equiv.) and DCM (5 ml). The mixture was stirred at room temperature for 72 h and the crude extracted with DCM. The product was isolated via Kieslgel chromatography.

Example 374

4-Isocyano-tetrahydro-pyran

In analogy to example 373, starting from Tetrahydro-pyran-4-ylamine.

Example 375

Tetrahydro-pyran-2-carbaldehyde

Oxalyl chloride (3.9 g, 31 mmol, 1.2 equiv.) was dissolved in DCM and cooled to −78° C. DMSO (3.7 g, 52 mmol, 2 equiv.) in DCM (10 ml) was added dropwise and the mixture stirred for 20 minutes. Tetrahydropyran-2-methanol (3 g, 26 mmol, 1 equiv.) was dissolved in DCM (10 ml) and added dropwise to the reaction mixture. After 15 minutes triethylamine (18 ml) was added dropwise and the mixture warmed to room temperature. Water was added and the crude extracted with DCM. The product was isolated via Kieselgel chromatography.

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
| --- | --- |
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
| --- | --- |
| Compound of formula (I) | 5.0 mg |
| Yellow wax | 8.0 mg |
| Hydrogenated Soya bean oil | 8.0 mg |
| Partially hydrogenated plant oils | 34.0 mg |

-continued

| | |
|---|---|
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

Unless stated to the contrary, all compounds in the examples were prepared and characterized as described. All ranges recited herein encompass all combinations and sub-combinations included within that range limit. All patents and publications cited herein are hereby incorporated by reference in their entirety.

What is claimed is:
1. A compound of formula (I):

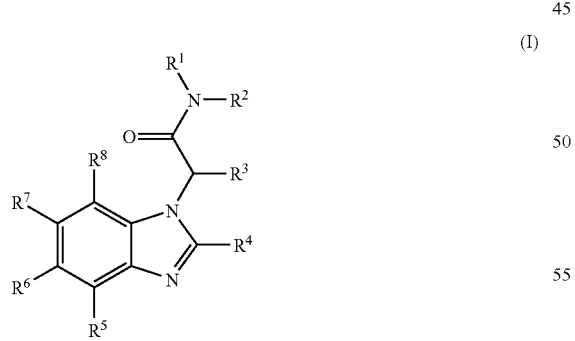

or a pharmaceutically acceptable salt or ester thereof, wherein:
(a) $R^1$ is selected from the group consisting of:
  (1) cycloalkyl optionally substituted 1 or 2 times with halogen,
  (2) phenyl optionally substituted 1 or 2 times with lower alkyl, and
  (3) tetrahydropyranyl;
(b) $R^2$ is hydrogen or lower-alkyl;
(c) $R^3$ is selected from the group consisting of:
  (1) lower-alkyl having at least 3 carbon atoms,
  (2) cycloalkyl,
  (3) partially unsaturated cycloalkyl,
  (4) aryl,
  (5) aryl-lower-alkyl,
  (6) heteroaryl,
  (7) heteroaryl-lower-alkyl,
  (8) heterocylclyl, and
  (9) heterocyclyl-lower-alkyl,
wherein the aryl, heteroaryl or heterocyclyl group of any option for $R^3$ above is optionally substituted with 1 to 3 substituents independently selected from the group consisting of halogen, lower-alkyl, lower-alkoxy, lower-alkoxy-carbonyl, hydroxy, fluoro-lower-alkyl, fluoro-lower-alkoxy, $NH_2$, N(H, lower-alkyl), N(lower-alkyl)$_2$, lower -alkyl-carbonyl-N(lower-alkyl), lower-alkyl-carbonyl-N(H), carboxy, carbamoyl, N(H, lower-alkyl)C(O), and N(lower-alkyl)$_2$C(O);
(d) $R^4$ is selected from the group consisting of:
  (1) heteroaryl which is optionally substituted with 1 to 3 substituents independently selected from the group consisting of lower-alkyl, phenyl, lower-alkoxy -carbonyl, carboxy, carbamoyl, N(H, lower-alkyl)C(O), N(lower-alkyl)$_2$C(O), $NH_2$, N(H, lower-alkyl), N(lower-alkyl)$_2$, lower-alkyl-carbonyl-N(lower-alkyl), lower-alkyl-carbonyl-N(H), hydroxy, lower-alkoxy, halogen, fluoro-lower-alkyl, fluoro-lower-alkoxy, cyano and morpholinyl;
  (2) substituted naphthyl or substituted phenyl, substituted with 1 to 3 substituents independently selected from the group consisting of halogen, hydroxy, $NH_2$, CN, hydroxy-lower-alkyl, lower-alkoxy, lower-alkyl-carbonyl, lower-alkyl-carbonyl-N(H), lower-alkoxy-carbonyl, sulfamoyl, di-lower-alkyl-sulfamoyl, lower-alkyl-sulfonyl, thiophenyl, pyrazolyl, thiadiazolyl, imidazolyl, triazolyl, tetrazolyl, 2-oxo-pyrrolidinyl, pyrrolyl, pyridinyl, pyrimidinyl, 2-oxo-piperidinyl, pyrrolidinyl, piperidinyl, oxazolyl, thiazolyl, oxadiazolyl, carboxy, fluoro-lower-alkyl, fluoro-lower-alkoxy, N(H, lower-alkyl), N(lower-alkyl)$_2$, lower-alkyl-carbonyl-N(lower-alkyl), carbamoyl, N(H, lower-alkyl)C(O), N(lower-alkyl)$_2$C(O), lower-alkyl-sulfamoyl, lower-alkenyl, benzoyl, phenoxy, and phenyl wherein said phenyl is itself optionally substituted with 1 to 3 substituents independently selected from the group consisting of halogen and fluoro-lower-alkyl;
  (3) unsubstituted naphthyl; and
  (4) unsubstituted phenyl or phenyl substituted by lower alkyl if $R^1$ is cycloalkyl and $R^3$ is cycloalkyl; and
(e) $R^5$, $R^6$, $R^7$ and $R^8$ are independently from each other selected from the group consisting of:
  (1) hydrogen,
  (2) halogen, and
  (3) lower-alkyl;
or alternatively, $R^5$ and $R^6$ are bound together, or $R^6$ and $R^7$ are bound together, or $R^7$ and $R^8$ are bound together, to form a 4-7 membered aromatic or non-aromatic carbocyclic or heterocyclic ring together with the carbon atoms to which they are attached.

2. A compound of claim 1, wherein $R^4$ is selected from the group consisting of:
(1) heteroaryl which is optionally substituted with 1 to 3 substituents independently selected from the group consisting of lower-alkyl, phenyl, lower-alkoxy-carbonyl, carboxy, carbamoyl, N(H, lower-alkyl)C(O), N(lower-alkyl)$_2$C(O), NH$_2$, N(H, lower-alkyl), N(lower-alkyl)$_2$, lower-alkyl-carbonyl-N(lower-alkyl), lower-alkyl-carbonyl-N(H), hydroxy, lower-alkoxy, halogen, fluoro-lower-alkyl and fluoro-lower-alkoxy;
(2) substituted naphthyl or substituted phenyl, substituted with 1 to 3 substituents independently selected from the group consisting of halogen, hydroxy, NH$_2$, CN, hydroxy-lower-alkyl, lower-alkoxy, lower-alkyl-carbonyl, lower-alkyl-carbonyl-N(H), lower-alkoxy-carbonyl, sulfamoyl, di-lower-alkyl-sulfamoyl, lower-alkyl-sulfonyl, thiophenyl, pyrazolyl, thiadiazolyl, imidazolyl, triazolyl, tetrazolyl, 2-oxo-pyrrolidinyl, pyrrolyl, pyridinyl, pyrimidinyl, 2-oxo-piperidinyl, pyrrolidinyl, piperidinyl, oxazolyl, thiazolyl, oxadiazolyl, carboxy, fluoro-lower-akyl, fluoro-lower-alkoxy, N(H, lower-alkyl), N(lower-alkyl)$_2$, lower-alkyl-carbonyl-N(lower-alkyl), carbamoyl, N(H, lower-alkyl)C(O), N(lower-alkyl)$_2$C(O), and lower-alkyl-sulfamoyl;
(3) unsubstituted naphthyl; and
(4) unsubstituted phenyl or phenyl substituted by lower alkyl if $R^1$ is cycloalkyl and $R^3$ is cycloalkyl.

3. A compound of claim 1, wherein $R^1$ is cycloalkyl optionally substituted 1 or 2 times with halogen.

4. A compound of claim 1, wherein $R^1$ is cycloalkyl.

5. A compound of claim 1, wherein $R^1$ is cyclopentyl, cyclohexyl or 2,5-dimethyl-phenyl.

6. A compound of claim 1, wherein $R^1$ is tetrahydropyran-4-yl, 4,4-difluoro-cyclohexyl or 2,6-dimethyl-phenyl.

7. A compound of claim 1, wherein $R^2$ is hydrogen.

8. A compound of claim 1, wherein $R^3$ is selected from the group consisting of:
(1) lower-alkyl,
(2) cycloalkyl,
(3) partially unsaturated cycloalkyl,
(4) phenyl,
(5) phenyl-lower-alkyl, and
(6) heteroaryl, which is pyridinyl or benzodioxolyl,
wherein the phenyl or heteroaryl group of any option for $R^3$ above is optionally substituted with 1 to 3 substituents independently selected from the group consisting of halogen, lower-alkyl, lower-alkoxy, NH$_2$, N(H,lower-alkyl), and N(lower-alkyl)$_2$.

9. A compound of formula (I):

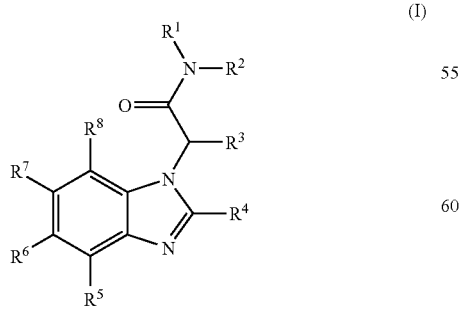

or a pharmaceutically acceptable salt or ester thereof, wherein:

(a) $R^1$ is selected from the group consisting of:
(1) $C_{1-10}$-alkyl,
(2) lower-alkoxy-lower-alkyl,
(3) lower-alkoxy-carbonyl-lower-alkyl,
(4) cycloalkyl,
(5) cycloalkyl-lower-alkyl,
(6) aryl,
(7) aryl-lower-alkyl,
(8) di-aryl-lower-alkyl,
(9) heteroaryl,
(10) heteroaryl-lower-alkyl,
(11) heterocyclyl, and
(12) heterocyclyl-lower-alkyl,
wherein the cycloalkyl, aryl, heteroaryl or heterocyclyl group of any option for $R^1$ above is optionally substituted with 1 to 3 substituents independently selected from the group consisting of: lower-alkyl, lower-alkoxy, lower-alkoxy-carbonyl, morpholinyl, formylamino, halogen, hydroxy, fluoro-lower-alkyl, fluoro-lower-alkoxy, lower-alkyl-carbonyl-N(lower-alkyl), lower-alkyl-carbonyl-N(H), NH$_2$, N(H, lower-alkyl), N(lower-alkyl)$_2$, carboxy, carbamoyl, N(H, lower-alkyl)C(O), and N(lower-alkyl)$_2$C(O);

(b) $R^2$ is hydrogen or lower-alkyl;
(c) $R^3$ is selected from the group consisting of:
(1) cycloalkyl,
(2) phenyl,
(3) phenyl-lower-alkyl, and
(4) pyridinyl;
wherein said cycloalkyl, phenyl, phenyl-lower-alkyl, or pyridinyl group of any option for $R^3$ above is optionally substituted with 1 to 3 substituents independently selected from the group consisting of halogen, lower-alkyl, lower-alkoxy, lower-alkoxy-carbonyl, hydroxy, fluoro-lower-alkyl, fluoro-lower-alkoxy, NH$_2$, N(H, lower-alkyl), N(lower-alkyl)$_2$, lower-alkyl-carbonyl-N(lower-alkyl), lower-alkyl-carbonyl-N(H), carboxy, carbamoyl, N(H, lower-alkyl)C(O), and N(lower-alkyl)$_2$C(O);

(d) $R^4$ is selected from the group consisting of:
(1) heteroaryl which is optionally substituted with 1 to 3 sub stituents independently selected from the group consisting of lower-alkyl, phenyl, lower-alkoxy-carbonyl, carboxy, carbamoyl, N(H, lower-alkyl)C(O), N(lower-alkyl)$_2$C(O), NH$_2$, N(H, lower-alkyl), N(lower-alkyl)$_2$, lower-alkyl-carbonyl-N(lower-alkyl), lower-alkyl-carbonyl-N(H), hydroxy, lower-alkoxy, halogen, fluoro-lower-alkyl, fluoro-lower-alkoxy, cyano and morpholinyl;
(2) substituted naphthyl or substituted phenyl, substituted with 1 to 3 substituents independently selected from the group consisting of halogen, hydroxy, NH$_2$, CN, hydroxy-lower-alkyl, lower-alkoxy, lower-alkyl-carbonyl, lower-alkyl-carbonyl-N(H), lower-alkoxy-carbonyl, sulfamoyl, di-lower-alkyl-sulfamoyl, lower-alkyl-sulfonyl, thiophenyl, pyrazolyl, thiadiazolyl, imidazolyl, triazolyl, tetrazolyl, 2-oxo-pyrrolidinyl, pyrrolyl, pyridinyl, pyrimidinyl, 2-oxo-piperidinyl, pyrrolidinyl, piperidinyl, oxazolyl, thiazolyl, oxadiazolyl, carboxy, fluoro-lower-alkyl, fluoro-lower-alkoxy, N(H, lower-alkyl), N(lower-alkyl)$_2$, lower-alkyl-carbonyl-N(lower-alkyl), carbamoyl, N(H, lower-alkyl)C(O), N(lower-alkyl)$_2$C(O), lower-alkyl-sulfamoyl, lower-alkenyl, benzoyl, phenoxy, and phenyl wherein said phenyl is itself optionally substituted with 1 to 3 substituents independently selected from the group consisting of halogen and fluoro-lower-alkyl;
(3) unsubstituted naphthyl; and
(4) unsubstituted phenyl or phenyl substituted by lower alkyl if $R^1$ is cycloalkyl and $R^3$ is cycloalkyl; and
(e) $R^5$, $R^6$, $R^7$ and $R^8$ are independently from each other selected from the group consisting of:
(1) hydrogen,
(2) halogen, and
(3) lower-alkyl;
or alternatively, $R^5$ and $R^6$ are bound together, or $R^6$ and $R^7$ are bound together, or $R^7$ and $R^8$ are bound together, to form a 4-7 membered aromatic or non-aromatic carbocyclic or heterocyclic ring together with the carbon atoms to which they are attached.

10. A compound of claim 9, wherein $R^3$ is cyclopentyl, cyclohexyl, phenyl, 3-phenyl-propyl, or pyridin-2-yl.

11. A compound of claim 9, wherein $R^3$ is phenyl substituted with 1 to 3 substituents independently selected from the group consisting of fluoro-lower-alkyl and fluoro-lower-alkoxy.

12. A compound of claim 9, wherein $R^3$ is cycloalkyl.

13. A compound of 9, wherein $R^4$ is selected from the group consisting of:
(1) heteroaryl selected from the group consisting of thiophenyl, pyrrolyl, 2-oxo-1,2-dihydro-pyridinyl, indolyl, quinolinyl and 1,3-dioxo-isoindolyl, wherein said heteroaryl is optionally substituted with 1 to 2 substituents independently selected from the group consisting of lower-alkyl and phenyl;
(2) substituted naphthyl or substituted phenyl, substituted with 1 to 3 substituents independently selected from the group consisting of halogen, hydroxy, $NH_2$, CN, hydroxy-lower-alkyl, lower-alkoxy, lower-alkyl-carbonyl, lower-alkyl-carbonyl-N(H), lower-alkoxy-carbonyl, sulfamoyl, di-lower-alkyl-sulfamoyl, lower-alkyl-sulfonyl, thiophenyl, pyrazolyl, thiadiazolyl, imidazolyl, triazolyl, tetrazolyl, and 2-oxo-pyrrolidinyl;
(3) unsubstituted naphthyl; and
(4) unsubstituted phenyl if $R^1$ is cycloalkyl and $R^3$ is cycloalkyl.

14. A compound of formula (I):

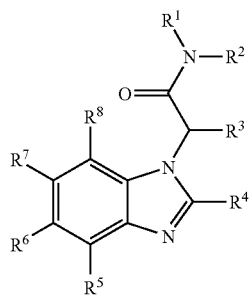

(I)

or a pharmaceutically acceptable salt or ester thereof, wherein:
(a) $R^1$ is selected from the group consisting of:
(1) $C_{1-10}$-alkyl,
(2) lower-alkoxy-lower-alkyl,
(3) lower-alkoxy-carbonyl-lower-alkyl,
(4) cycloalkyl,
(5) cycloalkyl-lower-alkyl,
(6) aryl,
(7) aryl-lower-alkyl,
(8) di-aryl-lower-alkyl,
(9) heteroaryl,
(10) heteroaryl-lower-alkyl,
(11) heterocyclyl, and
(12) heterocyclyl-lower-alkyl,
wherein the aryl, heteroaryl or heterocyclyl group of any option for $R^1$ above is optionally substituted with 1 to 3 substituents independently selected from the group consisting of halogen, lower-alkyl, lower-alkoxy, lower-alkoxy-carbonyl, hydroxy, fluoro-lower-alkyl, fluoro-lower-alkoxy, $NH_2$, N(H, lower-alkyl), N(lower-alkyl)$_2$, lower -alkyl-carbonyl-N(lower-alkyl), lower-alkyl-carbonyl-N(H), carboxy, carbamoyl, N(H, lower-alkyl)C(O), and N(lower-alkyl)$_2$C(O);
(b) $R^2$ is hydrogen or lower-alkyl;
(c) $R^3$ is selected from the group consisting of:
(1) lower-alkyl,
(2) cycloalkyl,
(3) partially unsaturated cycloalkyl,
(4) aryl,
(5) aryl-lower-alkyl,
(6) heteroaryl,
(7) heteroaryl-lower-alkyl,
(8) heterocylclyl, and
(9) heterocyclyl-lower-alkyl,
wherein the aryl, heteroaryl or heterocyclyl group of any option for $R^3$ above is optionally substituted with 1 to 3 substituents independently selected from the group consisting of halogen, lower-alkyl, lower-alkoxy, lower-alkoxy-carbonyl, hydroxy, fluoro-lower-alkyl, fluoro-lower-alkoxy, $NH_2$, N(H, lower-alkyl), N(lower-alkyl)$_2$, lower -alkyl-carbonyl-N(lower-alkyl), lower-alkyl-carbonyl-N(H), carboxy, carbamoyl, N(H, lower-alkyl)C(O), and N(lower-alkyl)$_2$C(O);
(d) $R^4$ is selected from the group consisting of:
(1) heteroaryl selected from the group consisting of thiophenyl, 2-oxo-1,2-dihydro-pyridinyl, 1-methyl-1H-pyrrol-2-yl, and quinolinyl, wherein said thiophenyl is optionally substituted with phenyl, and
(2) substituted naphthyl or substituted phenyl, substituted with 1 to 2 substituents independently selected from the group consisting of cyano, hydroxy, hydroxy-lower-alkyl, lower-alkyl-carbonyl, lower-alkoxy, lower-alkoxy-carbonyl, lower -alkyl-carbonyl-N(H), imidazolyl, and tetrazolyl,
(3) unsubstituted naphthyl, and
(4) unsubstituted phenyl if $R^1$ is cycloalkyl and Ri is cycloalkyl; and
(e) $R^5$, $R^6$, $R^7$ and $R^8$ are independently from each other selected from the group consisting of:
(1) hydrogen,
(2) halogen, and
(3) lower-alkyl;
or alternatively, $R^5$ and $R^6$ are bound together, or $R^6$ and $R^7$ are bound together, or $R^7$ and $R^8$ are bound together, to form a 4-7 membered aromatic or non-aromatic carbocyclic or heterocyclic ring together with the carbon atoms to which they are attached.

15. A compound of claim 14, wherein $R^4$ is 2,4-dimethoxyphenyl, napthalen-2-yl, 4-hydroxymethyl-phenyl, 4-(tetrazolyl-5-yl)-phenyl, 4-(imidazol-2-yl)-phenyl, 4-acetylamino-phenyl, 5-phenyl-thiophen-2-yl, 2-oxo-1,2-dihydropyridin-4-yl, or quinolin-6-yl.

16. A compound of claim 14, wherein $R^4$ is substituted phenyl.

17. A compound of claim 14, wherein wherein $R^4$ is thiophenyl.

18. A compound of claim 1, wherein $R^4$ is 5-chloro-thiophen-2-yl, 2-aminocarbonyl-phenyl, or 4-chloro-phenyl.

19. A compound of claim 1, wherein $R^5$, $R^6$, $R^7$ and $R^8$ independently from each other are selected from the group consisting of hydrogen, halogen, lower-alkyl, and lower-alkoxy; or alternatively, $R^6$ and $R^7$ are bound together to form a 6-membered aromatic carbocyclic ring together with the carbon atoms to which they are attached, and $R^5$ and $R^8$ independently from each other are selected from the group consisting of hydrogen, halogen, lower-alkyl, and lower-alkoxy.

20. A compound of claim 1, wherein $R^5$ is hydrogen.

21. A compound of claim 1, wherein $R^6$ is hydrogen, fluoro or methyl.

22. A compound of claim 1, wherein $R^7$ is hydrogen, fluoro or chloro.

23. A compound of claim 1, wherein $R^8$ is hydrogen.

24. A compound of claim 1, selected from the group consisting of:
  2,N-dicyclohexyl-2-(2-phenyl-benzoimidazol-1-yl)-acetamide hydrogen chloride,
  2-[2-(4-chloro-phenyl)-benzoimidazol-1-yl]-4-methyl-pentanoic acid cyclohexylamide,
  2,N-dicyclohexyl-2-[5,6-dichloro-2-(2,4-dimethoxy-phenyl)-benzoimidazol-1-yl]-acetamide,
  2,N-dicyclohexyl-2-[2-(4-methoxy-phenyl)-benzoimidazol-1-yl]-acetamide hydrogen chloride,
  2,N-dicyclohexyl-2-[2-(3-methoxy-phenyl)-benzoimidazol-1-yl]-acetamide hydrogen chloride,
  2,N-dicyclohexyl-2-[2-(2-methoxy-phenyl)-benzoimidazol-1-yl]-acetamide hydrogen chloride,
  2,N-dicyclohexyl-2-(2-naphthalen-1-yl-benzoimidazol-1-yl)-acetamide hydrogen chloride,
  2,N-dicyclohexyl-2-[2-(3-ethoxy-phenyl)-benzoimidazol-1-yl]-acetamide hydrogen chloride,
  and any pharmaceutically acceptable salt or ester thereof.

25. A compound of claim 1, selected from the group consisting of:
  N-cyclohexyl-2-[2-(2,4-dimethoxy-phenyl)-benzoimidazol-1-yl]-4-phenyl-butyramide,
  N-cyclohexyl-2-[2-(2,4-dimethoxy-phenyl)-benzoimidazol-1-yl]-3-methyl-butyramide hydrogen chloride,
  N-cyclohexyl-2-[2-(2,4-dimethoxy-phenyl)-benzoimidazol-1-yl]-3-phenyl-propionamide hydrogen chloride,
  N-cyclohexyl-2-[2-(2,4-dimethoxy-phenyl)-benzoimidazol-1-yl]-2-pyridin-2-yl-acetamide hydrogen chloride,
  N-cyclohexyl-2-cyclopentyl-2-[2-(2,4-dimethoxy-phenyl)-benzoimidazol-1-yl]-acetamide hydrogen chloride,
  4-{1-[cyclohexyl-(cyclohexylcarbamoyl-methyl)]-1H-benzoimidazol-2-yl}-benzoic acid methyl ester,
  2,N-dicyclohexyl-2-(2-naphthalen-2-yl-benzoimidazol-1-yl)-acetamide,
  2,N-dicyclohexyl-2-[2-(3-thiophen-2-yl-phenyl)-benzoimidazol-1-yl]-acetamide,
  2,N-dicyclohexyl-2-[2-(5-phenyl-thiophen-2-yl)-benzoimidazol-1-yl]-acetamide,
  3-{1-[cyclohexyl-(cyclohexylcarbamoyl-methyl)]-1H-benzoimidazol-2-yl}-benzoic acid methyl ester,
  and any pharmaceutically acceptable salt or ester thereof.

26. A compound of claim 1, selected from the group consisting of:
  2-[2-(3-hydroxy-phenyl)-benzoimidazol-1-yl]-4-methyl-pentanoic acid cyclohexylamide,
  2-[2-(4-hydroxymethyl-phenyl)-benzoimidazol-1-yl]-4-methyl-pentanoic acid cyclohexylamide,
  2-[2-(1H-indol-5-yl)-benzoimidazol-1-yl]-4-methyl-pentanoic acid cyclohexylamide,
  2-[2-(1H-indol-6-yl)-benzoimidazol-1-yl]-4-methyl-pentanoic acid cyclohexylamide,
  2-[2-(4-amino-phenyl)-benzoimidazol-1-yl]-4-methyl-pentanoic acid cyclohexylamide,
  2,N-dicyclohexyl-2-[2-(4-hydroxymethyl-phenyl)-benzoimidazol-1-yl]-acetamide,
  N-cyclohexyl-2-[2-(2,3-dimethoxy-phenyl)-benzoimidazol-1-yl]-4-phenyl-butyramide,
  2-[2-(3-cyano-phenyl)-benzoimidazol-1-yl]-2,N-dicyclohexyl-acetamide,
  2,N-dicyclohexyl-2-{2-[4-(1H-tetrazol-5-yl)-phenyl]-benzoimidazol-1-yl}-acetamide hydrogen chloride,
  and any pharmaceutically acceptable salt or ester thereof.

27. A compound of claim 1, selected from the group consisting of:
  2-[2-(2,4-dimethoxy-phenyl)-benzoimidazol-1-yl]-hexanoic acid cyclohexylamide,
  2,N-dicyclohexyl-2-[2-(3-methanesulfonyl-phenyl)-benzoimidazol-1-yl]-acetamide hydrogen chloride,
  N-cyclopentyl-2-[2-(3-methoxy-phenyl)-benzoimidazol-1-yl]-4-phenyl-butyramide hydrogen chloride,
  2,N-dicyclohexyl-2-[2-(2,4-dimethoxy-phenyl)-5-methyl-benzoimidazol-1-yl]-acetamide hydrogen chloride,
  2-[2-(4-chloro-phenyl)-benzoimidazol-1-yl]-2,N-dicyclopentyl-acetamide hydrogen chloride,
  2-[2-(2,4-dimethoxy-phenyl)-benzoimidazol-1-yl]-4-methyl-pentanoic acid cyclohexylamide,
  2-[2-(4-Acetyl-phenyl)-benzoimidazol-1-yl]-N-cyclohexyl-4-phenyl-butyramide,
  N-cyclopentyl-2-[2-(3-hydroxy-phenyl)-benzoimidazol-1-yl]-4-phenyl-butyramide,
  2-[2-(4-acetyl-phenyl)-benzoimidazol-1-yl]-4-methyl-pentanoic acid cyclohexylamide,
  2-[2-(3-cyano-phenyl)-benzoimidazol-1-yl]-4-methyl-pentanoic acid cyclohexylamide,
  and any pharmaceutically acceptable salt or ester thereof.

28. A compound of claim 1, selected from the group consisting of:
  2,N-dicyclohexyl-2-[2-(2,4-dimethoxy-phenyl)-4-methyl-benzoimidazol-1-yl]-acetamide,
  2,N-dicyclohexyl-2-{2-[3-(2-oxo-pyrrolidin-1-yl)-phenyl]-benzoimidazol-1-yl}-acetamide hydrogen chloride,
  2,N-dicyclohexyl-2-[2-(2-oxo-1,2-dihydro-pyridin-4-yl)-benzoimidazol-1-yl]-acetamide,
  N-cyclopentyl-2-[2-(2-methoxy-phenyl)-benzoimidazol-1-yl]-4-phenyl-butyramide,
  2,N-dicyclopentyl-2-(2-naphthalene-1-yl-benzoimidazol-1-yl)-acetamide,
  2-[2-(3-cyano-phenyl)-benzoimidazol-1-yl]-N-cyclohexyl-4-phenyl-butyramide,
  2-[2-(3-chloro-phenyl)-benzoimidazol-1-yl]-4-methyl-pentanoic acid cyclohexylamide,
  2-[2-(4-hydroxy-phenyl)-benzoimidazol-1-yl]-4-methyl-pentanoic acid cyclohexylamide,
  2-[2-(4-Acetylamino-phenyl)-benzoimidazol-1-yl]-2,N-dicyclohexyl-acetamide, 2-[2-(3-acetylamino-phenyl)-benzoimidazol-1-yl]-2,N-dicyclohexyl-acetamide, and any pharmaceutically acceptable salt or ester thereof.

29. A compound of claim 1, selected from the group consisting of:
- 2-[2-(4-hydroxy-phenyl)-benzoimidazol-1-yl]-4-methyl-pentanoic acid cyclohexylamide hydrogen chloride,
- 4-[1-(1-cyclohexylcarbamoyl-3-phenyl-propyl)-1H-benzoimidazol-2-yl]-benzoic acid methyl ester,
- 2,N-dicyclopentyl-2-[2-(2-methoxy-phenyl)-benzoimidazol-1-yl]-acetamide,
- 2,N-dicyclohexyl-2-[2-(2,4-dimethoxy-phenyl)-naphtho[2,3-d]imidazol-1-yl]-acetamide,
- 2-[2-(2,3-dimethoxy-phenyl)-benzoimidazol-1-yl]-4-methyl-pentanoic acid cyclohexylamide,
- 2-[2-(4-Chloro-phenyl)-benzoimidazol-1-yl]-N-cyclohexyl-2-(tetrahydro-pyran-4-yl)-acetamide,
- (S)-2-[2-(4-Chloro-phenyl)-5,6-difluoro-benzoimidazol-1-yl]-N-cyclohexyl-2-(tetrahydro-pyran-4-yl)-acetamide,
- 2-[2-(4-Chloro-phenyl)-5-fluoro-benzoimidazol-1-yl]-N-cyclohexyl-2-(tetrahydro-pyran-4-yl)-acetamide,
- 2-[2-(4-Chloro-phenyl)-6-fluoro-benzoimidazol-1-yl]-N-cyclohexyl-2-(tetrahydro-pyran-4-yl)-acetamide, and any pharmaceutically acceptable salt or ester thereof.

30. A compound of claim 9, selected from the group consisting of:
- N-benzyl-2-cyclopentyl-2-(2-naphthalen-1-yl-benzoimidazol-1-yl)-acetamide,
- 2,N-dicyclohexyl-2-[2-(2,3-dimethoxy-phenyl)-benzoimidazol-1-yl]-acetamide,
- 2-cyclohexyl-2-[2-(2,3-dimethoxy-phenyl)-benzoimidazol-1-yl]-N-isopropyl-acetamide,
- 2-[2-(2,3-dimethoxy-phenyl)-benzoimidazol-1-yl]-N-isopropyl-4-phenyl-butyramide,
- N-benzyl-2-[2-(4-chloro-phenyl)-benzoimidazol-1-yl]-4-phenyl-butyramide hydrogen chloride,
- N-butyl-2-[2-(2,4-dimethoxy-phenyl)-benzoimidazol-1-yl]-2-phenyl-acetamide,
- 4-{1-[cyclohexyl-(4-morpholin-4-yl-phenylcarbamoyl)-methyl]-1H-benzoimidazol-2-yl}-benzoic acid methyl ester hydrochloride,
- 2-cyclohexyl-2-[2-(2,4-dimethoxy-phenyl)-benzoimidazol-1-yl]-N-isopropyl-acetamide hydrogen chloride,
- 2-cyclohexyl-2-[2-(2,4-dimethoxy-phenyl)-benzoimidazol-1-yl]-N-((R) 1-phenyl-ethyl)-acetamide,
- 3-[1-(benzylcarbamoyl-cyclopentyl-methyl)-1H-benzoimidazol-2-yl]-benzoic acid methyl ester,
- N-benzyl-2-cyclohexyl-2-[2-(2,4-dimethoxy-phenyl)-benzoimidazol-1-yl]-acetamide,
- 2-cyclohexyl-2-[2-(2,4-dimethoxy-phenyl)-benzoimidazol-1-yl]-N-(1-methyl-butyl)-acetamide,
- 4-[1-(benzylcarbamoyl-cyclopentyl-methyl)-1H-benzoimidazol-2-yl]-benzoic acid methyl ester,
- N-benzhydryl-2-cyclohexyl-2-[2-(2,4-dimethoxy-phenyl)-enzoimidazol-1-yl]-acetamide, and any pharmaceutically acceptable salt or ester thereof.

31. A compound of claim 14, selected from the group consisting of:
- 2-benzo[1,3]dioxol-5-yl-N-butyl-2-[2-(2,3-dimethoxy-phenyl)-benzoimidazol-1-yl]-acetamide,
- 2-benzo[1,3]dioxol-5-yl-N-butyl-2-[2-(2,4-dimethoxy-phenyl)-benzoimidazol-1-yl]-acetamide,
- N-butyl-2-[2-(2,4-dimethoxy-phenyl)-benzoimidazol-1-yl]-2-(2-fluoro-phenyl)-acetamide,
- 2-[2-(4-acetyl-phenyl)-benzoimidazol-1-yl]-hexanoic acid isopropylamide,
- N-butyl-2-[2-(2,3-dimethoxy-phenyl)-benzoimidazol-1-yl]-2-o-tolyl-acetamide,
- N-butyl-2-[2-(2,3-dimethoxy-phenyl)-benzoimidazol-1-yl]-2-(4-methoxy-phenyl)-acetamide,
- N-butyl-2-[2-(2,3-dimethoxy-phenyl)-benzoimidazol-1-yl]-2-(2-fluoro-phenyl)-acetamide,
- N-cyclopentyl-2-(2-naphthalen-1-yl-benzoimidazol-1-yl)-propionamide, and any pharmaceutically acceptable salt or ester thereof.

32. A compound of claim 14, selected from the group consisting of:
- N-butyl-2-[2-(2,3-dimethoxy-phenyl)-benzoimidazol-1-yl]-2-(4-dimethylamino-phenyl)-acetamide,
- 2-[2-(2,3-dimethoxy-phenyl)-benzoimidazol-1-yl]-hexanoic acid isopropylamide,
- 4-{1-[(2-fluoro-phenyl)-isopropylcarbamoyl-methyl]-1H-benzoimidazol-2-yl}-benzoic acid methyl ester,
- N-butyl-2-[2-(2,4-dimethoxy-phenyl)-benzoimidazol-1-yl]-2-(4-methoxy-phenyl)-acetamide,
- N-benzyl-2-[2-(3-methoxy-phenyl)-benzoimidazol-1-yl]-4-phenyl-butyramide hydrogen chloride,
- 2-(4-chloro-phenyl)-2-[2-(2,3-dimethoxy-phenyl)-benzoimidazol-1-yl]-N-isopropyl-acetamide,
- N-butyl-2-[2-(2,4-dimethoxy-phenyl)-benzoimidazol-1-yl]-2-(4-dimethylamino-phenyl)-acetamide,
- 2-[2-(4-hydroxy-phenyl)-benzoimidazol-1-yl]-N-isopropyl-4-phenyl-butyramide, and any pharmaceutically acceptable salt or ester thereof.

33. A compound of claim 14, selected from the group consisting of:
- N-butyl-2-(4-chloro-phenyl)-2-[2-(2,4-dimethoxy-phenyl)-benzoimidazol-1-yl]-acetamide,
- 2-[2-(3-cyano-phenyl)-benzoimidazol-1-yl]-N-isopropyl-4-phenyl-butyramide,
- 2-[2-(4-acetyl-phenyl)-benzoimidazol-1-yl]-N-isopropyl-2-(4-methoxy-phenyl)acetamide,
- 4-{1-[isopropylcarbamoyl-(4-methoxy-phenyl)-methyl]-1H-benzoimidazol-2-yl}-benzoic acid methyl ester,
- 4-[1-(isopropylcarbamoyl-phenyl-methyl)-1H-benzoimidazol-2-yl]-benzoic acid methyl ester,
- 2-[2-(3-cyano-phenyl)-benzoimidazol-1-yl]-hexanoic acid isopropylamide,
- 2-[2-(4-hydroxy-phenyl)-benzoimidazol-1-yl]-pentanoic acid isopropylamide,
- 4-[1-(1-isopropylcarbamoyl-pentyl)-1H-benzoimidazol-2-yl]-benzoic acid methyl ester,
- 2-[2-(2,3-dimethoxy-phenyl)-benzoimidazol-1-yl]-4-methyl-pentanoic acid isopropylamide,
- 2-benzo[1,3]dioxol-5-yl-N-butyl-2-[2-(1-methyl-1H-pyrrol-2-yl)-benzoimidazol-1-yl]-acetamide, and any pharmaceutically acceptable salt or ester thereof.

34. A compound of claim 1, selected from the group consisting of:
- 2,N-dicyclohexyl-2-[2-(2,4-dimethoxy-phenyl)-benzoimidazol-1-yl]-acetamide,
- 2-cyclohex-3-enyl-N-cyclohexyl-2-[2-(2,4-dimethoxy-phenyl)-benzoimidazol-1-yl]-acetamide,
- 2-[2-(4-cyano-phenyl)-benzoimidazol-1-yl]-2,N-dicyclohexyl-acetamide hydrogen chloride,
- 2-cyclohexyl-N-cyclopentyl-2-[2-(2,4-dimethoxy-phenyl)-benzoimidazol-1-yl]-acetamide,
- 2,N-dicyclohexyl-2-[2-(2,4-dimethoxy-phenyl)-5,6-difluoro-benzoimidazol-1-yl]-acetamide,
- 2,N-dicyclohexyl-2-[2-(2,4-dimethoxy-phenyl)-6-methyl-benzoimidazol-1-yl]-acetamide,
- 2-[2-(4-chloro-phenyl)-benzoimidazol-1-yl]-2,N-dicyclohexyl-acetamide, 2,N-dicyclohexyl-2-[2-(4-sulfamoyl-phenyl)-benzoimi-
dazol-1-yl]-acetamide hydrogen chloride,
and any pharmaceutically acceptable salt or ester thereof.

35. A compound of claim 1, selected from the group consisting of:
4-{[1-cyclopentyl-(cyclopentylcarbamoyl-methyl)]-1H-
benzoimidazol-2-yl}-benzoic acid methyl ester hydrogen chloride,
2,N-dicyclohexyl-2-(2-quinolin-6-yl-benzoimidazol-1-
yl)-acetamide hydrogen chloride,
2-[2-(4-amino-phenyl)-benzoimidazol-1-yl]-2,N-dicyclohexyl-acetamide,
2-[2-(2,4-dimethoxy-phenyl)-benzoimidazol-1-yl]-5-phenyl-pentanoic acid cyclohexylamide hydrogen chloride,
4-[1-(1-cyclopentylcarbamoyl-3-phenyl-propyl)-1H-benzoimidazol-2-yl]-benzoic acid methyl ester,
2,N-dicyclohexyl-2-[2-(4-dimethylsulfamoyl-phenyl)-
benzoimidazol-1-yl]-acetamide hydrogen chloride,
2,N-dicyclohexyl-2-[2-(3-sulfamoyl-phenyl)-benzoimi-
dazol-1-yl]-acetamide hydrogen chloride,
2,N-dicyclohexyl-2-{2-[3-(1H-tetrazol-5-yl)-phenyl]-
benzoimidazol-1-yl}-acetamide hydrogen chloride,
and any pharmaceutically acceptable salt or ester thereof.

36. A compound of claim 1, selected from the group consisting of:
2,N-dicyclohexyl-2-{2-[4-(1H-imidazol-2-yl)-phenyl]-
benzoimidazol-1-yl}-acetamide hydrogen chloride,
2,N-dicyclohexyl-2-[2-(4-imidazol-1-yl-phenyl)-ben-
zoimidazol-1-yl]-acetamide hydrogen chloride,
2,N-dicyclohexyl-2-[2-(4-[1,2,4]triazol-4-yl-phenyl)-
benzoimidazol-1-yl]-acetamide hydrogen chloride,
2,N-dicyclohexyl-2-{2-[4-(1H-pyrazol-4-yl)-phenyl]-
benzoimidazol-1-yl}-acetamide hydrogen chloride,
2,N-dicyclohexyl-2-[2-(4-[1,2,3]thiadiazol-4-yl-phenyl)-
benzoimidazol-1-yl]-acetamide hydrogen chloride,
2,N-dicyclohexyl-2-[2-(1,3-dioxo-2,3-dihydro-1H-isoin-
dol-5-yl)-benzoimidazol-1-yl]-acetamide hydrogen chloride,
2,N-dicyclohexyl-2-[2-(3-tetrazol-1-yl-phenyl)-ben-
zoimidazol-1-yl]-acetamide hydrogen chloride,
and any pharmaceutically acceptable salt or ester thereof.

37. A compound of claim 9, selected from the group consisting of:
N-cyclohexyl-2-[2-(2,4-dimethoxy-phenyl)-benzoimida-
zol-1-yl]-2-phenyl-acetamide hydrogen chloride,
4-(1-{cyclohexyl-[3-(2-oxo-pyrrolidin-1-yl)-propylcar-
bamoyl]-methyl}-1H -benzoimidazol-2-yl)-benzoic
acid methyl ester hydrogen chloride,
4-{1-[cyclohexyl-(3-methoxycarbonyl-propylcarbam-
oyl)-methyl]-1H-benzoimidazol-2-yl}-benzoic acid
methyl ester hydrogen chloride,
4-{1-[cyclohexyl-(4-methoxycarbonyl-butylcarbamoyl)-
methyl]-1H-benzoimidazol-2-yl}-benzoic acid methyl
ester hydrogen chloride,
4-{1-[cyclohexyl-(5-methoxycarbonyl-pentylcarbam-
oyl)-methyl]-1H-benzoimidazol-2-yl}-benzoic acid
methyl ester hydrogen chloride,
2-cyclohexyl-2-[2-(2,4-dimethoxy-phenyl)-benzoimida-
zol-1-yl]-N-methyl-acetamide hydrogen chloride,
N-benzyl-2-(2-naphthalen-1-yl-benzoimidazol-1-yl)-4-
phenyl-butyramide,
2-cyclohexyl-2-[2-(2,4-dimethoxy-phenyl)-benzoimida-
zol-1-yl]-N-(4-methoxy-phenyl)-acetamide,
2-cyclohexyl-2-[2-(2,4-dimethoxy-phenyl)-benzoimida-
zol-1-yl]-N-pentyl-acetamide,
N-benzyl-2-[2-(4-chloro-phenyl)-benzoimidazol-1-yl]-2-
cyclopentyl-acetamide hydrogen chloride,
N-tert-butyl-2-cyclohexyl-2-[2-(2,4-dimethoxy-phenyl)-
benzoimidazol-1-yl]-acetamide,
4-[1-(1-benzylcarbamoyl-3-phenyl-propyl)-1H-ben-
zoimidazol-2-yl]-benzoic acid methyl ester,
N-benzyl-2-[2-(2-methoxy-phenyl)-benzoimidazol-1-yl]-
4-phenyl-butyramide,
2-cyclohexyl-2-[2-(2,4-dimethoxy-phenyl)-benzoimida-
zol-1-yl]-N-(3-isopropoxy-propyl)-acetamide,
and any pharmaceutically acceptable salt or ester thereof.

38. A compound of claim 1, selected from the group consisting of:
N-cyclohexyl-2-[2-(2,4-dimethoxy-phenyl)-benzoimida-
zol-1-yl]-2-pyridin-2-yl-acetamide hydrogen chloride,
N-cyclohexyl-2-cyclopentyl-2-[2-(2,4-dimethoxy-phe-
nyl)-benzoimidazol-1-yl]-acetamide hydrogen chloride,
2,N-dicyclohexyl-2-(2-naphthalen-2-yl-benzoimidazol-1-
yl)-acetamide,
2,N-dicyclohexyl-2-[2-(5-phenyl-thiophen-2-yl)-ben-
zoimidazol-1-yl]-acetamide,
2,N-dicyclohexyl-2-[2-(4-hydroxymethyl-phenyl)-ben-
zoimidazol-1-yl]-acetamide,
2,N-dicyclohexyl-2-{2-[4-(1H-tetrazol-5-yl)-phenyl]-
benzoimidazol-1-yl}-acetamide hydrogen chloride,
2,N-dicyclohexyl-2-[2-(2,4-dimethoxy-phenyl)-5-me-
thyl-benzoimidazol-1-yl]-acetamide hydrogen chloride,
2,N-dicyclohexyl-2-[2-(2-oxo-1,2-dihydro-pyridin-4-yl)-
benzoimidazol-1-yl]-acetamide,
and any pharmaceutically acceptable salt or ester thereof.

39. A compound of claim 1, selected from the group consisting of:
2-cyclohexyl-N-cyclopentyl-2-[2-(2,4-dimethoxy-phe-
nyl)-benzoimidazol-1-yl]-acetamide,
2,N-dicyclohexyl-2-(2-quinolin-6-yl-benzoimidazol-1-
yl)-acetamide hydrogen chloride,
2-[2-(2,4-dimethoxy-phenyl)-benzoimidazol-1-yl]-5-phe-
nyl-pentanoic acid cyclohexylamide hydrogen chloride,
2,N-dicyclohexyl-2-{2-[4-(1H-imidazol-2-yl)-phenyl]-
benzoimidazol-1-yl}-acetamide hydrogen chloride,
N-cyclohexyl-2-[2-(2,4-dimethoxy-phenyl)-benzoimida-
zol-1-yl]-2-phenyl-acetamide hydrogen chloride,
2-[2-(4-Acetylamino-phenyl)-benzoimidazol-1-yl]-2,N-
dicyclohexyl-acetamide,
and any pharmaceutically acceptable salt or ester thereof.

40. A compound of claim 1, selected from the group consisting of:
2,N-Dicyclohexyl-2-(2-phenyl-benzoimidazol-1-yl)-ac-
etamide,
2-[1-(Cyclohexyl-cyclohexylcarbamoyl-methyl)-1H-ben-
zoimidazol-2-yl]-benzamide,
2-[2-(5-Amino-pyridin-2-yl)-benzoimidazol-1-yl]-2,N-
dicyclohexyl-acetamide,
2,N-Dicyclohexyl-2-[2-(2-ethyl-5-methyl-2H-pyrazol-3-
yl)-benzoimidazol-1-yl]-acetamide,
2,N-Dicyclohexyl-2-[2-(5-methyl-isoxazol-4-yl)-ben-
zoimidazol-1-yl]-acetamide,
2,N-Dicyclohexyl-2-[2-(1H-pyrrol-2-yl)-benzoimidazol-
1-yl]-acetamide,
2-(1'H-[2,5']Bibenzoimidazolyl-1-yl)-2,N-dicyclohexyl-
acetamide,
2,N-Dicyclohexyl-2-(2-furan-2-yl-benzoimidazol-1-yl)-
acetamide,
2-[6-Bromo-2-(4-chloro-phenyl)-benzoimidazol-1-yl]-2,
N-dicyclohexyl-acetamide,
2-[6-Chloro-2-(4-chloro-phenyl)-benzoimidazol-1-yl]-2,
N-dicyclohexyl-acetamide,
and any pharmaceutically acceptable salt or ester thereof.

41. A compound of claim 1, selected from the group consisting of:
- 2-[2-(4-Chloro-phenyl)-6-methoxy-benzoimidazol-1-yl]-2,N-dicyclohexyl-acetamide,
- 2-[6-Chloro-2-(4-chloro-phenyl)-5-fluoro-benzoimidazol-1-yl]-2,N-dicyclohexyl-acetamide,
- (S)-2,N-Dicyclohexyl-2-[2-(2,4-dimethoxy-phenyl)-benzoimidazol-1-yl]-acetamide,
- (S)-2-[2-(4-Chloro-phenyl)-benzoimidazol-1-yl]-2,N-dicyclohexyl-acetamide,
- 2-[1-(Cyclohexyl-cyclohexyl-carbamoyl-methyl)-1H-benzoimidazol-2-yl]-N-methyl-benzamide,
- 2,N-Dicyclohexyl-2-(2-furan-3-yl-benzoimidazol-1-yl)-acetamide,
- 2,N-Dicyclohexyl-2-[2-(3-methyl-furan-2-yl)-benzoimidazol-1-yl]-acetamide,
- 2,N-Dicyclohexyl-2-[2-(3-methyl-isoxazol-5-yl)-benzoimidazol-1-yl]-acetamide,
- 2,N-Dicyclohexyl-2-(2-m-tolyl-benzoimidazol-1-yl)-acetamide,
- 2,N-Dicyclohexyl-2-[2-(3-fluoro-phenyl)-benzoimidazol-1-yl]-acetamide, and any pharmaceutically acceptable salt or ester thereof.

42. A compound of claim 1, selected from the group consisting of:
- 2,N-Dicyclohexyl-2-[2-(2-fluoro-phenyl)-benzoimidazol-1-yl]-acetamide,
- 2,N-Dicyclohexyl-2-[2-(3,5-dimethyl-isoxazol-4-yl)-benzoimidazol-1-yl]-acetamide,
- 2,N-Dicyclohexyl-2-[2-(3-methyl-thiophen-2-yl)-benzoimidazol-1-yl]-acetamide,
- 2,N-Dicyclohexyl-2-[2-(4-vinyl-phenyl)-benzoimidazol-1-yl]-acetamide,
- 2,N-Dicyclohexyl-2-[2-(2,3-dimethyl-phenyl)-benzoimidazol-1-yl]-acetamide,
- 2,N-Dicyclohexyl-2-[2-(3,4-dimethyl-phenyl)-benzoimidazol-1-yl]-acetamide,
- 2,N-Dicyclohexyl-2-[2-(4-ethyl-phenyl)-benzoimidazol-1-yl]-acetamide,
- 2,N-Dicyclohexyl-2-[2-(2,4-dimethyl-phenyl)-benzoimidazol-1-yl]-acetamide,
- 2,N-Dicyclohexyl-2-[2-(2-ethyl-phenyl)-benzoimidazol-1-yl]-acetamide,
- 2,N-Dicyclohexyl-2-[2-(4-fluoro-3-methyl-phenyl)-benzoimidazol-1-yl]-acetamide, and any pharmaceutically acceptable salt or ester thereof.

43. A compound of claim 1, selected from the group consisting of:
- 2,N-Dicyclohexyl-2-[2-(3-fluoro-4-methyl-phenyl)-benzoimidazol-1-yl]-acetamide,
- 2,N-Dicyclohexyl-2-[2-(2,6-difluoro-phenyl)-benzoimidazol-1-yl]-acetamide,
- 2,N-Dicyclohexyl-2-[2-(3,5-difluoro-phenyl)-benzoimidazol-1-yl]-acetamide,
- 2,N-Dicyclohexyl-2-[2-(2,5-difluoro-phenyl)-benzoimidazol-1-yl]-acetamide,
- 2,N-Dicyclohexyl-2-[2-(3,4-difluoro-phenyl)-benzoimidazol-1-yl]-acetamide,
- 2,N-Dicyclohexyl-2-[2-(2,3-difluoro-phenyl)-benzoimidazol-1-yl]-acetamide,
- 2,N-Dicyclohexyl-2-[2-(1H-indol-4-yl)-benzoimidazol-1-yl]-acetamide,
- 2,N-Dicyclohexyl-2-[2-(1H-indol-6-yl)-benzoimidazol-1-yl]-acetamide,
- 2-[2-(5-Chloro-thiophen-2-yl)-benzoimidazol-1-yl]-2,N-dicyclohexyl-acetamide,
- 2-[2-(4-Acetyl-phenyl)-benzoimidazol-1-yl]-2,N-dicyclohexyl-acetamide, and any pharmaceutically acceptable salt or ester thereof.

44. A compound of claim 1, selected from the group consisting of:
- 2-[2-(2-Acetyl-phenyl)-benzoimidazol-1-yl]-2,N-dicyclohexyl-acetamide,
- 2,N-Dicyclohexyl-2-[2-(4-isopropyl-phenyl)-benzoimidazol-1-yl]-acetamide,
- 2-[2-(4-Cyano-2-fluoro-phenyl)-benzoimidazol-1-yl]-2,N-dicyclohexyl-acetamide,
- 2,N-Dicyclohexyl-2-[2-(2-dimethylamino-phenyl)-benzoimidazol-1-yl]-acetamide,
- 2,N-Dicyclohexyl-2-[2-(3-dimethylamino-phenyl)-benzoimidazol-1-yl]-acetamide,
- 2,N-Dicyclohexyl-2-[2-(4-methoxy-3-methyl-phenyl)-benzoimidazol-1-yl]-acetamide,
- 2,N-Dicyclohexyl-2-[2-(4-methoxy-2-methyl-phenyl)-benzoimidazol-1-yl]-acetamide,
- 2,N-Dicyclohexyl-2-[2-(3-methoxy-4-methyl-phenyl)-benzoimidazol-1-yl]-acetamide,
- 2,N-Dicyclohexyl-2-[2-(2-ethoxy-phenyl)-benzoimidazol-1-yl]-acetamide,
- 2-[2-(6-Chloro-pyridin-3-yl)-benzoimidazol-1-yl]-2,N-dicyclohexyl-acetamide, and any pharmaceutically acceptable salt or ester thereof.

45. A compound of claim 1, selected from the group consisting of:
- 2-[2-(2-Chloro-pyridin-4-yl)-benzoimidazol-1-yl]-2,N-dicyclohexyl-acetamide,
- 2-[2-(4-Chloro-phenyl)-6-fluoro-benzoimidazol-1-yl]-2,N-dicyclohexyl-acetamide,
- 2,N-Dicyclohexyl-2-[2-(3-fluoro-4-methoxy-phenyl)-benzoimidazol-1-yl]-acetamide,
- 2-[2-(4-Chloro-3-methyl-phenyl)-benzoimidazol-1-yl]-2,N-dicyclohexyl-acetamide,
- 2-[2-(3-Chloro-2-methyl-phenyl)-benzoimidazol-1-yl]-2,N-dicyclohexyl-acetamide,
- 2-[2-(4-Chloro-3-fluoro-phenyl)-benzoimidazol-1-yl]-2,N-dicyclohexyl-acetamide,
- 2-[2-(3-Chloro-4-fluoro-phenyl)-benzoimidazol-1-yl]-2,N-dicyclohexyl-acetamide,
- 2,N-Dicyclohexyl-2-[2-(5-methyl-1H-indol-2-yl)-benzoimidazol-1-yl]-acetamide,
- 2,N-Dicyclohexyl-2-[2-(2,3,4-trifluoro-phenyl)-benzoimidazol-1-yl]-acetamide,
- 2,N-Dicyclohexyl-2-[2-(2,4,5-trifluoro-phenyl)-benzoimidazol-1-yl]-acetamide, and any pharmaceutically acceptable salt or ester thereof.

46. A compound of claim 1, selected from the group consisting of:
- 2-(2-Benzo[b]thiophen-2-yl-benzoimidazol-1-yl)-2,N-dicyclohexyl-acetamide,
- 2,N-Dicyclohexyl-2-[2-(5-fluoro-1H-indol-2-yl)-benzoimidazol-1-yl]-acetamide,
- 2-(2-Benzothiazol-6-yl-benzoimidazol-1-yl)-2,N-dicyclohexyl-acetamide,
- 2,N-Dicyclohexyl-2-[2-(4-isopropoxy-phenyl)-benzoimidazol-1-yl]-acetamide,
- 2,N-Dicyclohexyl-2-[2-(3,4-dimethoxy-phenyl)-benzoimidazol-1-yl]-acetamide,
- 2,N-Dicyclohexyl-2-[2-(2,5-dimethoxy-phenyl)-benzoimidazol-1-yl]-acetamide,
- 2,N-Dicyclohexyl-2-[2-(2-difluoromethoxy-phenyl)-benzoimidazol-1-yl]-acetamide,
- 2,N-Dicyclohexyl-2-[2-(4-difluoromethoxy-phenyl)-benzoimidazol-1-yl]-acetamide, 2,N-Dicyclohexyl-2-[2-(3-difluoromethoxy-phenyl)-benzoimidazol-1-yl]-acetamide,
2,N-Dicyclohexyl-2-[2-(4-trifluoromethyl-phenyl)-benzoimidazol-1-yl]-acetamide,
and any pharmaceutically acceptable salt or ester thereof.

47. A compound of claim 1, selected from the group consisting of:
2,N-Dicyclohexyl-2-[2-(3,4-dichloro-phenyl)-benzoimidazol-1-yl]-acetamide,
2-[2-(4-Bromo-phenyl)-benzoimidazol-1-yl]-2,N-dicyclohexyl-acetamide,
2,N-Dicyclohexyl-2-[2-(6-methoxy-naphthalen-2-yl)-benzoimidazol-1-yl]-acetamide,
2,N-Dicyclohexyl-2-[2-(3-trifluoromethoxy-phenyl)-benzoimidazol-1-yl]-acetamide,
2,N-Dicyclohexyl-2-[2-(7-ethoxy-benzofuran-2-yl)-benzoimidazol-1-yl]-acetamide,
2,N-Dicyclohexyl-2-[2-(3-fluoro-4-trifluoromethyl-phenyl)-benzoimidazol-1-yl]-acetamide, 2,N-Dicyclohexyl-2-[2-(6-diethylamino-pyridin-3-yl)-benzoimidazol-1-yl]-acetamide,
2-[2-(2-Chloro-5-methyl-phenyl)-benzoimidazol-1-yl]-2,N-dicyclohexyl-acetamide,
2-[2-(5-Chloro-2-methyl-phenyl)-benzoimidazol-1-yl]-2,N-dicyclohexyl-acetamide,
2-[2-(2-Chloro-6-methyl-phenyl)-benzoimidazol-1-yl]-2,N-dicyclohexyl-acetamide,
and any pharmaceutically acceptable salt or ester thereof.

48. A compound of claim 1, selected from the group consisting of:
2,N-Dicyclohexyl-2-(2-quinoxalin-6-yl-benzoimidazol-1-yl)-acetamide,
2-[2-(5-Chloro-2-fluoro-phenyl)-benzoimidazol-1-yl]-2,N-dicyclohexyl-acetamide,
2,N-Dicyclohexyl-2-[2-(4-methoxy-3,5-dimethyl-phenyl)-benzoimidazol-1-yl]-acetamide,
2,N-Dicyclohexyl-2-[2-(2,3-dimethoxy-phenyl)-benzoimidazol-1-yl]-acetamide,
2-[2-(3-Chloro-4-methoxy-phenyl)-benzoimidazol-1-yl]-2,N-dicyclohexyl-acetamide,
2,N-Dicyclohexyl-2-[2-(2,5-dichloro-phenyl)-benzoimidazol-1-yl]-acetamide,
2-[2-(3-Chloro-2,4-difluoro-phenyl)-benzoimidazol-1-yl]-2,N-dicyclohexyl-acetamide,
2-[2-(2-Chloro-4,5-difluoro-phenyl)-benzoimidazol-1-yl]-2,N-dicyclohexyl-acetamide,
2,N-Dicyclohexyl-2-[2-(4-diethylamino-phenyl)-benzoimidazol-1-yl]-acetamide,
2-[2-(4-Benzoyl-phenyl)-benzoimidazol-1-yl]-2,N-dicyclohexyl-acetamide,
and any pharmaceutically acceptable salt or ester thereof.

49. A compound of claim 1, selected from the group consisting of:
(S)-2-[2-(4-Cyano-phenyl)-benzoimidazol-1-yl]-2,N-dicyclohexyl-acetamide,
2,N-Dicyclohexyl-2-[2-(4-phenoxy-phenyl)-benzoimidazol-1-yl]-acetamide,
2,N-Dicyclohexyl-2-[2-(2-phenoxy-phenyl)-benzoimidazol-1-yl]-acetamide,
2,N-Dicyclohexyl-2-[2-(3-phenoxy-phenyl)-benzoimidazol-1-yl]-acetamide,
2,N-Dicyclohexyl-2-{2-[2-(1,1,2,2-tetrafluoro-ethoxy)-phenyl]-benzoimidazol-1-yl}-acetamide,
2,N-Dicyclohexyl-2-{2-[3-(1,1,2,2-tetrafluoro-ethoxy)-phenyl]-benzoimidazol-1-yl}-acetamide,
2,N-Dicyclohexyl-2-{2-[4-(1,1,2,2-tetrafluoro-ethoxy)-phenyl]-benzoimidazol-1-yl}-acetamide,
2,N-Dicyclohexyl-2-[2-(4'-trifluoromethyl-biphenyl-4-yl)-benzoimidazol-1-yl]-acetamide,
2,N-Dicyclohexyl-2-[2-(3',4'-dichloro-biphenyl-4-yl)-benzoimidazol-1-yl]-acetamide,
2,N-Dicyclohexyl-2-[2-(2,4-dichloro-5-sulfamoyl-phenyl)-benzoimidazol-1-yl]-acetamide,
and any pharmaceutically acceptable salt or ester thereof.

50. A compound of claim 1, selected from the group consisting of:
(S)-2-[6-Chloro-2-(4-chloro-phenyl)-5-fluoro-benzoimidazol-1-yl]-2,N-dicyclohexyl-acetamide,
2,N-Dicyclohexyl-2-(2-pyridin-2-yl-benzoimidazol-1-yl)-acetamide,
2,N-Dicyclohexyl-2-[2-(6-methyl-pyridin-3-yl)-benzoimidazol-1-yl]-acetamide,
2,N-Dicyclohexyl-2-[2-(3-methyl-pyridin-2-yl)-benzoimidazol-1-yl]-acetamide,
2,N-Dicyclohexyl-2-[2-(6-methyl-pyridin-2-yl)-benzoimidazol-1-yl]-acetamide,
2-[2-(2-Amino-pyridin-3-yl)-benzoimidazol-1-yl]-2,N-dicyclohexyl-acetamide,
2-[2-(6-Cyano-pyridin-3-yl)-benzoimidazol-1-yl]-2,N-dicyclohexyl-acetamide,
2,N-Dicyclohexyl-2-[2-(2-methoxy-pyridin-3-yl)-benzoimidazol-1-yl]-acetamide,
2-[2-(2-Chloro-6-methyl-pyridin-3-yl)-benzoimidazol-1-yl]-2,N-dicyclohexyl-acetamide,
2-[2-(2-Chloro-6-methyl-pyridin-4-yl)-benzoimidazol-1-yl]-2,N-dicyclohexyl-acetamide,
and any pharmaceutically acceptable salt or ester thereof.

51. A compound of claim 1, selected from the group consisting of:
2,N-Dicyclohexyl-2-(2-quinolin-3-yl-benzoimidazol-1-yl)-acetamide,
2,N-Dicyclohexyl-2-(2-quinolin-4-yl-benzoimidazol-1-yl)-acetamide,
2-[2-(3-Chloro-4-trifluoromethyl-phenyl)-benzoimidazol-1-yl]-2,N-dicyclohexyl-acetamide,
(S)-2-[2-(4-Chloro-phenyl)-benzoimidazol-1-yl]-4-methyl-pentanoic acid cyclohexylamide,
2-(4-Chloro-phenyl)-2-[2-(4-chloro-phenyl)-benzoimidazol-1-yl]-N-cyclohexyl-acetamide,
2-[2-(4-Chloro-phenyl)-benzoimidazol-1-yl]-N-cyclohexyl-2-(4-trifluoromethyl-phenyl)-acetamide,
2-[2-(4-Chloro-phenyl)-benzoimidazol-1-yl]-N-cyclohexyl-2-(3,4-dichloro-phenyl)-acetamide,
2-[2-(4-Chloro-phenyl)-benzoimidazol-1-yl]-N-cyclohexyl-2-(3-methoxy-phenyl)-acetamide,
2-[2-(4-Chloro-phenyl)-benzoimidazol-1-yl]-N-cyclohexyl-2-p-tolyl-acetamide,
2-[2-(4-Chloro-phenyl)-benzoimidazol-1-yl]-N-cyclohexyl-2-(3-fluoro-phenyl)-acetamide,
and any pharmaceutically acceptable salt or ester thereof.

52. A compound of claim 1, selected from the group consisting of:
2-[2-(4-Chloro-phenyl)-benzoimidazol-1-yl]-N-cyclohexyl-2-(4-difluoromethoxy-phenyl)-acetamide,
2-[2-(4-Chloro-phenyl)-benzoimidazol-1-yl]-N-cyclohexyl-2-(2,5-difluoro-phenyl)-acetamide,
2-[2-(4-Chloro-phenyl)-benzoimidazol-1-yl]-N-cyclohexyl-2-(2-fluoro-5-methoxy-phenyl)-acetamide,
(S)-2-[2-(5-Chloro-2-fluoro-phenyl)-benzoimidazol-1-yl]-2,N-dicyclohexyl-acetamide,
(S)-2,N-Dicyclohexyl-2-[2-(2,3-dimethoxy-phenyl)-benzoimidazol-1-yl]-acetamide,
(S)-2-[2-(3-Chloro-4-methoxy-phenyl)-benzoimidazol-1-yl]-2,N-dicyclohexyl-acetamide, (S)-2-Cyclohexyl-2-[2-(2,4-dimethoxy-phenyl)-benzoimidazol-1-yl]-N-(2,6-dimethyl-phenyl)-acetamide,
2-[2-(4-Chloro-phenyl)-benzoimidazol-1-yl]-2-cyclohexyl-N-(4,4-difluoro-cyclohexyl)-acetamide,
(S)-2-[2-(4-Chloro-phenyl)-benzoimidazol-1-yl]-2-cyclohexyl-N-(4,4-difluoro-cyclohexyl)-acetamide,
(S)-2-[2-(2-Amino-pyridin-3-yl)-benzoimidazol-1-yl]-2,N-dicyclohexyl-acetamide,
and any pharmaceutically acceptable salt or ester thereof.

53. A compound of claim 1, selected from the group consisting of:
2,N-Dicyclohexyl-2-(6-fluoro-2-pyridin-2-yl-benzoimidazol-1-yl)-acetamide,
2,N-Dicyclohexyl-2-[2-(2,4-dimethoxy-phenyl)-6-fluoro-benzoimidazol-1-yl]-acetamide,
2,N-Dicyclohexyl-2-[6-fluoro-2-(4-methoxy-phenyl)-benzoimidazol-1-yl]-acetamide,
2,N-Dicyclohexyl-2-[2-(2,3-difluoro-phenyl)-6-fluoro-benzoimidazol-1-yl]-acetamide,
2,N-Dicyclohexyl-2-[2-(2,3-dimethoxy-phenyl)-6-fluoro-benzoimidazol-1-yl]-acetamide,
2,N-Dicyclohexyl-2-[2-(2-ethyl-5-methyl-2H-pyrazol-3-yl)-6-fluoro-benzoimidazol-1-yl]-acetamide,
2,N-Dicyclohexyl-2-[2-(3,5-dimethyl-isoxazol-4-yl)-6-fluoro-benzoimidazol-1-yl]-acetamide,
2,N-Dicyclohexyl-2-[6-fluoro-2-(1H-pyrazol-4-yl)-benzoimidazol-1-yl]-acetamide,
2,N-Dicyclohexyl-2-[2-(1,5-dimethyl-1H-pyrazol-3-yl)-6-fluoro-benzoimidazol-1-yl]-acetamide,
2,N-Dicyclohexyl-2-[6-fluoro-2-(3-methyl-isoxazol-5-yl)-benzoimidazol-1-yl]-acetamide,
and any pharmaceutically acceptable salt or ester thereof.

54. A compound of claim 10, selected from the group consisting of:
2,N-Dicyclohexyl-2-[6-fluoro-2-(1H-pyrrol-2-yl)-benzoimidazol-1-yl]-acetamide,
2,N-Dicyclohexyl-2-[6-fluoro-2-(3-methyl-thiophen-2-yl)-benzoimidazol-1-yl]-acetamide,
N-Benzyl-2-[2-(4-chloro-phenyl)-benzoimidazol-1-yl]-2-cyclohexyl-acetamide,
N-Butyl-2-[2-(4-chloro-phenyl)-benzoimidazol-1-yl]-2-cyclohexyl-acetamide,
2-[5-Chloro-2-(4-chloro-phenyl)-6-fluoro-benzoimidazol-1-yl]-2,N-dicyclohexyl-acetamide,
2-[2-(4-Chloro-phenyl)-5,6-difluoro-benzoimidazol-1-yl]-2,N-dicyclohexyl-acetamide,
2-[2-(4-Chloro-phenyl)-benzoimidazol-1-yl]-2-cyclohexyl-N-(tetrahydro-pyran-4-yl)-acetamide,
2-[2-(4-Chloro-phenyl)-benzoimidazol-1-yl]-2-cyclohexyl-N-cyclopropyl-acetamide,
2,N-Dicyclohexyl-2-[2-(6-morpholin-4-yl-pyridin-3-yl)-benzoimidazol-1-yl]-acetamide,
2-[2-(2,4-dimethoxy-phenyl)-benzoimidazol-1-yl]-N-isopropyl-4-phenyl-butyramide,
N-butyl-2-[2-(2,3-dimethoxy-phenyl)-benzoimidazol-1-yl]-2-phenyl-acetamide,
2-[2-(3-chloro-phenyl)-benzoimidazol-1-yl]-N-isopropyl-4-phenyl-butyramide,
N-isopropyl-2-[2-(1-methyl-iH-pyrrol-2-yl)-benzoimidazol-1-yl]-4-phenyl-butyramide,
2-cyclohexyl-2-[2-(2,4-dimethoxy-phenyl)-benzoimidazol-1-yl]-N-(2,6-dimethyl-phenyl)-acetamide,
2-cyclohexyl-2-[2-(2,4-dimethoxy-phenyl)-benzoimidazol-1-yl]-N-(1,1,3,3-tetramethyl-butyl)-acetamide,
4-[1-(cyclohexyl-3-methoxycarbonylphenylcarbamoyl-methyl)-1H-benzoimidazol-2-yl]-benzoic acid methyl ester hydrogen chloride,
trans 4-(1-{cyclohexyl-[(4-methoxycarbonyl-cyclohexyl-methyl)-carbamoyl]-methyl}-1H-benzoimidazol-2-yl)-benzoic acid methyl ester hydrogen chloride,
and any pharmaceutically acceptable salt or ester thereof.

55. A compound of claim 1, selected from the group consisting of:
(S)-2,N-Dicyclohexyl-2-[2-(4-methanesulfonyl-phenyl)-benzoimidazol-1-yl]-acetamide,
(S)-2-[2-(4-Chloro-phenyl)-benzoimidazol-1-yl]-2-cyclohexyl-N-cyclopropyl-acetamide,
2-[6-Chloro-2-(4-chloro-phenyl)-5-fluoro-benzoimidazol-1-yl]-N-cyclohexyl-2-(tetrahydro-pyran-4-yl)-acetamide,
(S)-2-[2-(4-Chloro-phenyl)-benzoimidazol-1-yl]-N-cyclohexyl-2-(tetrahydro-pyran-4-yl)-acetamide,
(S)-2-[6-Chloro-2-(4-chloro-phenyl)-5-fluoro-benzoimidazol-1-yl]-N-cyclohexyl-2-(tetrahydro-pyran-4-yl)-acetamide,
(S)-2-[2-(4-Chloro-phenyl)-5,6-difluoro-benzoimidazol-1-yl]-2,N-dicyclohexyl-acetamide,
(S)-2-[2-(5-Chloro-thiophen-2-yl)-benzoimidazol-1-yl]-2,N-dicyclohexyl-acetamide,
(S)-2,N-Dicyclohexyl-2-[2-(2,3-difluoro-phenyl)-6-fluoro-benzoimidazol-1-yl]-acetamide,
2-[6-Chloro-2-(4-chloro-phenyl)-5-fluoro-benzoimidazol-1-yl]-N-cyclohexyl-2-cyclopentyl-acetamide,
and any pharmaceutically acceptable salt or ester thereof.

56. A compound of claim 1, selected from the group consisting of:
(S)-2-[6-Chloro-2-(4-chloro-phenyl)-5-fluoro-benzoimidazol-1-yl]-heptanoic acid cyclohexylamide,
(S)-2-[6-Chloro-2-(4-chloro-phenyl)-5-fluoro-benzoimidazol-1-yl]-N-cyclohexyl-2-cyclopentyl-acetamide,
2-[2-(4-Chloro-phenyl)-5-fluoro-benzoimidazol-1-yl]-2,N-dicyclohexyl-acetamide,
2-[1-(Cyclohexyl-cyclohexylcarbamoyl-methyl)-5,6-difluoro-1H-benzoimidazol-2-yl]-benzoic acid methyl ester,
2,N-Dicyclohexyl-2-(5,6-difluoro-2-pyridin-2-yl-benzoimidazol-1-yl)-acetamide,
2-[2-(5-Chloro-thiophen-2-yl)-5,6-difluoro-benzoimidazol-1-yl]-2,N-dicyclohexyl-acetamide,
2-[6-Chloro-1-(cyclohexyl-cyclohexylcarbamoyl-methyl)-5-fluoro-1H-benzoimidazol-2-yl]-benzoic acid methyl ester,
2-(6-Chloro-5-fluoro-2-pyridin-2-yl-benzoimidazol-1-yl)-2,N-dicyclohexyl-acetamide,
2-(6-Chloro-5-fluoro-2-pyridin-3-yl-benzoimidazol-1-yl)-2,N-dicyclohexyl-acetamide,
2-(6-Chloro-5-fluoro-2-pyridin-4-yl-benzoimidazol-1-yl)-2,N-dicyclohexyl-acetamide,
and any pharmaceutically acceptable salt or ester thereof.

57. A compound of claim 1, selected from the group consisting of:
2-[6-Chloro-2-(3-chloro-thiophen-2-yl)-5-fluoro-benzoimidazol-1-yl]-2,N-dicyclohexyl-acetamide,
2-[6-Chloro-2-(5-chloro-thiophen-2-yl)-5-fluoro-benzoimidazol-1-yl]-2,N-dicyclohexyl-acetamide,
(S)-2-[6-Chloro-2-(4-chloro-phenyl)-5-fluoro-benzoimidazol-1-yl]-3-ethyl-pentanoic acid cyclohexylamide,
2-[6-Chloro-5-fluoro-2-(4-fluoro-phenyl)-benzoimidazol-1-yl]-2,N-dicyclohexyl-acetamide,
2-[6-Chloro-2-(4-chloro-phenyl)-5-fluoro-benzoimidazol-1-yl]-2-cyclohexyl-N-cyclopentyl-acetamide,
2-[2-(4-Chloro-phenyl)-5,6-difluoro-benzoimidazol-1-yl]-N-cyclohexyl-2-(tetrahydro-pyran-4-yl)-acetamide, (S)-2-[2-(4-Chloro-phenyl)-5-fluoro-benzoimidazol-1-yl]-2,N-dicyclohexyl-acetamide, and any pharmaceutically acceptable salt or ester thereof.

58. A compound of claim 10 selected from the group consisting of:

- 2,N-Dicyclohexyl-2-[2-(3-dimethylamino-phenyl)-5,6-difluoro-benzoimidazol-1-yl]-acetamide,
- 2,N-Dicyclohexyl-2-[2-(3-dimethylamino-phenyl)-6-fluoro-benzoimidazol-1-yl]-acetamide,
- 2-[2-(4-Chloro-phenyl)-5,6-difluoro-benzoimidazol-1-yl]-2-cyclohexyl-N-(1-isopropyl-2-methyl-propyl)-acetamide,
- 2-[6-Chloro-2-(4-chloro-phenyl)-5-fluoro-benzoimidazol-1-yl]-2-cyclohexyl-N-(1-isopropyl-2-methyl-propyl)-acetamide,
- 2-[2-(3-Chloro-phenyl)-5,6-difluoro-benzoimidazol-1-yl]-2,N-dicyclohexyl-acetamide,
- 2-[2-(2-Chloro-phenyl)-5,6-difluoro-benzoimidazol-1-yl]-2,N-dicyclohexyl-acetamide,
- (S)-2-[6-Chloro-5-fluoro-2-(4-fluoro-phenyl)-benzoimidazol-1-yl]-2,N-dicyclohexyl-acetamide,
- 4-{2-cyclohexyl-2-[2-(4-methoxycarbonyl-phenyl)-benzoimidazol-1-yl]-acetylamino}-piperidine-1-carboxylic acid ethyl ester hydrogen chloride,
- 4-{1-[cyclohexyl-(3-formylamino-phenylcarbamoyl)-methyl]-1H-benzoimidazol-2-yl}-benzoic acid methyl ester hydrogen chloride,
- 2-cyclohexyl-2-[2-(2,4-dimethoxy-phenyl)-benzoimidazol-1-yl]-N-(2,6-dimethyl-phenyl)-acetamide,
- 2-cyclohexyl-2-[2-(2,4-dimethoxy-phenyl)-benzoimidazol-1-yl]-N-(1,1,3,3-tetramethyl-butyl)-acetamide,
- (S)-2-[2-(4-Chloro-phenyl)-benzoimidazol-1-yl]-2-cyclohexyl-N-(tetrahydro-pyran-4-yl)-acetamide,
- 2-[2-(4-Chloro-phenyl)-benzoimidazol-1-yl]-2-cyclohexyl-N-(1-isopropyl-2-methyl-propyl)-acetamide,
- 2-[2-(4-Chloro-phenyl)-5,6-difluoro-benzoimidazol-1-yl]-2-cyclohexyl-N-(tetrahydro-pyran-4-yl)-acetamide,
- 2-[6-Chloro-2-(4-chloro-phenyl)-5-fluoro-benzoimidazol-1-yl]-2-cyclohexyl-N-(tetrahydro-pyran-4-yl)-acetamide, and any pharmaceutically acceptable salt or ester thereof.

59. A compound of claim 1, selected from the group consisting of:

- 2-[2-(4-Chloro-phenyl)-6-fluoro-benzoimidazol-1-yl]-N-cyclohexyl-2-(tetrahydro-pyran-2-yl)-acetamide,
- 2-[6-Chloro-2-(4-chloro-phenyl)-5-fluoro-benzoimidazol-1-yl]-N-cyclohexyl-2-(tetrahydro-pyran-2-yl)-acetamide,
- (S)-2,N-Dicyclohexyl-2-[6-fluoro-2-(3-methyl-thiophen-2-yl)-benzoimidazol-1-yl]-acetamide,
- (S)-2-[2-(2-Chloro-phenyl)-5,6-difluoro-benzoimidazol-1-yl]-2,N-dicyclohexyl-acetamide,
- (S)-2-[2-(4-Chloro-phenyl)-5-fluoro-benzoimidazol-1-yl]-N-cyclohexyl-2-(tetrahydro-pyran-4-yl)-acetamide,
- (S)-2-[2-(4-Chloro-phenyl)-6-fluoro-benzoimidazol-1-yl]-N-cyclohexyl-2-(tetrahydro-pyran-4-yl)-acetamide,
- (S)-2-[2-(4-Chloro-phenyl)-6-fluoro-benzoimidazol-1-yl]-N-cyclohexyl-2-(R)-tetrahydro-pyran-2-yl-acetamide,
- (S)-2-[2-(4-Chloro-phenyl)-6-fluoro-benzoimidazol-1-yl]-N-cyclohexyl-2-(S)-tetrahydro-pyran-2-yl-acetamide,
- 2-[2-(4-Chloro-phenyl)-5-fluoro-benzoimidazol-1-yl]-N-cyclohexyl-2-(tetrahydro-pyran-2-yl)-acetamide,
- 2,N-Dicyclohexyl-2-[2-(3,4-dichloro-phenyl)-6-methoxy-benzoimidazol-1-yl]-acetamide, and any pharmaceutically acceptable salt or ester thereof.

60. A compound of claim 1, selected from the group consisting of:

- 2-[2-(4-Chloro-phenyl)-6-methoxy-benzoimidazol-1-yl]-2,N-dicyclohexyl-acetamide,
- 2-[2-(5-Chloro-thiophen-2-yl)-6-methoxy-benzoimidazol-1-yl]-2,N-dicyclohexyl-acetamide,
- 2-[2-(3-Chloro-4-methoxy-phenyl)-6-methoxy-benzoimidazol-1-yl]-2,N-dicyclohexyl-acetamide,
- 2-[2-(4-Chloro-3-fluoro-phenyl)-6-methoxy-benzoimidazol-1-yl]-2,N-dicyclohexyl-acetamide,
- 2-Cyclohexyl-N-cyclopentyl-2-[2-(3,4-dichloro-phenyl)-6-methoxy-benzoimidazol-1-yl]-acetamide,
- N-Cyclohexyl-2-cyclopentyl-2-[2-(3,4-dichloro-phenyl)-6-methoxy-benzoimidazol-1-yl]-acetamide,
- 2-[2-(4-Chloro-phenyl)-6-methoxy-benzoimidazol-1-yl]-2-cyclohexyl-N-cyclopentyl-acetamide,
- 2-[2-(3-Chloro-phenyl)-6-methoxy-benzoimidazol-1-yl]-2,N-dicyclohexyl-acetamide,
- 2,N-Dicyclopentyl-2-[2-(3,4-dichloro-phenyl)-6-methoxy-benzoimidazol-1-yl]-acetamide,
- 2-[2-(4-Chloro-phenyl)-6-methoxy-benzoimidazol-1-yl]-N-cyclohexyl-2-cyclopentyl-acetamide, and any pharmaceutically acceptable salt or ester thereof.

61. A compound of claim 1, selected from the group consisting of:

- 2-[2-(4-Chloro-3-fluoro-phenyl)-6-methoxy-benzoimidazol-1-yl]-2-cyclohexyl-N-cyclopentyl-acetamide,
- 2-[2-(3-Chloro-4-methoxy-phenyl)-6-methoxy-benzoimidazol-1-yl]-2-cyclohexyl-N-cyclopentyl-acetamide,
- 2,N-Dicyclohexyl-2-[2-(4-fluoro-phenyl)-6-methoxy-benzoimidazol-1-yl]-acetamide,
- 2-[2-(3-Chloro-phenyl)-6-methoxy-benzoimidazol-1-yl]-2-cyclohexyl-N-cyclopentyl-acetamide,
- 2-[2-(3-Chloro-4-methoxy-phenyl)-6-methoxy-benzoimidazol-1-yl]-N-cyclohexyl-2-cyclopentyl-acetamide,
- 2-[2-(5-Chloro-thiophen-2-yl)-6-methoxy-benzoimidazol-1-yl]-N-cyclohexyl-2-cyclopentyl-acetamide,
- 2-Cyclobutyl-N-cyclohexyl-2-[2-(3,4-dichloro-phenyl)-6-methoxy-benzoimidazol-1-yl]-acetamide,
- 2-[2-(5-Chloro-thiophen-2-yl)-6-methoxy-benzoimidazol-1-yl]-2-cyclohexyl-N-cyclopentyl-acetamide, and any pharmaceutically acceptable salt or ester thereof.

62. A compound of claim 1, selected from the group consisting of:

- 2-[2-(6-Chloro-pyridin-3-yl)-6-methoxy-benzoimidazol-1-yl]-2,N-dicyclohexyl-acetamide,
- 2-[2-(3-Chloro-phenyl)-6-methoxy-benzoimidazol-1-yl]-N-cyclohexyl-2-cyclopentyl-acetamide,
- 2-[2-(3-Chloro-4-methoxy-phenyl)-6-methoxy-benzoimidazol-1-yl]-2,N-dicyclopentyl-acetamide,
- 2,N-Dicyclohexyl-2-[6-methoxy-2-(6-trifluoromethyl-pyridin-3-yl)-benzoimidazol-1-yl]-acetamide,
- 2-[2-(5-Chloro-thiophen-2-yl)-6-methoxy-benzoimidazol-1-yl]-2-cyclobutyl-N-cyclohexyl-acetamide,
- 2-[2-(3-Chloro-phenyl)-6-methoxy-benzoimidazol-1-yl]-2-cyclobutyl-N-cyclohexyl-acetamide,
- N-Cyclohexyl-2-cyclopentyl-2-[2-(4-fluoro-phenyl)-6-methoxy-benzoimidazol-1-yl]-acetamide, and any pharmaceutically acceptable salt or ester thereof.

63. A compound of claim 1, selected from the group consisting of:

- 2-[1-(Cyclohexyl-cyclohexylcarbamoyl-methyl)-1H-benzoimidazol-2-yl]-benzamide,
- (S)-2,N-Dicyclohexyl-2-[2-(2,4-dimethoxy-phenyl)-benzoimidazol-1-yl]-acetamide, (S)-2-[2-(4-Chloro-phenyl)-benzoimidazol-1-yl]-2,N-dicyclohexyl-acetamide, (S)-2-[2-(4-Chloro-phenyl)-benzoimidazol-1-yl]-4-methyl-pentanoic acid cyclohexylamide, 2-[2-(4-Chloro-phenyl)-benzoimidazol-1-yl]-N-cyclohexyl-2-(4-trifluoromethyl-phenyl)-acetamide, (S)-2-Cyclohexyl-2-[2-(2,4-dimethoxy-phenyl)-benzoimidazol-1-yl]-N-(2,6-dimethyl-phenyl)-acetamide, (S)-2-[2-(4-Chloro-phenyl)-benzoimidazol-1-yl]-2-cyclohexyl-N-(4,4-difluoro-cyclohexyl)-acetamide, (S)-2-[6-Chloro-2-(4-chloro-phenyl)-5-fluoro-benzoimidazol-1-yl]-N-cyclohexyl-2-(tetrahydro-pyran-4-yl)-acetamide, (S)-2-[2-(5-Chloro-thiophen-2-yl)-benzoimidazol-1-yl]-2,N-dicyclohexyl-acetamide, (S)-2-[6-Chloro-2-(4-chloro-phenyl)-5-fluoro-benzoimidazol-1-yl]-heptanoic acid cyclohexylamide, (S)-2-[2-(4-Chloro-phenyl)-6-fluoro-benzoimidazol-1-yl]-N-cyclohexyl-2-(R)-tetrahydro-pyran-2-yl-acetamide, (S)-2-[2-(4-Chloro-phenyl)-6-fluoro-benzoimidazol-1-yl]-N-cyclohexyl-2-(S)-tetrahydro-pyran-2-yl-acetamide, 2-[2-(4-Chloro-phenyl)-5-fluoro-benzoimidazol-1-yl]-N-cyclohexyl-2-(tetrahydro-pyran-2-yl)-acetamide, and any pharmaceutically acceptable salt or ester thereof.

64. A compound of claim 10, selected from the group consisting of:

2-[6-Chloro-2-(4-chloro-phenyl)-5-fluoro-benzoimidazol-1-yl]-2-cyclohexyl-N-(tetrahydro-pyran-4-yl)-acetamide, 2-[2-(3-Chloro-phenyl)-5,6-difluoro-benzoimidazol-1-yl]-2,N-dicyclohexyl-acetamide, (S)-2,N-Dicyclohexyl-2-[6-fluoro-2-(3-methyl-thiophen-2-yl)-benzoimidazol-1-yl]-acetamide, (S)-2-[2-(2-Chloro-phenyl)-5,6-difluoro-benzoimidazol-1-yl]-2,N-dicyclohexyl-acetamide, and any pharmaceutically acceptable salt or ester thereof.

65. A pharmaceutical composition comprising a therapeutically effective amount of a compound of claim 1 and a pharmaceutically acceptable carrier and/or adjuvant.

* * * * *

UNITED STATES PATENT AND TRADEMARK OFFICE
CERTIFICATE OF CORRECTION

PATENT NO. : 7,645,785 B2
APPLICATION NO. : 11/821265
DATED : January 12, 2010
INVENTOR(S) : Benson et al.

It is certified that error appears in the above-identified patent and that said Letters Patent is hereby corrected as shown below:

Claim 1, column 98, line 21, delete "lower -alkyl-carbonyl-N(lower-alkyl), lower-alkyl-car-"
and insert -- lower-alkyl-carbonyl-N(lower-alkyl), lower-alkyl-car- --

Claim 1, column 98, line 27, delete "consisting of lower-alkyl, phenyl, lower-alkoxy -car-"
and insert -- consisting of lower-alkyl, phenyl, lower-alkoxy-car- --

Claim 9, column 100, line 44, delete "sub stituents" and insert -- substituents --

Claim 14, column 102, delete lines 8 through 16
and insert -- wherein the cycloalkyl, aryl, heteroaryl or heterocyclyl group of any
option for $R^1$ above is optionally substituted with 1 to 3 substituents
independently selected from the group consisting of: lower-alkyl, lower-alkoxy,
lower-alkoxy-carbonyl, morpholinyl, formylamino, halogen, hydroxyl, fluoro-lower-alkyl,
fluoro-lower-alkoxy, lower-alkyl-carbonyl-N(lower-alkyl), lower-alkyl-carbonyl-N(H),
$NH_2$, N(H, lower-alkyl), N(lower-alkyl)$_2$, carboxy, carbamoyl,
N(H, lower-alkyl)C(O), and N(lower-alkyl)$_2$C(O); --

Claim 14, column 102, line 35, delete "lower -alkyl-carbonyl-N(lower-alkyl), lower-alkyl-car-"
and insert -- lower-alkyl-carbonyl-N(lower-alkyl), lower-alkyl-car- --

Claim 14, column 102, line 47, delete "alkoxy, lower-alkoxy-carbonyl, lower-alkyl-carbo-"
and insert -- alkoxy, lower-alkoxy-carbonyl, lower-alkyl-carbo- --

Claim 14, column 102, line 51, delete "Ri" and insert -- $R^3$ --

Claim 30, column 105, line 56, delete "nyl)-enzoimidazol-1-yl]-acetamide,"
and insert -- nyl)-benzoimidazol-1-yl]-acetamide, --

Claim 36, column 107, line 34, delete "2,N-dicyclohexyl-2-[2-(4-[1,2,3 ]thiadiazol-4-yl-phenyl)-"
and insert -- 2,N-dicyclohexyl-2-[2-(4-[1,2,3]thiadiazol-4-yl-phenyl)- --

Signed and Sealed this

Eighteenth Day of May, 2010

David J. Kappos
*Director of the United States Patent and Trademark Office*

CERTIFICATE OF CORRECTION (continued)
U.S. Pat. No. 7,645,785 B2

Claim 36, column 107, line 37, delete "dol-5-yl)-benzoimidazol-1-yl]acetamide   hydrogen" and insert -- dol-5-yl)-benzoimidazol-1-yl]acetamide hydrogen --

Claim 37, column 107, line 47, delete "bamoyl]-methyl}-1H -benzoimidazol-2-yl)-benzoic" and insert -- bamoyl]-methyl}-1H-benzoimidazol-2-yl)-benzoic --

Claim 37, column 107, line 50, delete "oyl)-methyl}-1H-benzoimidazol-2-yl}-benzoic  acid" and insert -- oyl)-methyl}-1H-benzoimidazol-2-yl}-benzoic acid --

Claim 37, column 107, line 56, delete "oyl)-methyl}-1H-benzoimidazol-2-yl}-benzoic  acid" and insert -- oyl)-methyl}-1H-benzoimidazol-2-yl}-benzoic acid --

Claim 41, column 109, line 10, delete "2-[1-(Cyclohexyl-cyclohexyl-" and insert at the beginning of line 11, -- 2-[1-(Cyclohexyl-cyclohexyl- --

Claim 46, column 110, line 52, delete "2-(2-Benzo [b]thiophen-2-yl-benzoimidazol-1-yl)-2,N-" and insert -- 2-(2-Benzo[b]thiophen-2-yl-benzoimidazol-1-yl)-2,N- --

Claim 47, column 111, line 19, delete "2,N-Dicyclo-" and insert at the beginning of line 20 -- 2,N-Dicyclo- --

Claim 49, column 112, line 3, delete "2,N-Dicyclohexyl-2-[2-(3 ',4'-dichloro-biphenyl-4-yl)" and insert -- 2,N-Dicyclohexyl-2-[2-(3',4'-dichloro-biphenyl-4-yl) --

Claim 54, column 113, line 33, delete "claim 10" and insert -- claim 9 --

Claim 54, column 113, line 59, delete "N-isopropyl-2-[2-(1-methyl-iH-pyrrol-2-yl)-benzoimida-" and insert -- N-isopropyl-2-[2-(1-methyl-1H-pyrrol-2-yl)-benzoimida- --

Claim 58, column 115, line 4, delete "claim 10" and insert -- claim 9 --

Claim 58, column 115, line 23, delete "zoimidazol-1-yl]-acetylamino }-piperidine-1-carboxy-" and insert -- zoimidazol-1-yl]-acetylamino}-piperidine-1-carboxy- --

Claim 64, column 118, line 7, delete "claim 10" and insert -- claim 9 --